(12) United States Patent
Kaether et al.

(10) Patent No.: US 9,828,344 B2
(45) Date of Patent: Nov. 28, 2017

(54) INHIBITORS OF THE NOTCH SIGNALING PATHWAY AND SECRETION FOR USE IN MEDICINE

(71) Applicant: Leibniz-Institut für Altersforschung Fritz-Lipmann-Institut e.V. (FLI), Jena (DE)

(72) Inventors: Christoph Kaether, Jena (DE); Andreas Krämer, Jena (DE)

(73) Assignee: LEIBNIZ-INSTITUT FÜR ALTERSFORSCHUNG FRITZ-LIPMANN-INSTITUT E.V. (FLI), Jena (DE)

( * ) Notice: Subject to any disclaimer, the term of this patent is extended or adjusted under 35 U.S.C. 154(b) by 0 days.

(21) Appl. No.: 14/404,330

(22) PCT Filed: Jun. 3, 2013

(86) PCT No.: PCT/EP2013/061363
§ 371 (c)(1),
(2) Date: Nov. 26, 2014

(87) PCT Pub. No.: WO2013/178821
PCT Pub. Date: Dec. 5, 2013

(65) Prior Publication Data
US 2015/0175548 A1 Jun. 25, 2015

(30) Foreign Application Priority Data
Jun. 1, 2012 (EP) .................................. 12170403

(51) Int. Cl.
*C07D 215/54* (2006.01)
(52) U.S. Cl.
CPC .................... *C07D 215/54* (2013.01)
(58) Field of Classification Search
None
See application file for complete search history.

(56) References Cited

U.S. PATENT DOCUMENTS

| 3,775,422 A | 11/1973 | Bossert et al. |
| 2007/0265327 A1 | 11/2007 | Chen et al. |
| 2011/0015201 A1* | 1/2011 | Chen .................... A61K 31/47 514/250 |

FOREIGN PATENT DOCUMENTS

| DE | 20 03 146 A1 | 7/1971 |
| DE | 20 03 148 A1 | 7/1971 |
| WO | WO 2006/074419 A2 | 7/2006 |
| WO | WO 2008/070875 A2 | 6/2008 |
| WO | WO 2008/103470 A2 | 8/2008 |
| WO | WO 2009/006580 A1 | 1/2009 |
| WO | WO 2009/102864 A1 | 8/2009 |
| WO | WO 2011/050353 A1 | 4/2011 |
| WO | WO 2012/063085 A2 | 5/2012 |

OTHER PUBLICATIONS

Leong et al. (Blood, Mar. 15, 2006 vol. 107, No. 6).*
Patani and LaVoie (Chem. Rev. 1996, 96, 3147-3176).*
Shih and Wang (Cancer Res 2007; 67: (5).Mar. 1, 2007).*
Edraki, N. et al. 2009 "Dihydropyridines evaluation of their current and future pharmacological applications" *Drug Discovery Today* 14; 21-22.
Evans, C.G. et al. 2011 "Identification of dihydropyridines that reduce cellular tau levels" *Chemical Communications* 47; 529-531.
Lack, et al. "Targeting the binding function 3 (BF3) site of the human androgen receptor through virtual screening" *Journal of Medicinal Chemistry* 54; 8563-8573.
Takahashi, D. et al. 2008 "Structure-activity relationships of receptor binding of 1, 4-dihydropyridine derivatives" *Biological & Pharmaceutical Bulletin* 31(3); 473-479.
Vitolinya, et al. 1981 "Synthesis and pharmacological activity of some derivatives of condensed 1, 4-dihydopyridines" *Pharmaceutical Chemistry Journal* 15(1); 17-19.

* cited by examiner

*Primary Examiner* — Kortney L. Klinkel
*Assistant Examiner* — William Lee
(74) *Attorney, Agent, or Firm* — Knobbe, Martens, Olson & Bear, LLP

(57) ABSTRACT

The invention relates to dihydropyridine compounds as inhibitors of the notch signalling pathway and/or inhibitors of secretion for the treatment of secretion-dependent disease, such as cancer or senescence-related ageing, in addition to pharmaceutical compositions thereof and methods of treatment.

Figure 1:
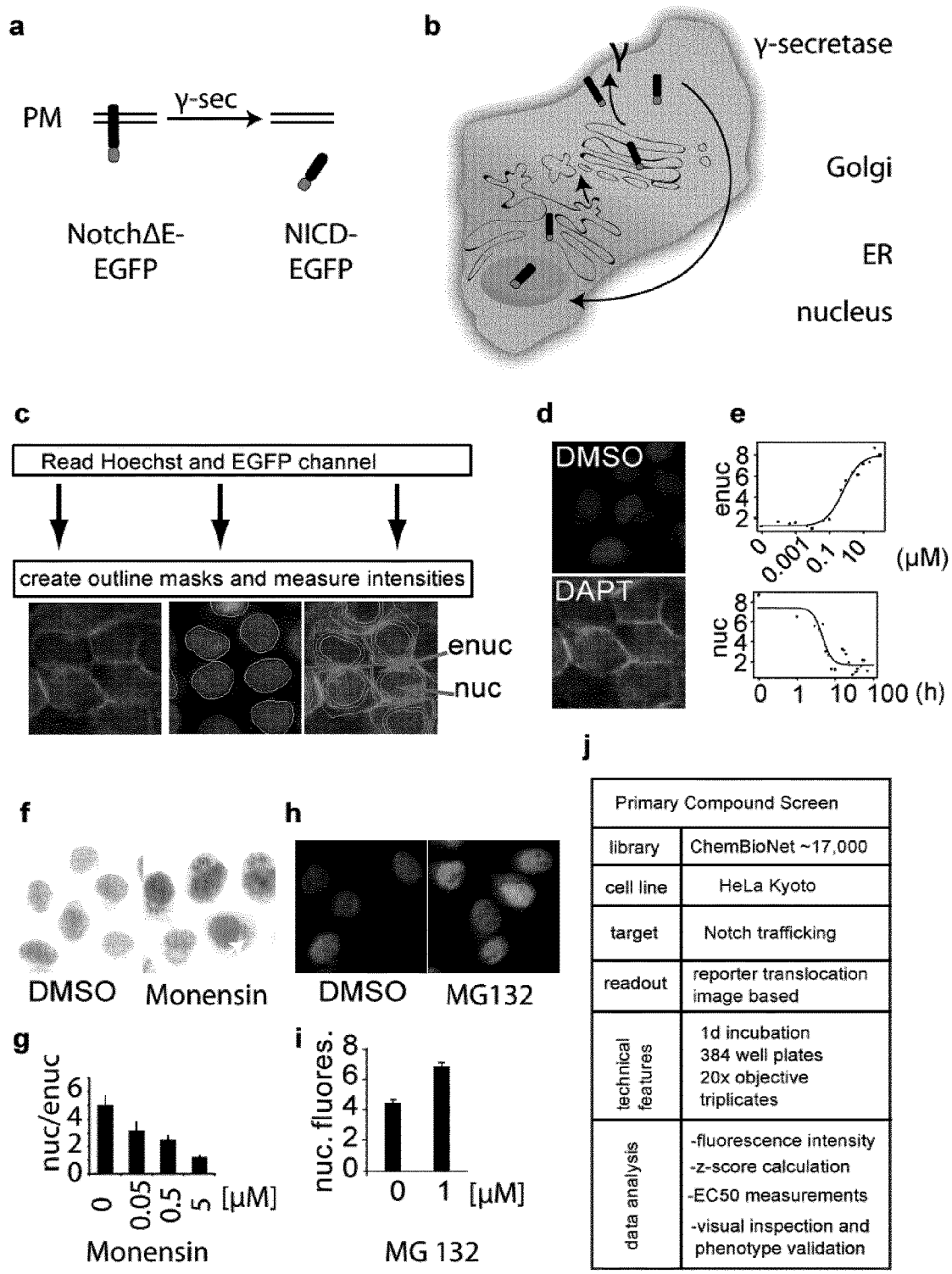

9 Claims, 18 Drawing Sheets a nifedipine
nimodipine         1 - 6         7

| compound | R | X | Y | Z | $EC_{50}$ / mM |
|---|---|---|---|---|---|
| nifedipine | Me | $NO_2$ | H | Me | > 100 |
| nimodipine | iso-pr | H | $NO_2$ | $(CH_2)_2OMe$ | > 100 |
| 1 (FLI-06) | cyclo-hex | $NO_2$ | C | O | 2.3 ± 0.8 |
| 2 (FLI-24) | iso-pr | $NO_2$ | C | O | 24 ± 28 |
| 3 (FLI-27) | pent | $NO_2$ | C | O | 6.2 ± 0.6 |
| 4 (FLI-28) | cyclo-hept | $NO_2$ | C | O | 1.1 ± 0.7 |
| 5 (FLI-25) | cyclo-hex | H | C | O | 14.9 ± 3.0 |
| 6 | cyclo-hex | $NO_2$ | C | $N-OCH_2COOR'$ | > 100 |
| 7 | cyclo-hex | $NO_2$ | C | O | > 100 | b

C

WO 2009/102864; HPI-1

WO 2008/103470; C3

WO 2008/103470; C4

WO 2008/103470; C5

WO 2008/070875; ST216093 a b

| Structure | EC50 Chart | Properties | |
|---|---|---|---|
| [structure] | [curve] | Name:<br>MW:<br>Formula:<br>PubchemID:<br>$EC_{50}$: | FLI-06<br>438.53<br>C25H30N2O5<br>3103157<br>2.3 ± 0.8 μM |
| [structure] | NA | Name:<br>MW:<br>Formula:<br>PubchemID:<br>$EC_{50}$: | FLI-13<br>395.52<br>C22H29N6O<br>22422757<br>NA |
| [structure] | [curve] | Name:<br>MW:<br>Formula:<br>PubchemID:<br>$EC_{50}$: | FLI-14<br>512.61<br>C30H32N4O4<br>4299201<br>9.2 ± 1.9 μM |
| [structure] | [curve] | Name:<br>MW:<br>Formula:<br>PubchemID:<br>$EC_{50}$: | FLI-15<br>405.49<br>C17H19N5O3S2<br>9550519<br>28.9 ± 5.7 μM |

Fig. 20

INHIBITORS OF THE NOTCH SIGNALING PATHWAY AND SECRETION FOR USE IN MEDICINE

The invention relates to chemical compounds as inhibitors of the notch signalling pathway and/or secretion for the treatment of secretion-dependent disease, such as cancer or senescence-related ageing, in addition to pharmaceutical compositions thereof and methods of treatment.

BACKGROUND OF THE INVENTION

Notch is an important regulator of gene transcription involved in cellular differentiation, lateral inhibition and tissue homeostasis. In Notch signaling the Notch precursor protein is activated in the trans-Golgi-network by proteolytic cleavage. This cleavage generates two fragments that comprise the active Notch-receptor, which is then translocated to the plasma membrane (PM). Upon interaction with its ligand from the Delta/Serrate/Jagged family it is subsequently processed by ADAM 17 and finally by gamma-secretase to generate the Notch intracellular domain (NICD). NICD is translocated to the nucleus, where it activates a transcription factor of the CSL family (CBF1 (RBP-J) in vertebrates, Su(H) in *Drosophila*, Lag-1 in *C. elegans*). NICD is composed of several Ankyrin repeats and an N-terminal RAM domain, which is critical for the activation of CSL (for review see[1]). Furthermore, one characteristic and important hallmark of the Notch signaling pathway is the independence of second messengers. Thus, the amount of NICD inside the nucleus is proportional to the amount of processed Notch receptor.

The final cleavage step that releases NICD from the PM is mediated by gamma-secretase. gamma-secretase is a heteromultimeric integral membrane protein with protease activity[2]. Interacting and potentially regulating proteins were shown[3-6] but a commonly accepted view of the regulation of gamma-secretase is lacking. Notch signaling can be fine-tuned at several steps, ranging from glycosylation at the ectodomain, interaction with inhibitors like Numb, ubiquitinylation and phosphorylation of NICD to slight variations at the gamma-secretase cleavage site (for review see[1]). Fine-tuning can regulate trafficking of the receptor, ligand binding-affinity, endocytosis rate of the receptor and stability of NICD[1,7]. Despite the wealth of information about Notch signaling, its trafficking and regulation of signaling is not fully understood.

Therapeutic interventions of aberrant Notch signaling, for example in cases of T cell-lineage acute lymphoblastic leukemia (T-ALL) at present are aimed/tested at the level of ligand-binding and gamma-secretase cleavage, but novel strategies would be highly desired[8,9].

Natural compounds like Brefeldin A (BFA), Shiga- or Cholera-toxin turned out to be invaluable tools to dissect molecular details of membrane trafficking at various steps in the exo- or endocytic pathway[10].

Similarly, gamma-secretase related research could not have come this far without the identification of gamma-secretase inhibitors (GSI) such as DAPT or L685,458. These and other GSIs turned out to be not only invaluable to inhibit gamma-secretase but also to purify it, elucidate structure-function relations within the gamma-secretase complex and identify substrate-docking sites (13).

High content screening (HCS) describes the process of automated image acquisition of phenotypes of cells or organisms and the subsequent automated analysis of these phenotypes by image analysis algorithms without or only little user intervention allowing for high throughput applications such as genome-wide RNAi or large chemical compound libraries (for review see 14).

Despite various innovative screening strategies having been applied, there is a need in the field to find further inhibitors of the notch signaling pathway for application in medicine.

GSIs have been applied in the treatment of cancer, based on the finding that Notch signaling is misregulated in various cancers. The Notch signalling pathway is an important component in the molecular mechanisms that regulate cell fate during development, in addition to cancer formation. Aberrant activation of the Notch pathway contributes to tumour formation. The important role of Notch in human cancer has been highlighted by the presence of activating mutations and amplification of Notch genes in human cancer and by the demonstration that genes in the Notch signalling pathway could be potential therapeutic targets. One of the major therapeutic targets in the Notch pathway are the Notch receptors, in which γ-secretase inhibitors prevent the generation of the oncogenic (intracellular) domain of Notch molecules and suppress Notch activity. Further notch inhibitors are therefore sought after as potential cancer therapeutics.

Despite the promising effects of gamma-secretase inhibitors, known inhibitors are plagued by significant side effects during and after treatment of patients. Major side effects relate to gastrointestinal toxicity, such as nausea, diarrhea, vomiting, weight loss and/or loss of appetite.

The present invention therefore provides novel compounds not previously identified as Notch inhibitors. Furthermore, the compounds of the present invention show an anti-secretion function and play a role in membrane trafficking, inhibiting secretion at a pre-ER exit step. The effect of administration of the compounds of the invention in pre-clinical assays shows a notch phenotype in addition to disruption of secretion at an early stage. This effect enables the compounds as disclosed herein to be administered in the treatment of diseases associated with secretion or secretion pathways.

One example of such a condition is senescence-related ageing, whereby senescent cells lose their proliferative capacity once senescence occurs and show an enhanced secretion of pro-inflammatory cytokines, which is also known as the "senescence associated secretory phenotype (SASP):

Accumulation of nuclear DNA damage represents one of the molecular causes of aging. Accordingly, there is an age-dependent accumulation of DNA damage in numerous human tissues and genetic diseases that lead to premature aging are often caused by mutations in genes involved in DNA damage repair; and animal models provided a proof of concept that DNA damage accumulation leads to premature aging. Cells respond to DNA damage by activating checkpoints that prevent the contribution of damaged cells to tissue homeostasis by induction of cell death (apoptosis), cell cycle arrest (senescence) or self-digestion of the damaged cells (autophagy).

Senescent cells lose their proliferative capacity and show an enhanced secretion of pro-inflammatory cytokines, which is also known as the "senescence associated secretory phenotype (SASP)". It has been shown that SASP affects neighbouring, non-senescent cells and this may impact on tissue aging and cancer formation. Methods or means for the inhibition of SASP could delay tissue dysfunction and extend healthy lifespan.

Little is known about the SASP-underlying changes in structure and composition of the secretory pathway. Senescence is associated with morphological changes in the secretory pathway like dispersal of the Golgi, increase in lysosomal volume, increase in lysosomal lipofuscin aggregation and increased expression of the lysosomal enzyme β-galactosidase. In light of the secretion phenotype associated with SASP, inhibitors of secretion represent a promising means for treating illness associated with SASP. At the present time no effective therapeutic approaches for the treatment of SASP-associated disease are known, and appropriate secretion inhibitors for the treatment of such disorders are required.

The compounds of the present invention therefore relate to FLI-06 and structurally similar derivatives that exhibit the properties desired in compounds for treatment of secretion-dependent disease, such as cancer or ageing.

Structurally similar compounds have been previously disclosed in relation to different biological effects or for the treatment of different medical conditions. WO 2009/102864 discloses structurally similar compounds to those of the present invention as antagonists of the hedgehog signaling pathway. However, the compounds disclosed therein are not mentioned in relation to secretion or notch signaling inhibition and additionally show different structural features, for example the ester position of R2 of formula I of the present invention is distinct from those compounds of WO 2009/102864, which exhibit an alkoxy methoxyethyl group at the corresponding position.

WO 2008/103470 discloses structurally similar compounds to those of the present invention as RAS-specific anti-cancer agents. However, the compounds disclosed therein are not mentioned in relation to secretion or notch signaling inhibition and additionally show different structural features, for example the ester position of R2 of formula I of the present invention is distinct from those compounds of WO 2008/103470, which exhibit an alkoxy group at the corresponding position. Furthermore, the compounds of WO 2008/103470 exhibit a phenyl substituent in place of R6. Additionally the compounds disclosed therein exhibit a different central ring structure compared to the compounds of formula I of the present invention.

WO 2011/050353 discloses structurally similar compounds to those of the present invention for the treatment of androgen-receptor-positive cancer cells. However, the compounds disclosed therein are not mentioned in relation to secretion or notch signaling inhibition and additionally show different structural features, for example the ester position of R2 of formula I of the present invention is distinct from those compounds of WO 2011/050353, which exhibit a phenylethyl group. It is noteworthy that none of the compounds disclosed in the art that exhibit structural similarity to the presently claimed compounds and are intended for cancer treatment exhibit a substitution of the hexahydroquinoline ring at position 7 with two methyl groups.

WO 2008/070875 also discloses structurally similar compounds to those of the present invention. The compounds of WO 2008/070875 are only disclosed in relation to the treatment of Alzheimer's disease and are not mentioned in relation to secretion or notch signaling inhibition.

SUMMARY OF THE INVENTION

The compounds of the invention were products of an assay established to monitor membrane trafficking and processing of a ligand-independent Notch-GFP reporter by automated microscopy. 16.671 small compounds were screened and relevant candidates validated by cellular and in vitro assays as well as by using zebrafish as an in vivo model. FLI-06 functions by disrupting the Golgi apparatus, different from Brefeldin A and Golgicide A. Detailed analysis reveals that FLI-06 inhibits secretion at a pre-ER exit step, making it the first identified compound that blocks secretory traffic at such an early stage. The further derivatives of the invention as tested herein also demonstrate similar disruption of secretion and membrane trafficking. Molecular characterization of selected compounds identified novel inhibitors of ER-export, which have the unique property to inhibit cargo recruitment to ER exit sites.

The invention is therefore based on a novel type of secretion inhibitor, FLI-06 and derivatives thereof. In contrast to other secretion inhibitors, no gross ER stress is induced. FLI-06 and its derivatives represent useful medicaments for inhibiting or reducing secretion without inducing ER-stress mediated apoptosis.

The combination of disruption of membrane traffic and secretion and notch signalling inhibition, together with the treatment of secretion-dependent disease represents a novel and non-obvious development in the field. This combination of compound, mechanism and medical use has not been suggested previously with regard to any of the previously known notch inhibitors. This combination (which is common to the compounds of the present invention) represents a unique contribution to the prior art.

In light of the prior art the technical problem underlying the invention was the provision of compounds for the inhibition of notch signaling via inhibition of secretion for use in medicine, in particular providing pharmaceutically active compounds that exhibit fewer side effects than known notch inhibitors.

This problem is solved by the features of the independent claims. Preferred embodiments of the present invention are provided by the dependent claims.

The invention therefore relates to compounds according to the general formula I as inhibitors of the notch signalling pathway for use as a medicament for the treatment of a secretion-dependent disease

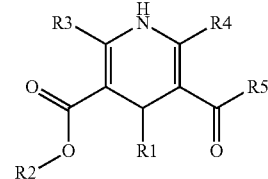

Formula I whereby R1 is one of:

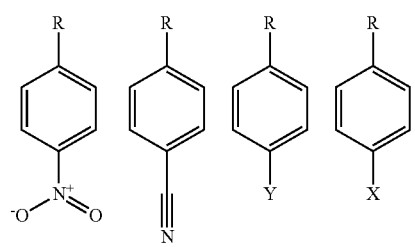

-continued

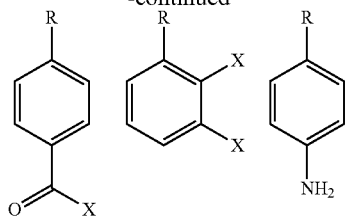

whereby X is H or a halogen, preferably F, Cl, Br or I, and Y is COOCH$_3$ or CF3, or COOH;

R2 is a straight chain or branched alkyl group of C$_1$-C$_8$, or a carbon ring structure of C$_5$-C$_8$, preferably one of

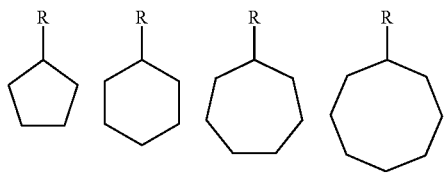

R3 is H or a straight chain or branched alkyl group of C$_1$-C$_6$;

R4 is H or a straight chain or branched alkyl group of C$_1$-C$_6$, preferably a branched alkyl group selected from

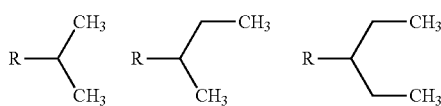

R5 is H or a straight chain or branched alkyl group of C$_1$-C$_6$;

whereby R4 and R5 may be closed with a C$_3$ group to form a C$_6$ ring structure with the group

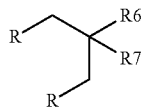

whereby R6 and/or R7 is H or a straight chain or branched alkyl group of C$_1$-C$_6$;

whereby "R" of the substituents R1, R2, R4, R5 represents the backbone of general formula I.

In a preferred embodiment of the invention the compounds of formula I are further characterised by the general formula II

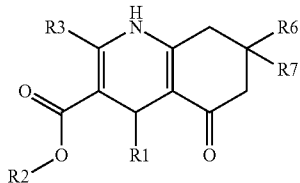

whereby R1-R3 are as defined by formula I, and R6 and/or R7 is H or a straight chain or branched alkyl group of C$_1$-C$_6$.

The invention therefore relates to formula I and/or II

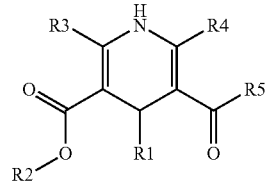

Formula I

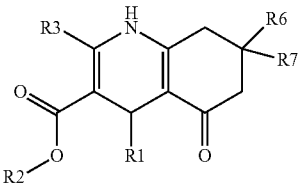

Formula II whereby R1 is one of:

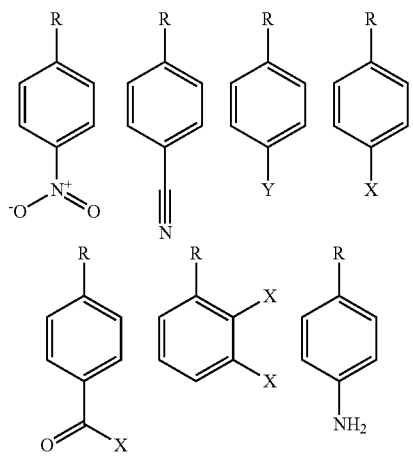

whereby X: H or a halogen, preferably F, Cl, Br or I, and Y: COOCH$_3$ or CF3, COOH, R2 is a straight chain or branched alkyl group of C$_1$-C$_8$, or a carbon ring structure of C$_5$-C$_8$, preferably one of

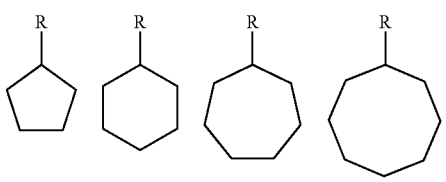

R3 is H or a straight chain or branched alkyl group of C$_1$-C$_6$,

R4 is H or a straight chain or branched alkyl group of C$_1$-C$_6$, preferably a branched alkyl group selected from

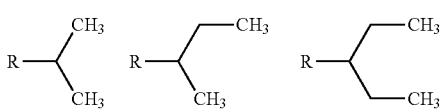

R5 is H or a straight chain or branched alkyl group of C$_r$C$_6$, and

R6, R7 is H or a straight chain or branched alkyl group of $C_1$-$C_6$, whereby "R" of the substituents R1, R2, R4 represents the backbone of general formula I-a or I-b In a preferred embodiment the compounds of the present invention are characterised by the general formula III

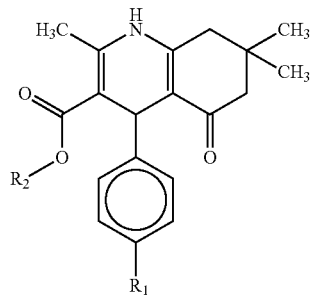

Formula III whereby R1: H, $COOCH_3$, COOH, CN, $NO_2$, $CF_3$, or $NH_2$ and R2: a straight chain or branched alkyl group of $C_1$-$C_8$, preferably $C_2$-$C_6$, or a carbon ring structure, preferably $C_5$, $C_6$, $C_7$ or $C_8$.

The present invention relates additionally to compounds with a structure according to any one of formulae I, nor III, whereby R2 to R7 are as defined as in formula I, nor III and R1 is

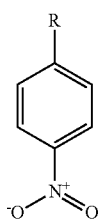

Specific compounds of the invention relate to those selected from the group comprising of FLI-06, FLI-24, FLI-25, FLI-26, FLI-27 and/or FLI-28 as inhibitors of the notch signalling pathway for use as a medicament for the treatment of a secretion-dependent disease.

FLI-06

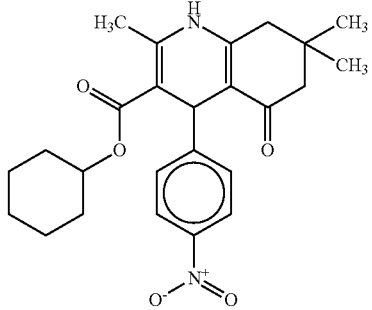

-continued

FLI-24

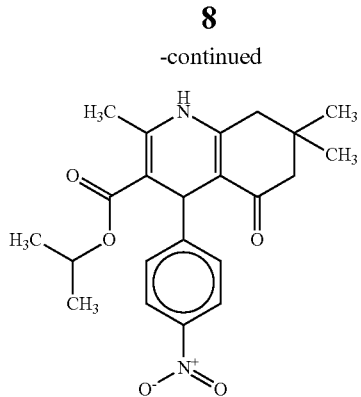

FLI-25

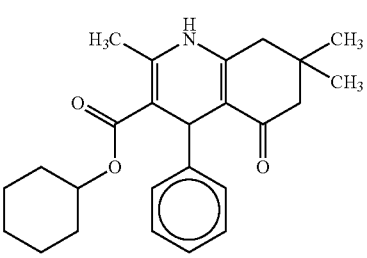

FLI-26

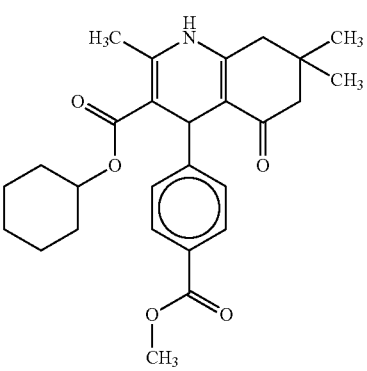

FLI-27

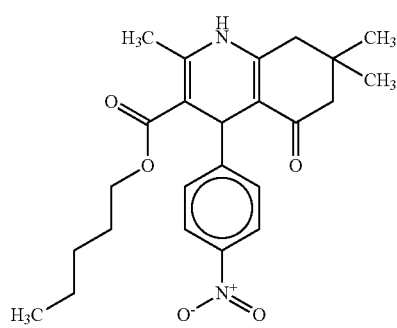

FLI-28

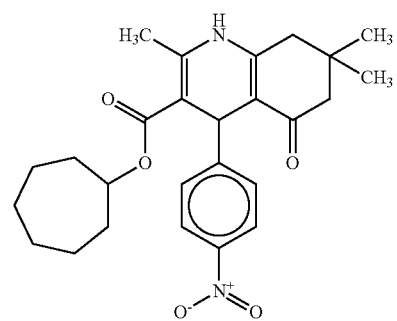

In a preferred embodiment of the invention the medical use for the treatment of secretion dependent diseases is further defined in that secretion-dependent diseases may be selected from those diseases for which their aetiology, pathogenesis, morphologic features and/or clinical manifestations are characterised by a dependence on cellular secretion and/or a secretory pathway, and/or by levels of secretion of secreted compounds, preferably proteins, above normal levels (for example in comparison to a healthy subject or relevant control), whereby a therapeutic effect in the treatment of said diseases is induced by the inhibition of cellular secretion. Relevant controls may relate to individuals that do not exhibit disease, or exhibit some secretion of proteins or other substances at a level that does not contribute or contributes to a smaller extent to a disease state.

The compounds as described herein disrupt a secretory pathway, in particular the ER and/or golgi apparatus. This represents a beneficial technical effect that is common to the compounds disclosed herein and represents a surprising effect, neither suggested nor disclosed in the prior art for Notch pathway inhibitors.

The various medical uses encompassed by the invention are therefore unified by a common functional feature relating to an unexpected technical effect. The role that FLI-06 and derivatives thereof as described herein play in disrupting secretion had been neither disclosed nor suggested in the art. A number of diseases rely on secretion with regard to their etiology, pathogenesis, morphologic features and/or clinical manifestations.

Such diseases include, but are not limited to several cancers that are dependent on hyperactive wnt-signaling, a secreted molecule (Herr et al., Trends in Mol. Med. 2012); glioblastoma (Formolo et al. 2011, J. Proteome Research; cancer and inflammatory diseases that secrete various interleukins (McLaughlin et al. 2010, British J. of Pharmacology. Inhibition of secretion as anti-cancer drug was suggested for example in Ohashi et al. JBC 2011.

A skilled person is able to determine such secretion-dependent diseases on the basis of existing methods, especially in light of the present invention. The experimental examples of the present invention encompass a number of appropriate methods for assaying secretion in vivo or in vitro. Such approaches may be applied for example to patient samples in order to determine the existence of such a disease.

A secretion dependent disease may for example be identified by the detection of enzymatic reactions in case of enzymatically active secreted proteins such as disclosed in the SEAP assay, or by measuring the secreted proteins via ELISA or similar methods known to the skilled person.

In further embodiments of the invention, the secretion or secretory pathway is related to, mediated and/or characterised by cytokine secretion, TNFα secretion, IL-6 secretion, IL-8 secretion, IL-10 secretion, Wnt secretion, microRNA secretion, CCL2-secretion, ER transport and/or the Golgi apparatus.

The technical effect of inhibiting membrane traffic is significant for application of the compounds of the present invention. Knowledge of this particular mechanism provides insight into the requirements necessary for appropriate pharmaceutical administration (ie administration conditions should preferably enable cell entry, compounds could be prepared potentially to be lipid (or organic solvent) soluble), and thereby providing novel information on targeting the disease to be treated.

In one embodiment the information relating to inhibition of membrane trafficking, or disruption of the secretory pathway, preferably by disruption of the ER and/or golgi apparatus, may lead to treatment of novel patient collectives or novel administration regimes, that were not possible without the information regarding the technical effect and/or mechanism of the molecules described herein.

One aspect of the invention relates to treatment of the secretion-dependent disease of cancer. The medical use of the compounds described herein and methods of treatment therefore relate to the treatment of cancer.

One aspect of the invention relates to treatment of the secretion-dependent disease of senescence-related ageing. The medical use of the compounds described herein and methods of treatment therefore relate to the treatment of senescence-related ageing and associated illnesses.

One embodiment of the invention is characterised in that the cancer to be treated is characterised by a dependency on membrane traffic, secretion or a secretory pathway, preferably related to and/or mediated by wnt secretion, microRNA secretion, CCL2-secretion, ER transport and/or the Golgi apparatus. In a preferred embodiment the cancers dependent on secretion are selected from chronic lymphocytic leukemia (CLL), esophageal cancer, glioma, colon cancer or breast cancer.

Some cancers are known that are dependent on mechanisms of secretion. For example, a non-comprehensive list of cancers dependent on secretion relates to chronic lymphocytic leukemia (CLL) (ER transport; Carew, J. S., et al. (2006), Targeting endoplasmic reticulum protein transport: a novel strategy to kill malignant B cells and overcome fludarabine resistance in CLL. Blood 107, 222-231), esophageal cancer (wnt secretion; Fu, L., et al. (2011), Wnt2 secreted by tumour fibroblasts promotes tumour progression in oesophageal cancer by activation of the Wnt/beta-catenin signalling pathway. Gut 60, 1635-1643), glioma (wnt secretion; Augustin, I. et al. (2012), The Wnt secretion protein Evi/Gpr177 promotes glioma tumourigenesis. EMBO Molecular Medicine 4, 38-51), colon cancer (wnt secretion), breast cancer metastasis (microRNA secretion; Breast Cancer-secreted MicroRNAs in the Pre-metastatic Niche, and CCL2 secretion; Loss of TGF-beta signaling in mammary fibroblasts enhances CCL2 secretion to promote mammary tumor progression through macrophage dependent and independent mechanisms Stacey L Hembruff, et al. Neoplasia 2010, Volume 12, Issue 5). Because the compounds provided herein show the surprising effect of disrupting secretion pathways at an early stage in addition to Notch signalling, the invention relates to the novel combination of notch signalling disruption, secretion disruption at an early stage and cancer treatment.

One embodiment of the invention is characterised in that the cancer to be treated is characterised by misregulation of the notch signalling pathway. Preferred cancers are haematological cancer, colorectal cancer, cervical cancer, pancreatic cancer, breast cancer or lung cancer. In a preferred embodiment the haematological cancer is a lymphoma or leukemia. In a preferred embodiment the lymphoma is a T-cell lymphoma, B-cell lymphoma or Hodgkin lymphoma or CLL (Rosati et al, Blood 2009 113:856-865).

In a preferred embodiment the compound of the present invention is an inhibitor of the notch signalling pathway intended for use as a medicament in the treatment of cancer, wherein the compound does not directly inhibit γ-secretase.

In a preferred embodiment the compound is characterised in that the side effects that arise during treatment with the compound are absent or present to a lesser extent in comparison to treatment with a direct γ-secretase inhibitor. Gamma-secretase inhibitors are well-known as Notch signalling inhibitors, but there are however plagued by various side effects. The fact the compounds of the present invention demonstrate a gamma-secretase independent effect represents a surprising and beneficial effect, which provides improved conditions for medical application due to the inherently reduced side effects likely to arise during treatment due to not directly disrupting gamma-secretase as current notch inhibitors do. An effect of this is that gastrointestinal side effects, such as nausea, diarrhea, vomiting, weight loss and/or loss of appetite are avoided or reduced.

Until the present time, notch signalling inhibitors that do not directly influence gamma-secretase are rare. Those few molecules known that inhibit notch signalling, but that do not inhibit gamma-secretase directly, are not known in cancer treatment, or are not known as disrupters of membrane transport, and particularly not as disrupters of ER transport or the Golgi apparatus. This therefore represents a novel and non-obvious medical effect. Due to the common feature of non- or indirect gamma-secretase activity (ie the effect against notch signalling does not directly occur on gamma-secretase), in combination with an anti-secretion effect, the compounds of the invention offer the likely advantage that those side effects associated with GSIs are significantly reduced during treatment with the compounds of the present invention.

The combination of non-GSI compounds (non-gamma secretase inhibitors; compounds that do not directly influence gamma secretase function), notch signalling inhibition and inhibition of secretion is a novel and non-obvious development in the field. This combination of compound, mechanism and medical use has not been suggested previously with regard to any of the previously known notch inhibitors. This combination (which is common to the compounds of the present invention) therefore represents a unity-justifying feature, providing a unique contribution to the prior art.

In one embodiment the information relating to non-GSI effect leads to treatment of novel patient collectives or novel administration regimes, that were not possible without the information regarding the technical effect and/or mechanism of the molecules described herein. For example, patients who are particularly sensitive to gamma-secretase inhibitors during treatment can now also enjoy the benefits of notch inhibition-based treatment due to avoidance of direct gamma secretase inhibition.

With regard to the treatment of senescence-related ageing and associated illnesses, a preferred embodiment relates to senescence-related ageing that is characterised by the presence of senescence-associated secretory phenotype (SASP).

In one embodiment of the invention the SASP is an inflammatory disease. Such SASP inflammatory disease can in further embodiments of the invention be induced by secretion of proinflammatory cytokines, in particular IL-6 and IL-8. Measurements of SEAP-activity in culture medium or the use of ELISA tests for detecting cytokines, for example IL-6 and/or IL-8, may be applied to determine the presence of SASP inflammatory disease.

The invention relates to a pharmaceutical composition comprising one or more of the compounds disclosed herein and a pharmaceutically acceptable carrier substance.

The invention therefore also relates to a method for the treatment of a secretion-dependent disease, preferably cancer or senescence-related ageing, more preferably haematological cancer, colorectal cancer, cervical cancer, pancreatic cancer, breast cancer or lung cancer, chronic lymphocytic leukemia (CLL), esophageal cancer, glioma or colon cancer, more preferably lymphoma or leukemia, such as T-cell lymphoma, B-cell lymphoma, Hodgkin lymphoma or inflammatory disease, comprising administration of an effective amount of a pharmaceutical composition comprising one ore more of the compounds described herein to a subject in need of treatment.

Another aspect of the invention relates to the use of one or more of the compounds of the present invention as a lead structure for derivatization in the development of further biologically active compounds. Obvious derivatives of the compounds of the present invention, developed via further derivatization, are within the skilled persons reach and fall under the scope of the invention.

Additionally, the present invention relates to the in vitro use of the compounds described herein as inhibitors of the notch signalling pathway, as inhibitors of secretion or a secretion pathway and/or as an inhibitor of membrane traffic.

In a preferred embodiment the compound as described herein is characterised in that the compound has a molecular weight in the range of from 100 to 600 g/mol, preferably from 350 to 550 g/mol, a partition coefficient of log P≤6, preferably from ≥2 to ≤6, with a maximum of 2 hydrogen bridge donors and a maximum of 8 hydrogen bridge acceptors. The compounds identified through the screening process described herein all exhibit a variety of common physicochemical properties which make the compounds highly useful as pharmaceutical agents because they comply with Lipinski's Rule (the so-called Rule of Five) to a very large extent. This represents a significant advantage in medical application of the compounds, which was not expected in light of the prior art. The sum of structural common features results in a functional relationship that provides a common solution to the technical problem of the invention, namely the provision of notch inhibitors for the treatment of secretion dependent diseases that exhibit fewer side effects than the molecules previously known and/or applied in the art. The common physicochemical features therefore do not represent an arbitrary sum of features, but represent a common fingerprint of the claimed compounds, which advantageously enables and characterizes good in vivo suitability of the compounds.

DETAILED DESCRIPTION OF THE INVENTION

The invention relates to chemical compounds as inhibitors of the notch signalling pathway and secretion for the treatment of secretion-dependent disease, in addition to pharmaceutical compositions thereof and methods of treatment. "Secretion-dependent disease" relates to any disease where inhibition of secretion provides a therapeutic effect. Preferably, secretion-dependent diseases are selected from those diseases for which their etiology, pathogenesis, morphologic features and/or clinical manifestations are characterised by a dependence on cellular secretion and/or a secretory pathway, whereby a therapeutic effect in the treatment of said diseases is induced by the inhibition of cellular secretion. Secretion or a secretory pathway may be understood as any biological signalling pathway or mechanism involved in cellular secretion, preferably wherein the secretion or secretory pathway is related to, mediated and/or characterised by Wnt secretion, microRNA secretion, CCL2-secretion, ER transport and/or the Golgi apparatus.

The invention relates to chemical compounds for notch signalling pathway inhibition for the treatment of cancer or cancer-like disorders, such as a cell proliferative disorder. The terms "cancer", "cell proliferative disorder" or "cellular proliferative disorder" are used interchangeably and refer to any disorder in which the proliferative capabilities of the affected cells is different from the normal proliferative capabilities of unaffected cells. An example of a cell proliferative disorder is neoplasia. Malignant cells develop as a result of a multistep process. The term "malignant" may refer to a tumor or hematopoietic disease no longer under normal cellular growth control. The term "cancerous cell" as provided herein, includes a cell afflicted by any one of the cancerous conditions provided herein. The term "carcinoma" refers to a malignant new growth made up of epithelial cells tending to infiltrate surrounding tissues, and to give rise to metastases.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumour that is noncancerous, e.g. its cells do not proliferate or invade surrounding tissues.

The invention relates to chemical compounds as inhibitors of the notch signalling pathway and secretion for the treatment of senescence-related ageing, in addition to pharmaceutical compositions thereof and methods of treatment. "Senescence-related ageing" refers to senescence, meaning generally "to grow old", or "ageing". Biological aging is the process of accumulative changes to molecular and cellular structure that disrupts metabolism with the passage of time, resulting in deterioration and death. Senescence occurs both on the level of the whole organism (organismal senescence) as well as on the level of its individual cells (cellular senescence). The treatment of senescence is one aspect of the present invention and relates to slowing, reversing and/or inhibiting the ageing process from occurring. During aging the incidence of acute and chronic conditions such as neurological disorders, diabetes, degenerative arthritis, and even cancer rises within individuals, so that aging has been termed the substrate on which age-associated diseases grow. The invention therefore relates to prophylactic methods for preventing these diseases by reducing ageing through secretion inhibition.

The molecular pathways underlying aging are not well understood as large individual heterogeneity of the biological aging process is observed. These inter-individual differences are proposed to derive from accumulation of stochastic damage that is counteracted by genetically encoded and environmentally regulated repair systems. At the level of molecules repair works by enzymatic systems while on the cellular level it works by replication and differentiation to maintain tissue homeostasis. However, the replicative potential of somatic and adult stem cells is limited by cellular senescence and recent evidence shows that counteracting senescence or removing senescent cells delays the onset of age-associated pathologies. The present invention therefore provides means for the treatment of ageing as such, in addition to age-related medical conditions.

In particular, the compounds of the present invention may be applied in the treatment of inflammation related diseases caused by the senescence-associated secretory phenotype (SASP). SASP has been reviewed in the literature and the diseases associated with said conditions are known to a skilled person (see for example Davalos et al., Cancer Metastasis Rev. 2010 June; 29(2): 273-283). Several lines of evidence suggest that tumor suppressor mechanisms can be doubled-edged swords. Such mechanisms suppress the development of cancer early in life; but they can also result in altered tissue structure, organization, and homeostasis. These tissue changes can drive phenotypes and pathologies associated with aging, including, late-life cancer. Cellular senescence can be induced by potentially oncogenic stimuli. The senescence response often depends on two potent tumor suppressor pathways: that governed by the p53 protein and that governed by the pRB and p16INK4a proteins. Senescent cells can be found in pre-malignant lesions in mice and humans, and in mouse models, the senescence response prevents malignant progression. Consistent with a role in aging, senescent cells accumulate with age in many rodent, non-human primate, and human tissues. Moreover, they are found at sites of age-related pathology, including degenerative disorders such as osteoarthritis and atherosclerosis and hyperproliferative lesions such as benign prostatic hyperplasia and melanocytic naevi. Cell culture and mouse xenograft studies support the idea that senescent cells secrete factors that can disrupt tissue structure and function and promote cancer progression. Importantly, the SASP may be the major reason for the deleterious side of the senescence response.

Cellular senescence is accompanied by a striking increase in the secreted levels of >40 factors involved in intercellular signalling. The SASP has many of the paracrine effects one would expect from a pro-inflammatory stimulus, which can be deleterious if left unchecked. The SASP includes several families of soluble and insoluble factors. These factors can affect surrounding cells by activating various cell surface receptors and corresponding signal transduction pathways that may lead to multiple pathologies, including cancer. SASP factors can globally be divided into the following major categories: soluble signaling factors (interleukins, chemokines, and growth factors), secreted proteases, and secreted insoluble components. SASP proteases can have three major effects: shedding of membrane-associated proteins resulting in soluble versions of membrane-bound receptors, cleavage/degradation of signaling molecules, and degradation or processing of the extracellular matrix.

The terms "γ-secretase" and gamma-secretase are used interchangeably.

In the present invention "treatment" or "therapy" generally means to obtain a desired pharmacological effect and/or physiological effect. The effect may be prophylactic in view of completely or partially preventing a disease and/or a symptom, or may be therapeutic in view of partially or completely curing a disease and/or adverse effect of the disease. In the present specification, "therapy" includes arbitrary treatments of diseases or conditions in mammals, in particular, humans, for example, the following treatments (a) to (c): (a) Prevention of onset of a disease, condition or symptom in a patient; (b) Inhibition of a symptom of a condition, that is, prevention of progression of the symptom; (c) Amelioration of a symptom of a condition, that is, induction of regression of the disease or symptom.

The term "pharmaceutical composition" refers to a combination of the agent as described herein with a pharmaceutically acceptable carrier. The phrase "pharmaceutically-acceptable" refers to molecular entities and compositions that do not produce a severe allergic or similar untoward reaction when administered to a human. As used herein, "carrier" or "carrier substance" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Supplementary active ingredients can also be incorporated into the compositions. A pharmaceutical composition of the present invention can include pharmaceutically acceptable salts of the components therein. The pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions. Tablets contain the active ingredient in admixture with non-toxic pharmaceutically acceptable excipients which are suitable for the manufacture of tablets. The tablets may be uncoated or they may be coated by known techniques to delay disintegration and absorption in the gastrointestinal tract and thereby provide a sustained action over a longer period.

Dosage levels of the order of from about 0.01 mg to about 500 mg per kilogram of body weight per day are useful in the treatment of the indicated conditions. For example, a cancer may be effectively treated by the administration of from about 0.01 to 50 mg of the inventive molecule per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 500 mg of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. The invention relates also to a process or a method for the treatment of the mentioned pathological conditions. The compounds of the present invention can be administered prophylactically or therapeutically, preferably in an amount that is effective against the mentioned disorders, to a warm-blooded animal, for example a human, requiring such treatment, the compounds preferably being used in the form of pharmaceutical compositions.

In one aspect, the invention provides a method of preventing, treating, and/or managing cancer to a patient in need thereof, the method comprising administering a prophylactically effective regimen or a therapeutically effective regimen, the regimen comprising administering to the patient a compound of the invention, or a pharmaceutically acceptable salt thereof, wherein the patient has been diagnosed with cancer, and wherein said cancer is a haematological cancer, colorectal cancer, cervical cancer, pancreatic cancer, breast cancer or lung cancer. In some embodiments, a patient may receive therapy for the treatment and/or management of the cancer before the administration of the therapeutically effective regimen of the compound of the invention, or a pharmaceutically acceptable salt thereof. Non-limiting examples of such a therapy include chemotherapy, radioimmunotherapy, toxin therapy, prodrug-activating enzyme therapy, antibody therapy, surgical therapy, immunotherapy, radiation therapy, targeted therapy (i.e. therapy directed toward a specific target or pathway, e.g. tyrosine kinase, etc.), and any combination thereof. In some embodiments, the patient has not previously received a therapy for the treatment and/or management of the cancer. In a specific embodiment, the hematologic cancer is lymphoma or leukemia, or a T-cell lymphoma, B-cell lymphoma or Hodgkin lymphoma.

In another aspect, the invention provides a method of preventing, treating, and/or managing a solid tumor in a patient, the method comprising administering to a patient in need thereof a prophylactically effective regimen or a therapeutically effective regimen, the regimen comprising administering to the patient a compound of the invention, or a pharmaceutically acceptable salt thereof, wherein the patient has been diagnosed with a solid tumor. In particular embodiments of this aspect, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney-cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, or retinoblastoma.

The invention is therefore based on a novel type of secretion inhibitor, FLI-06 and derivatives thereof. In contrast to other secretion inhibitors, no gross ER stress is induced. FLI-06 and its derivatives represent useful medicaments for inhibiting or reducing secretion without inducing ER-stress mediated apoptosis. The following analyses have been conducted or are appropriate for further analysis of FLI-06 and its derivatives, in order to identify and support the effect of these compounds in interfering with SASP to delay tissue dysfunction and extend healthy lifespan:

FLI-06 is a secretion inhibitor with an $EC_{50}$ of 2.3 μM. We performed initial structure-activity relationship (SAR) studies that will be extended in the current proposal to develop inhibitors working in the nanomolar range. FLI-06 and derivatives will be tested for their efficacy in human fibroblasts where senescence is induced chemically or by repetitive passaging. Inhibition of SASP can be measured with ELISAs for IL-6 and -8 and by measuring secreted alkaline phosphatase (SEAP) (Gu, L. & Kitamura, M. Sensitive detection and monitoring of senescence-associated secretory phenotype by SASP-RAP assay. PLoS One 7, e52305, (2012)). Cellular toxicity, proliferation as well as autophagy can be assayed. To study the role of SASP in brain ageing, promising compounds can be analyzed whether they can reverse defects in learning and memory in brain slices of ageing models like the Klotho mouse and whether dynamics of UPS and lifetime of synaptic proteins are changed. Promising compounds can also be tested for life-extending effects in *C. elegans*. Lead substances are being further optimized for use in vertebrate animal trials.

Novel SASP inhibitors such as those described herein can also further be assayed or screened with senescent human fibroblasts that stably express SEAP. Hits can be validated in secondary screens involving serial dilutions and $IC_{50}$ determinations. Hits can be tested whether they affect general secretion in non-senescent and senescent cells. Promising hits can be analyzed for their mode of action, specificity and toxicity.

Additionally, genome-wide siRNA screens can be carried out to identify novel targets involved in senescence, SASP and autophagy. Multi-color human fibroblast cell lines have been generated that stably expresses fluorescent-protein tagged markers for the Golgi (GalT, the Golgi is enlarged and dispersed in senescence), lysosomes (Lamp1, lysosomes are enlarged in number and size in senescence) and autophagosomes (LC3, number is increased in senescence). For automatic identification of cells, the nuclei can be labeled with the far-red nuclear dye To-Pro-3 (Invitrogen). Conditions may be optimized for transfection and screening of chemically-induced senescent multi-color cells in 384-well format. Read-out parameters can include grade of dispersal of the Golgi, number and size of lysosomes, number and size of autophagosomes. Genome-wide siRNA libraries (Dharmacon) can additionally be screened, and phenotypical changes in the three markers analyzed. Hits can be classified: Hits affecting the senescent secretory pathway on all levels, hits affecting only one or two of the read-out parameters, hits affecting autophagy with or without affecting Golgi or lysosomes, and more. Candidates validated in secondary screens can be tested in detail, for example whether the morphological change they induce indeed affects SASP, whether it is causative or correlative for SASP and/or senescence, whether the affected gene was associated to ageing before.

The experimental methods described above can therefore be used to provide further information on the derivatives disclosed herein and related compounds falling under the general formulas disclosed herein. Furthermore, additional compounds and genetic factors involved in senescence and the mechanism of action of the compounds as described herein may be identified by the experimental approaches described herein.

FIGURES

The figures provided herein represent examples of particular embodiments of the invention and are not intended to limit the scope of the invention. The figures are to be considered as providing a further description of possible and potentially preferred embodiments that enhance the technical support of one or more non-limiting embodiments.

Short description of the figures:

FIG. 1: Chemical interference of Notch trafficking/processing is amenable to automated microscopy.

Figure 2:
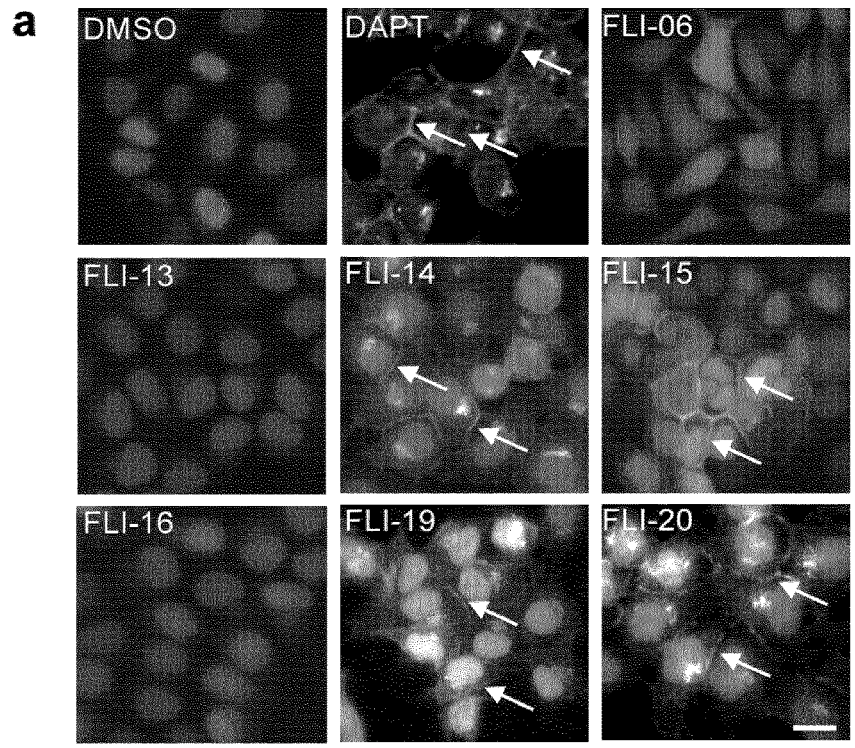
Figure 2:
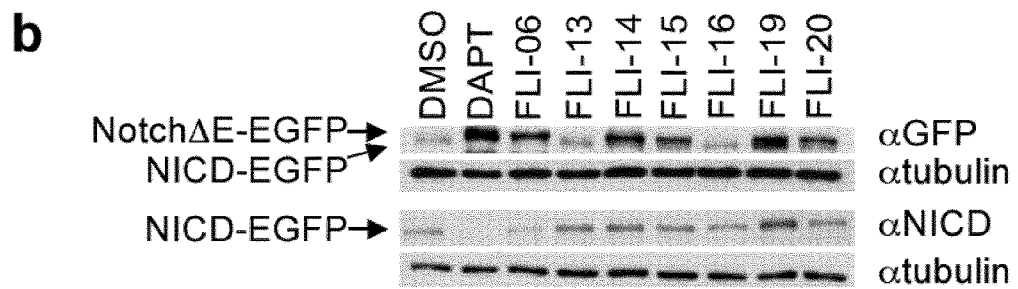
Figure 2:
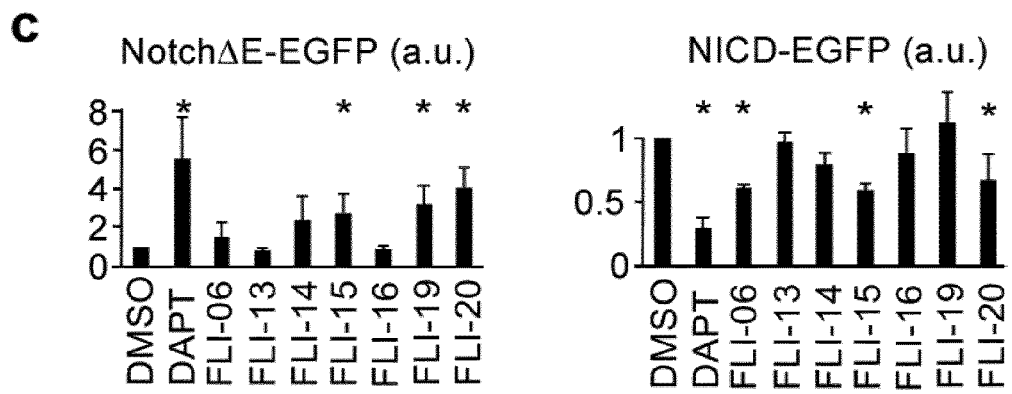
Figure 2:
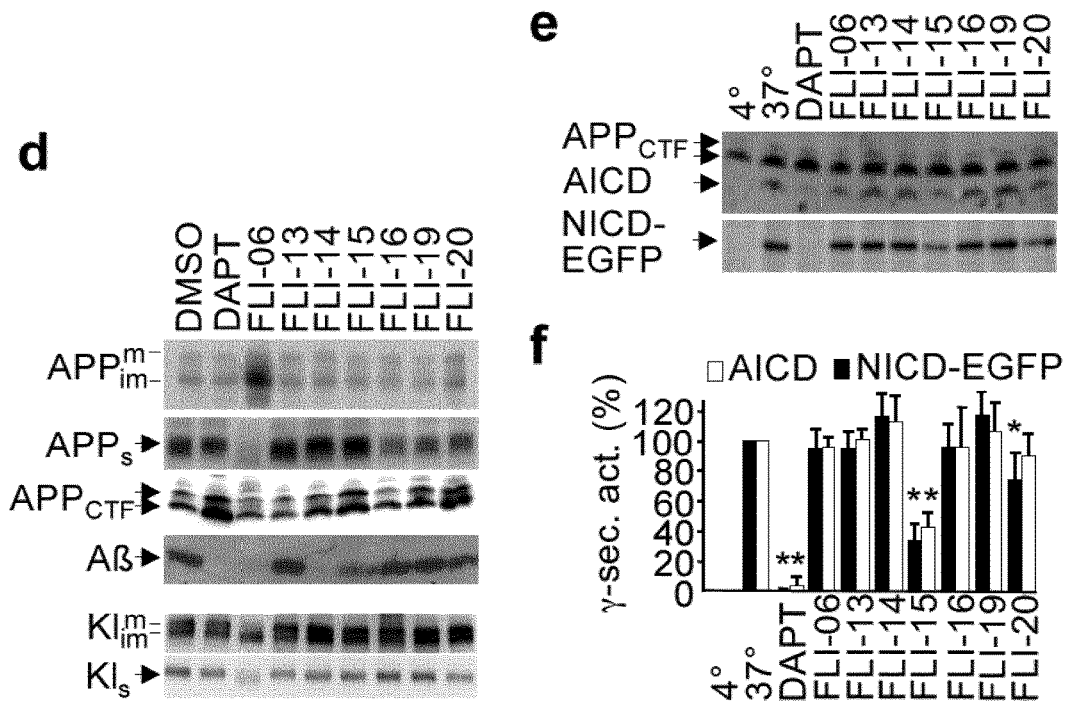

FIG. 2: Selected compounds from final hit list show distinct phenotypes.

Figure 3:
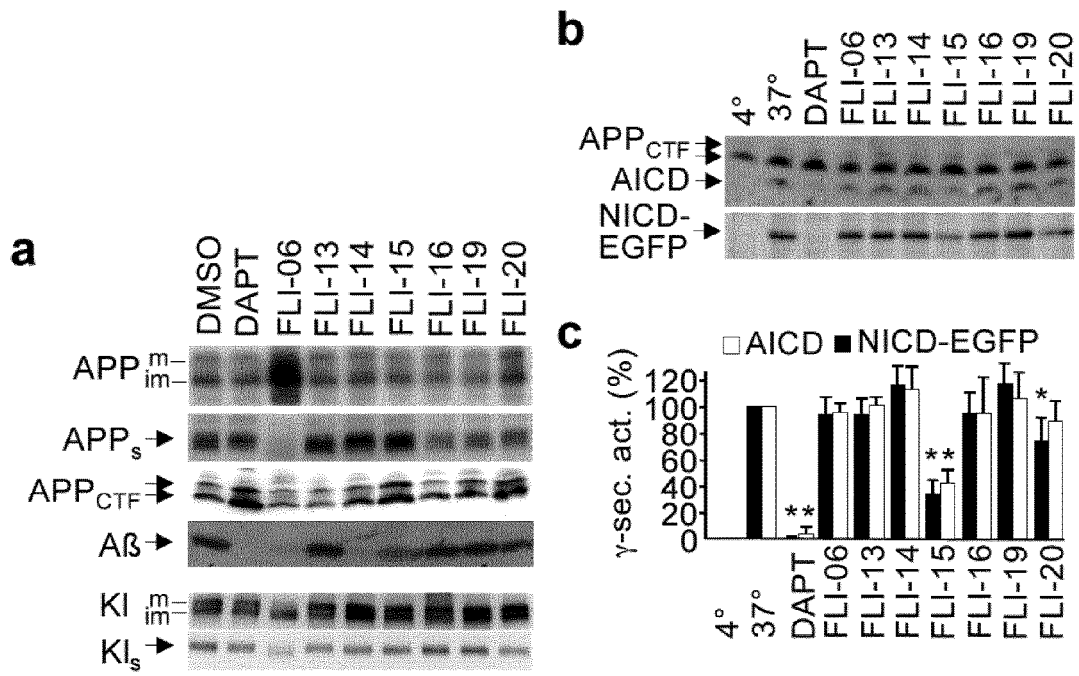

FIG. 3: Effect of compounds on NotchΔE-EGFP, APP and Klotho trafficking and processing.

Figure 4:
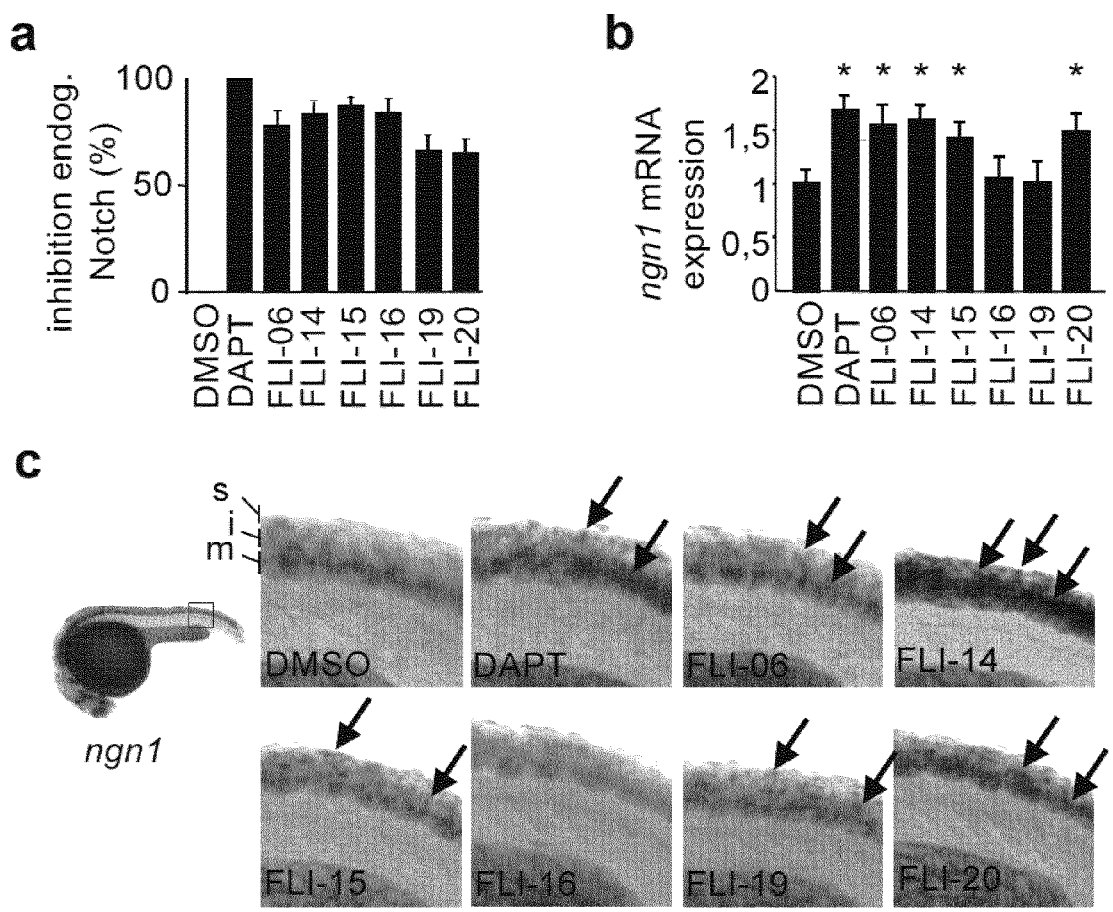

FIG. 4: Selected compounds inhibit endogenous Notch signaling.

Figure 5:
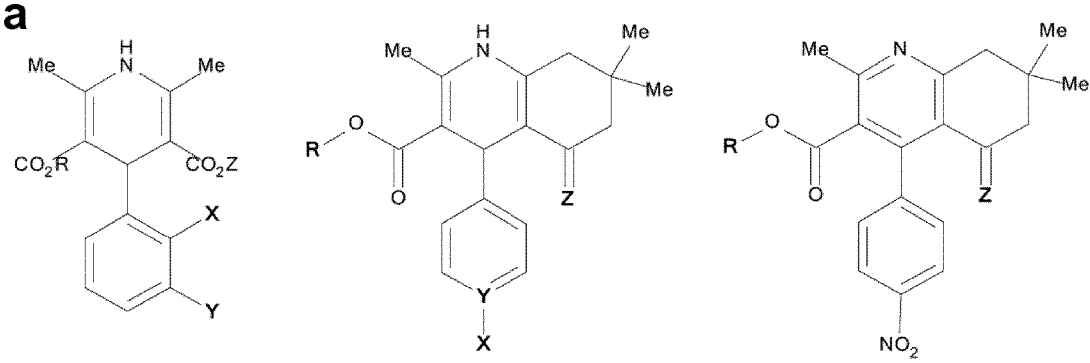
Figure 5:
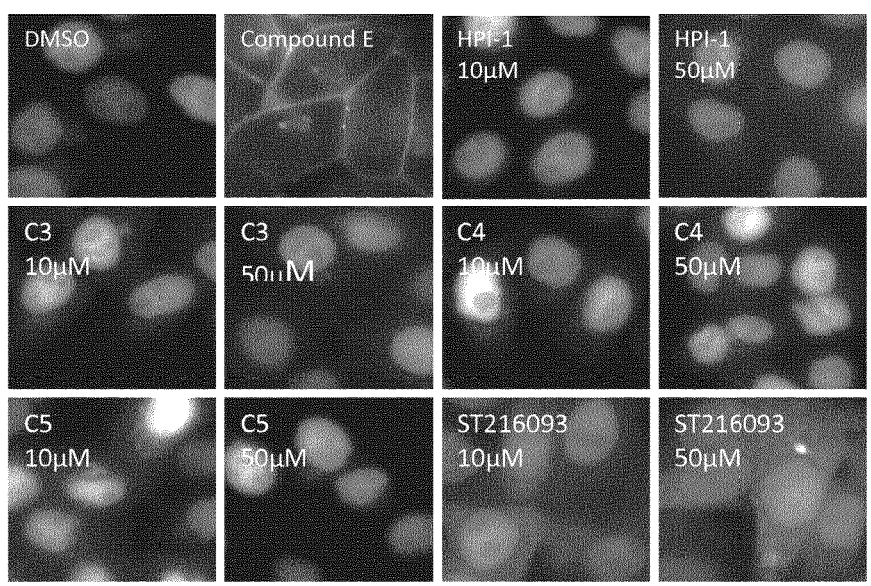
Figure 5:
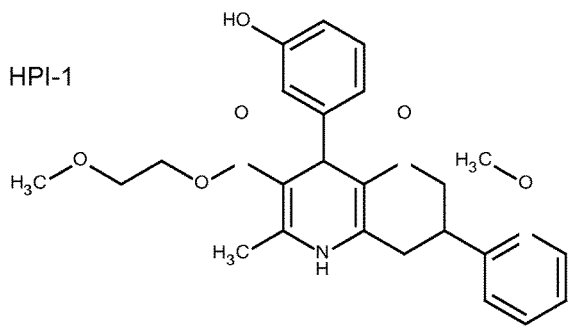
Figure 5:
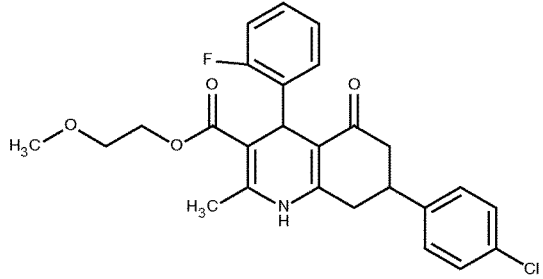
Figure 5:
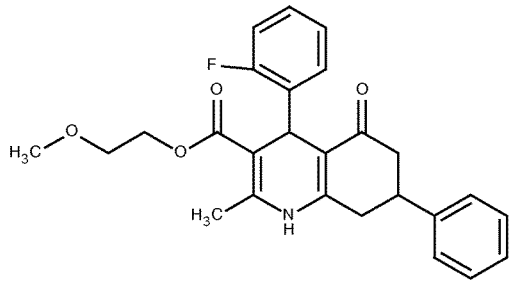
Figure 5:
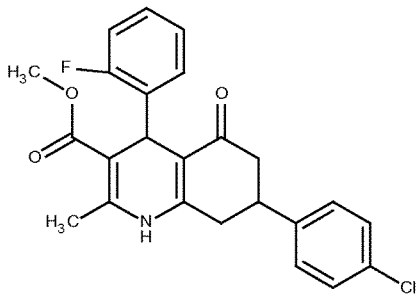
Figure 5:
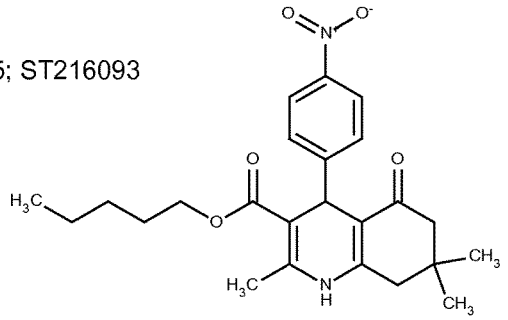
Figure 5:
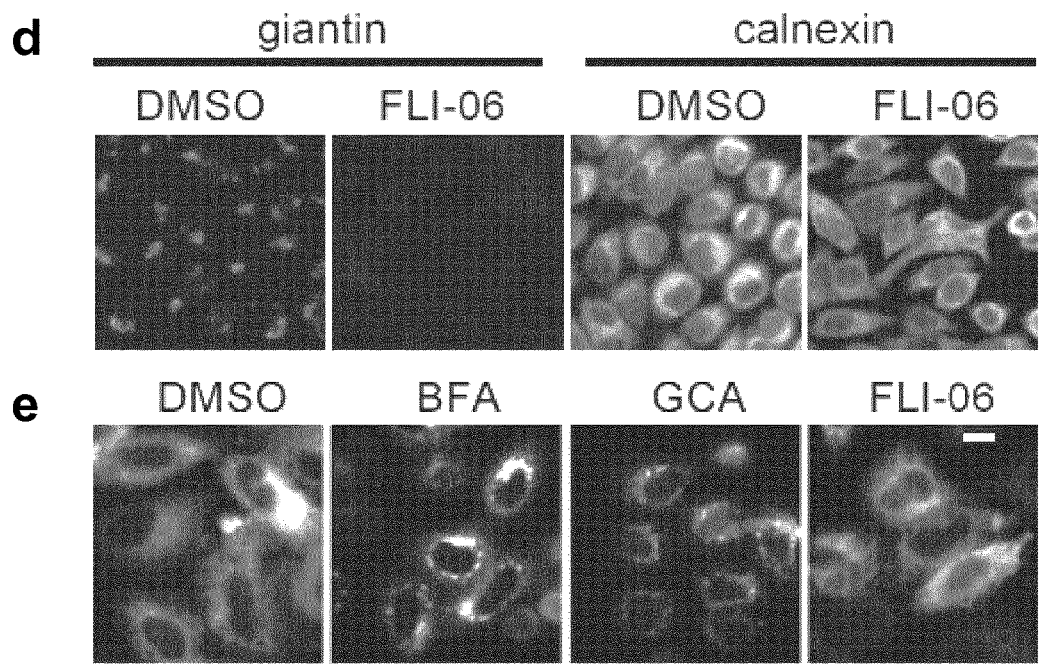

FIG. 5: The dihydropyridine FLI-06 disrupts the Golgi by mechanisms different from BFA or GCA.

Figure 6:
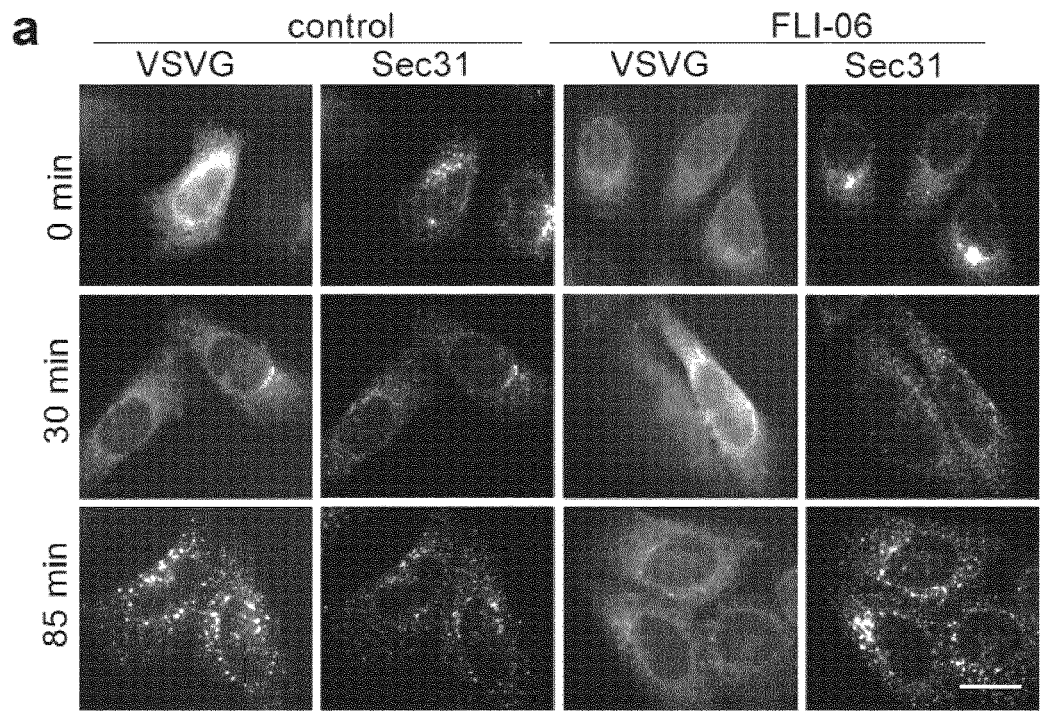
Figure 6:
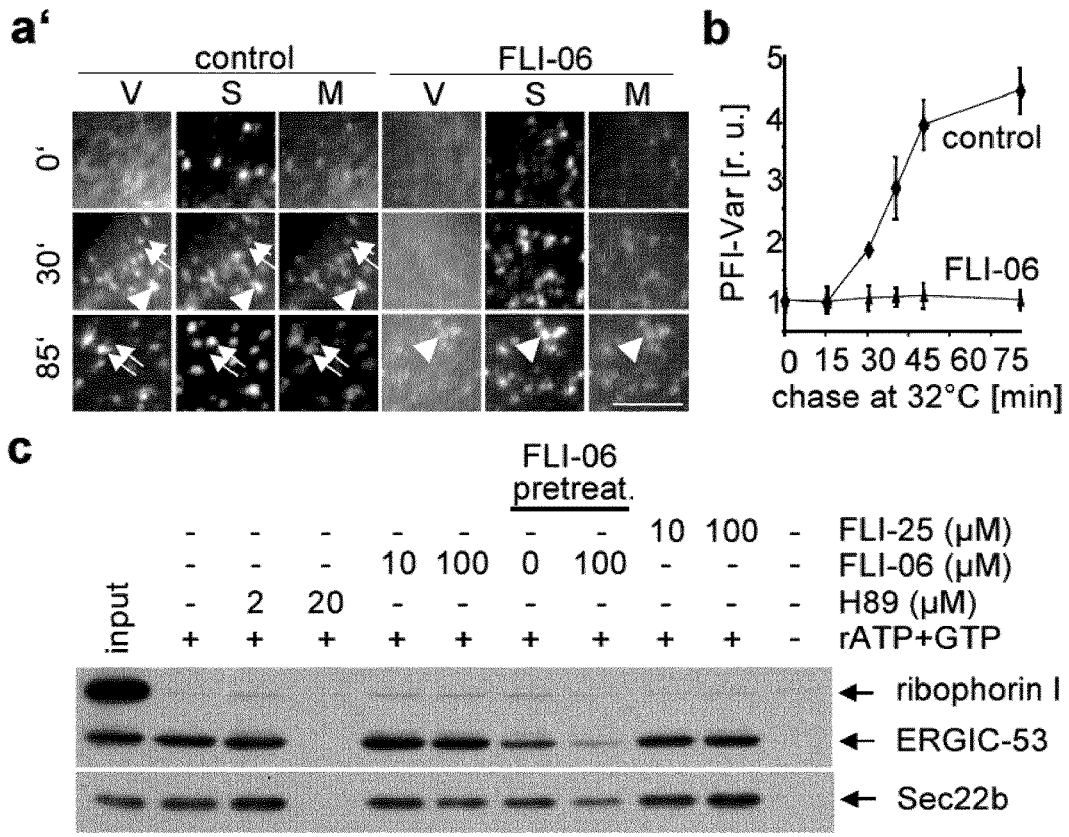

FIG. 6: FLI-06 affects recruitment of cargo to ER exit sites.

Figure 7:
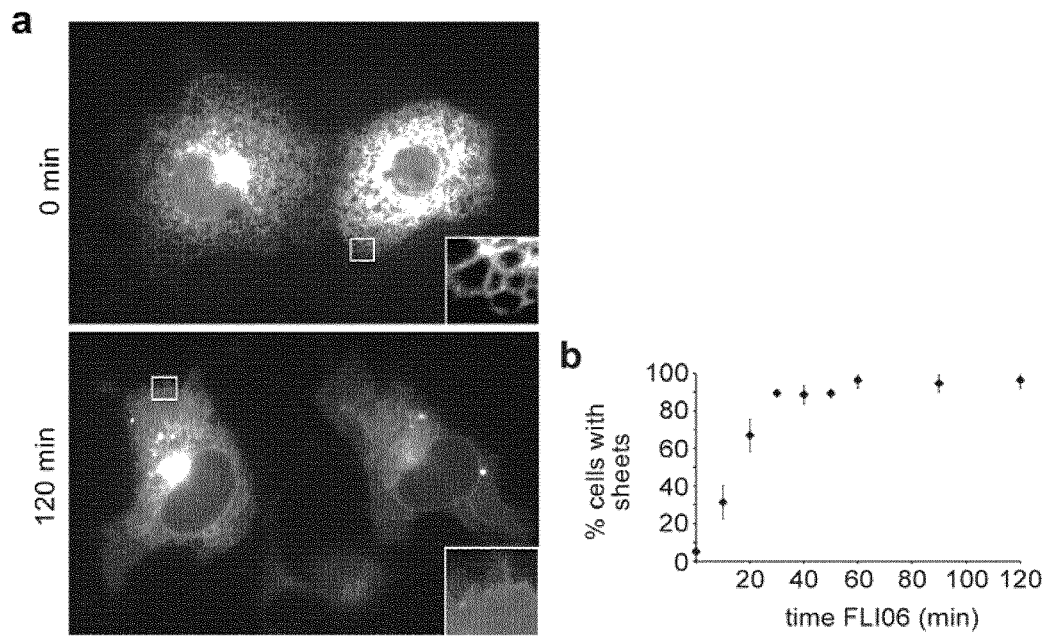

FIG. 7: FLI-06 induces ER sheet formation.

Figure 8:
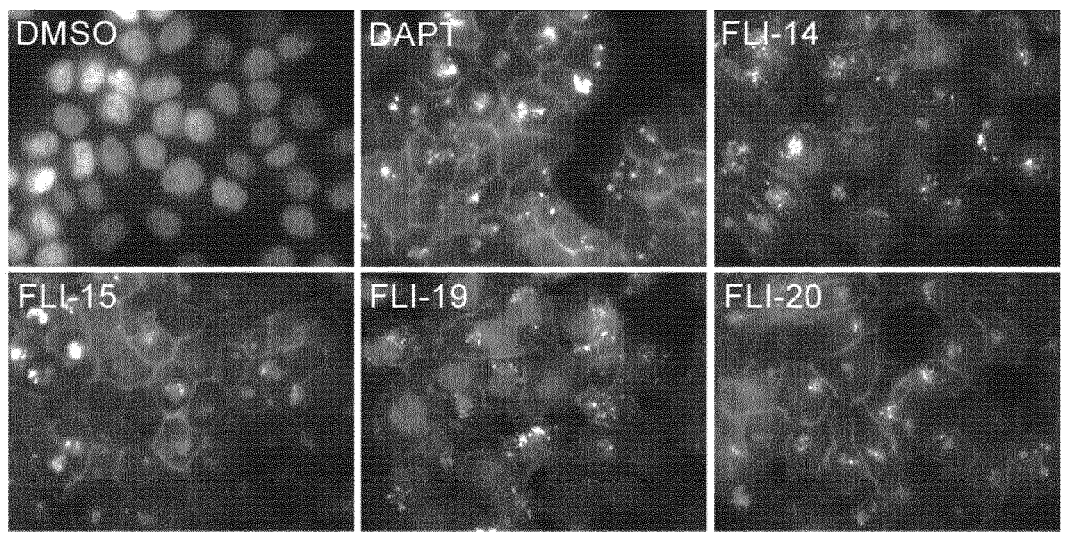

FIG. 8: DAPT-like phenotype of FLI-14, -15, -19 and -20 at 50 µM.

Figure 9:
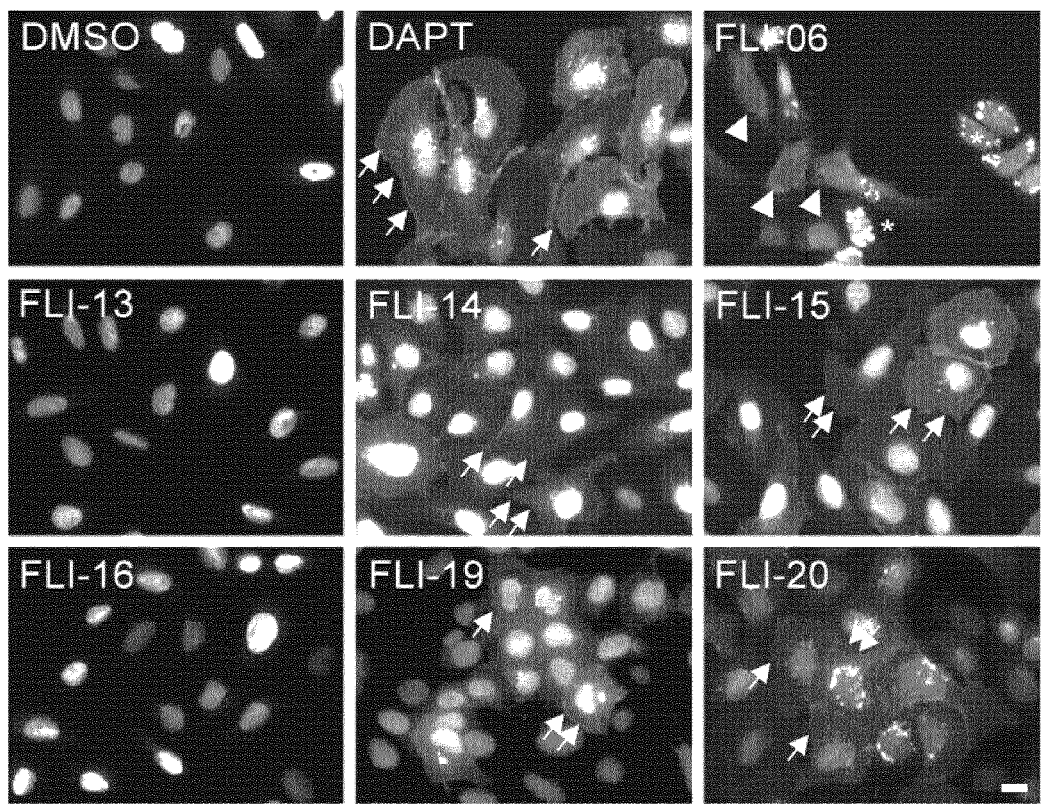

FIG. 9: Compound effects are not cell-type specific.

Figure 10:
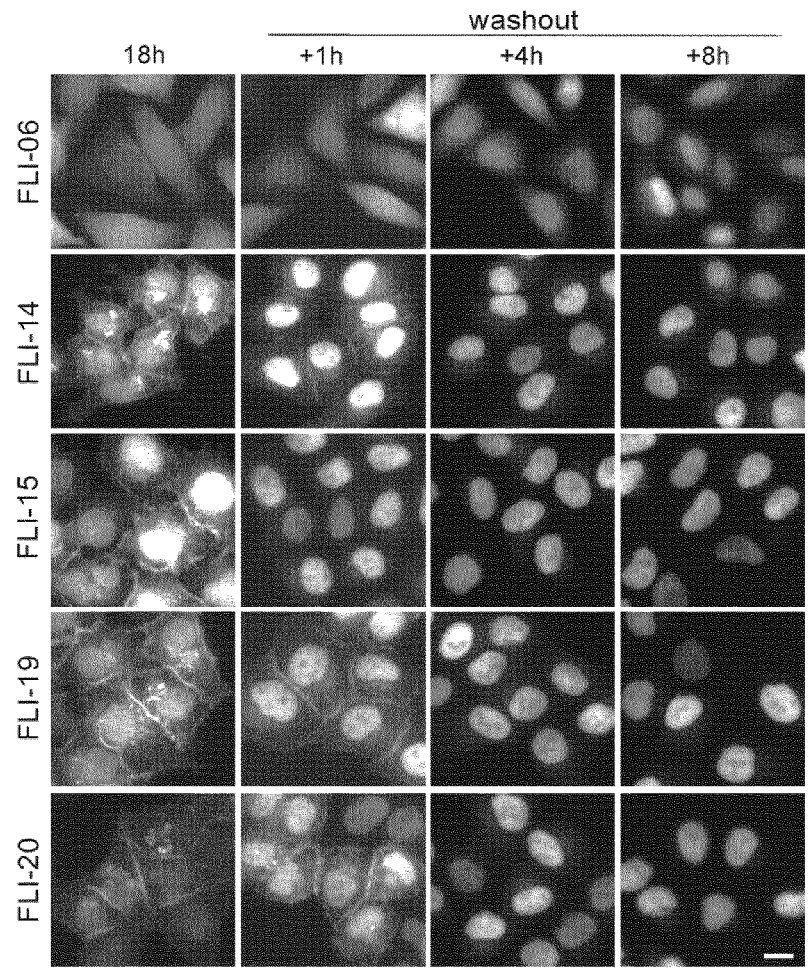

FIG. 10: Phenotypes of Notch inhibitors are fully reversible.

Figure 11:
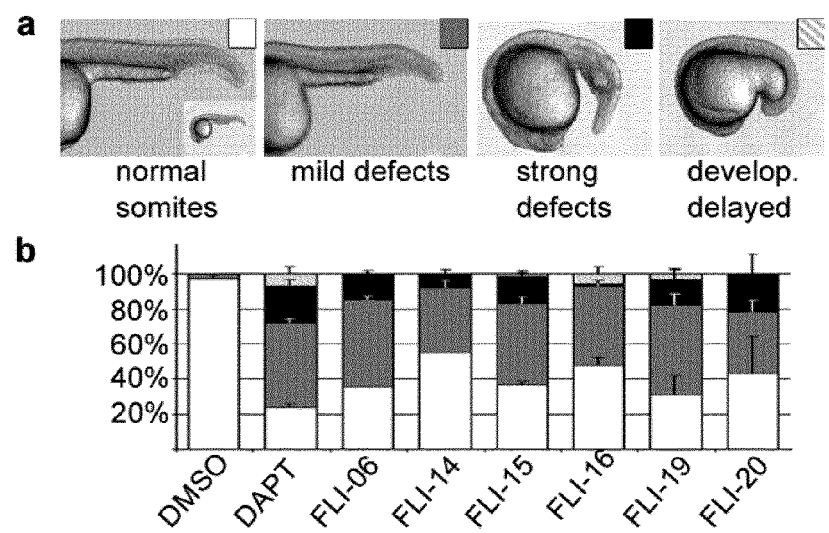
Figure 11:
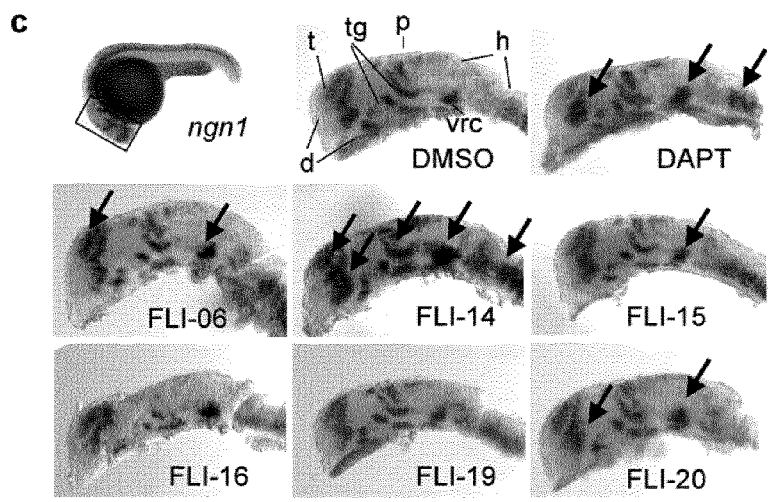

FIG. 11: Selected compounds affect somite formation and neurogenesis in vivo in zebrafish embryos.

Figure 12:
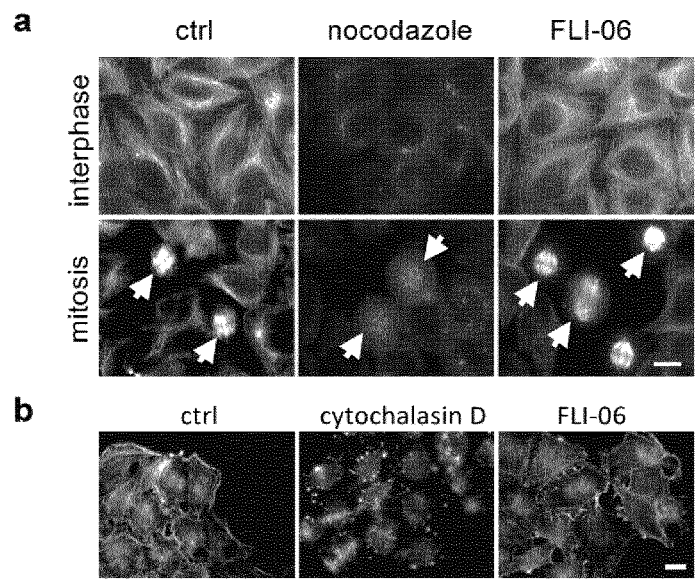

FIG. 12: FLI-06 disrupts the Golgi not via depolymerizing microtubuli or actin.

Figure 13:
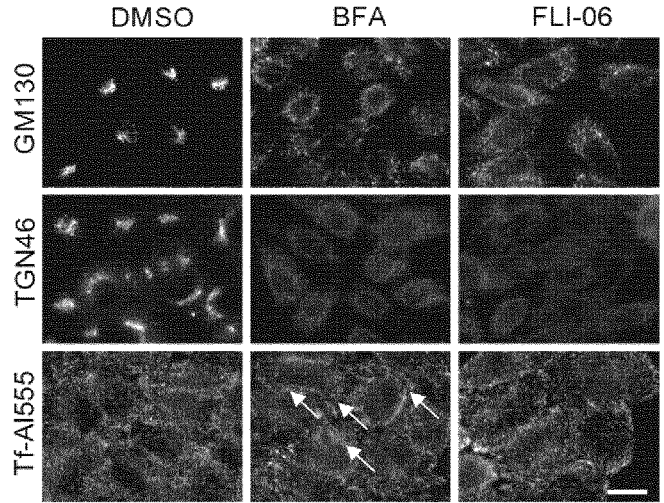

FIG. 13: FLI-06 causes dispersal of early Golgi and TGN, but no tubulation of endosomes.

Figure 14:
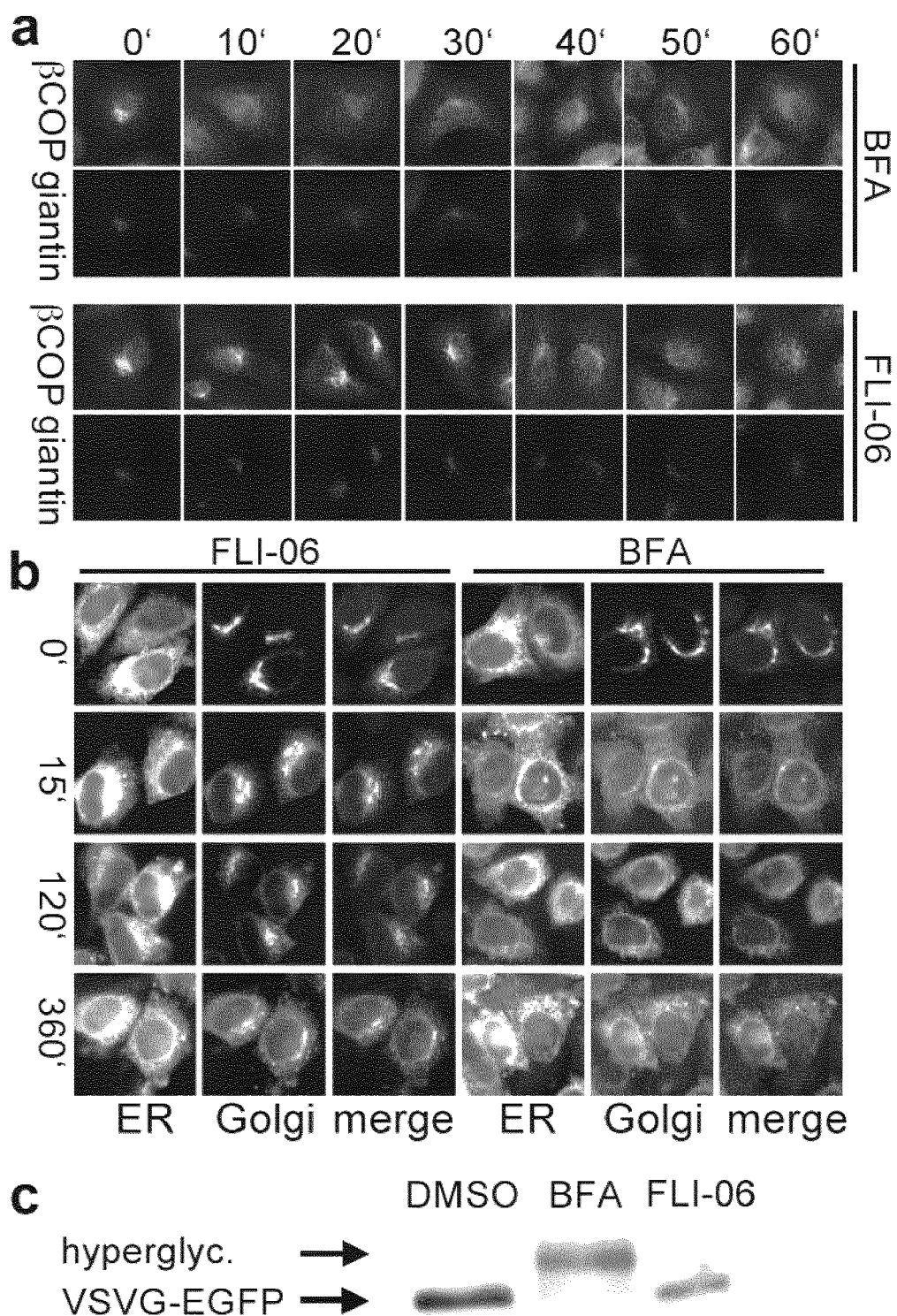

FIG. 14: FLI-06 acts different from BFA.

Figure 15:
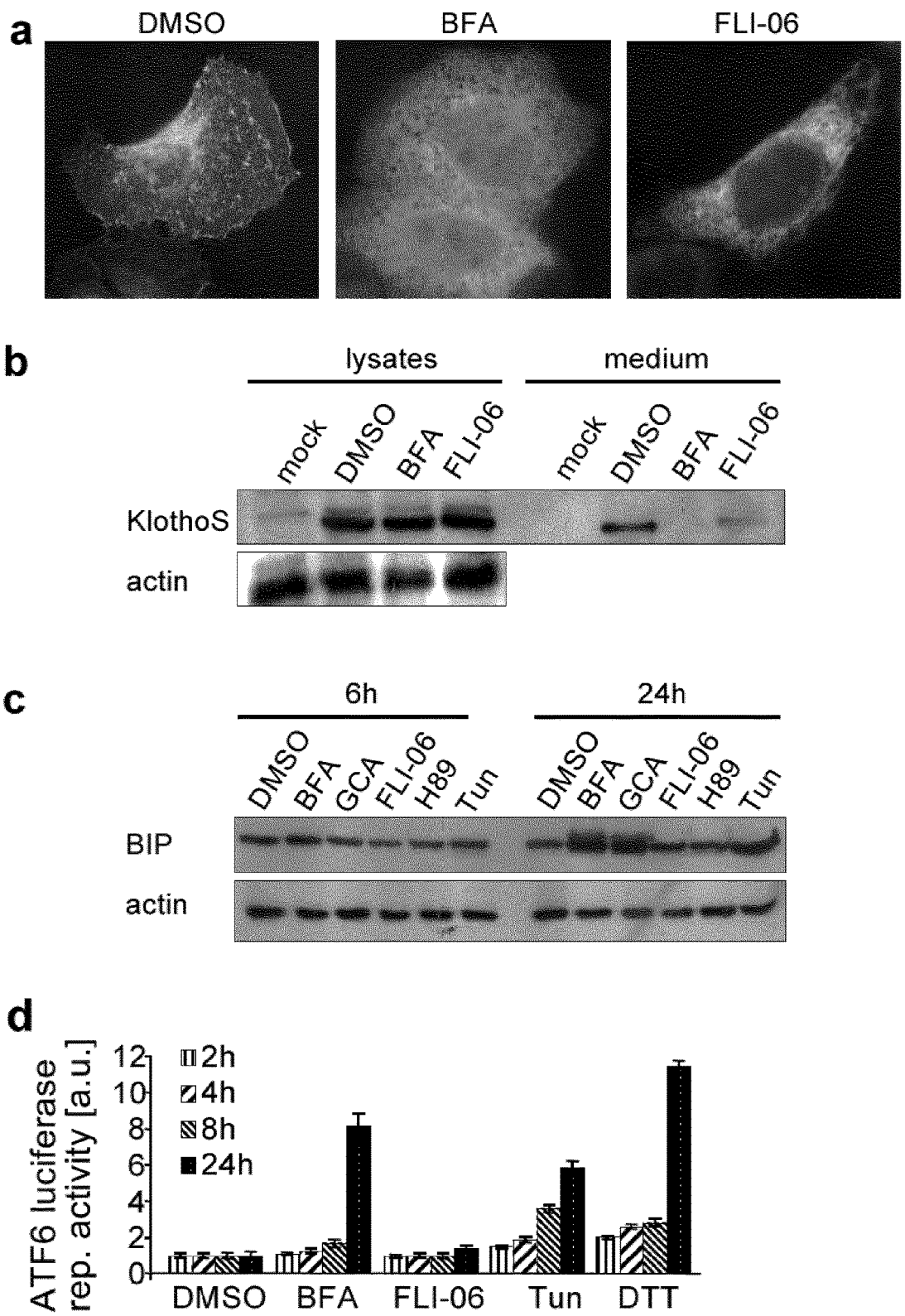

FIG. 15: FLI-06 inhibits transport of GPI-anchored and soluble proteins and does not cause ER stress.

Figure 16:
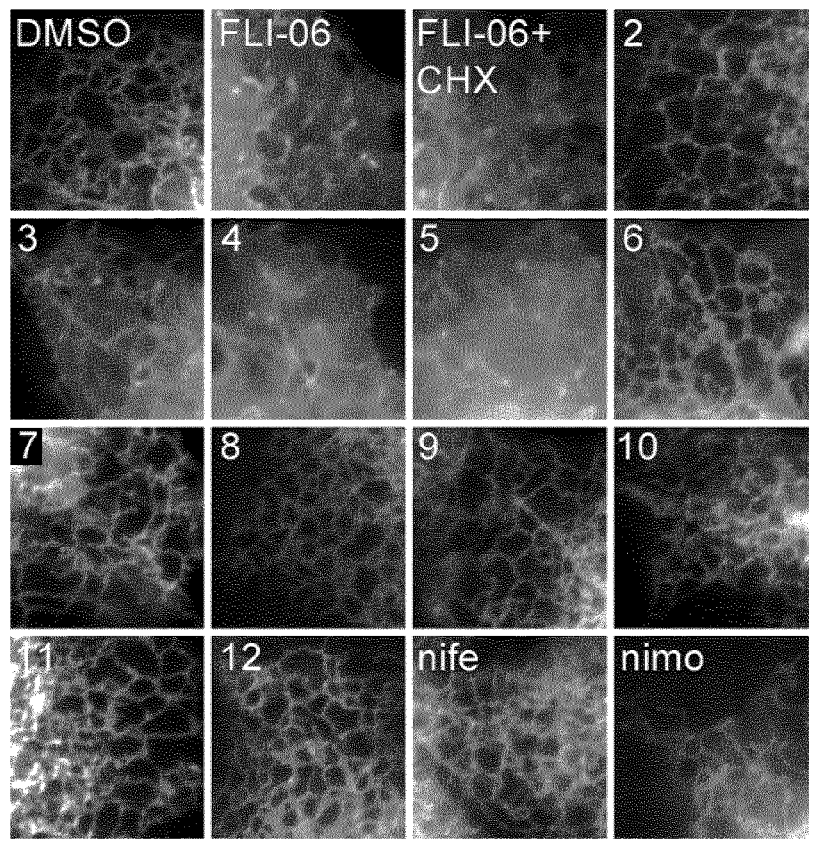

FIG. 16: Only ER exit inhibitors convert ER tubules to sheets.

Figure 17:
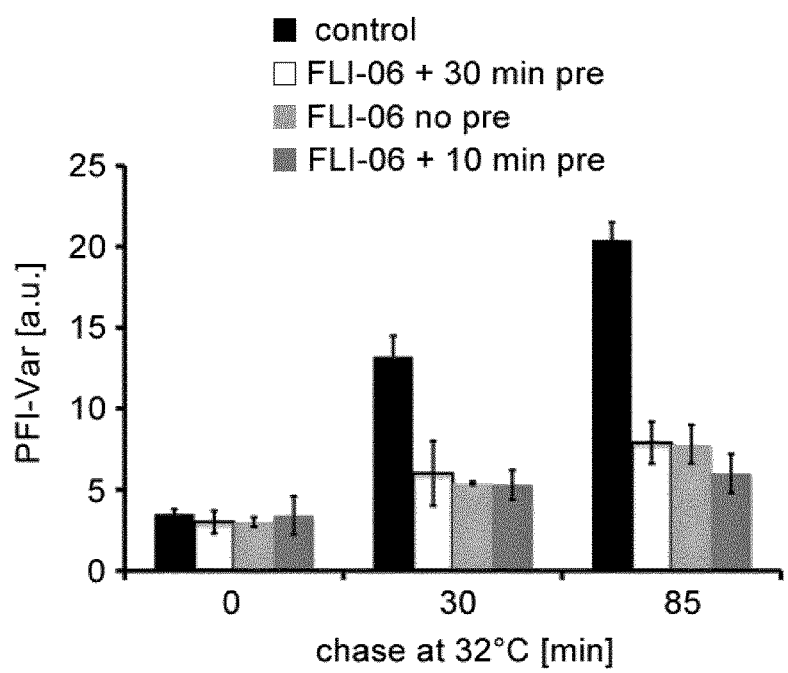

FIG. 17: FLI-06 blocks ER-export instantaneously.

Figure 18:
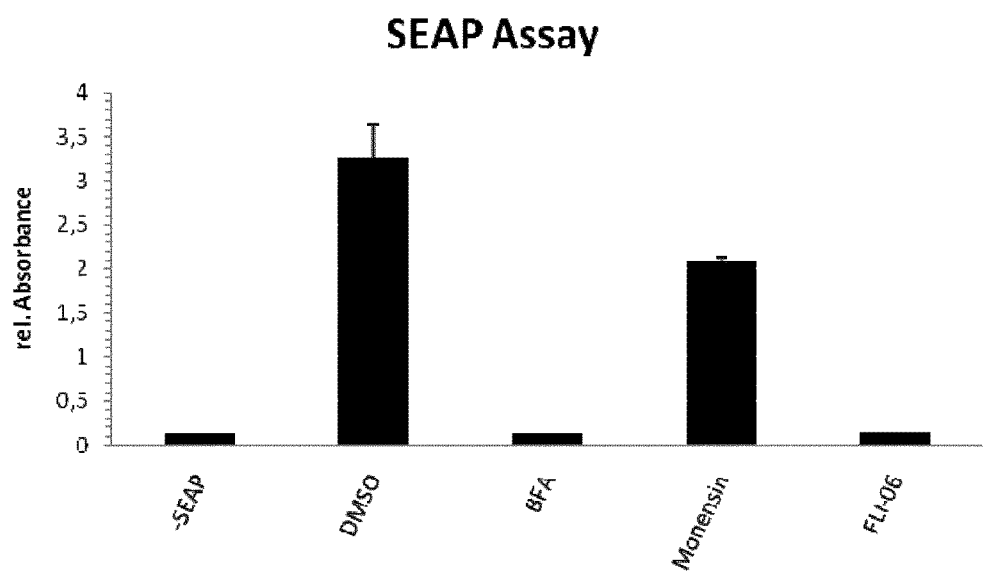
Figure 18:
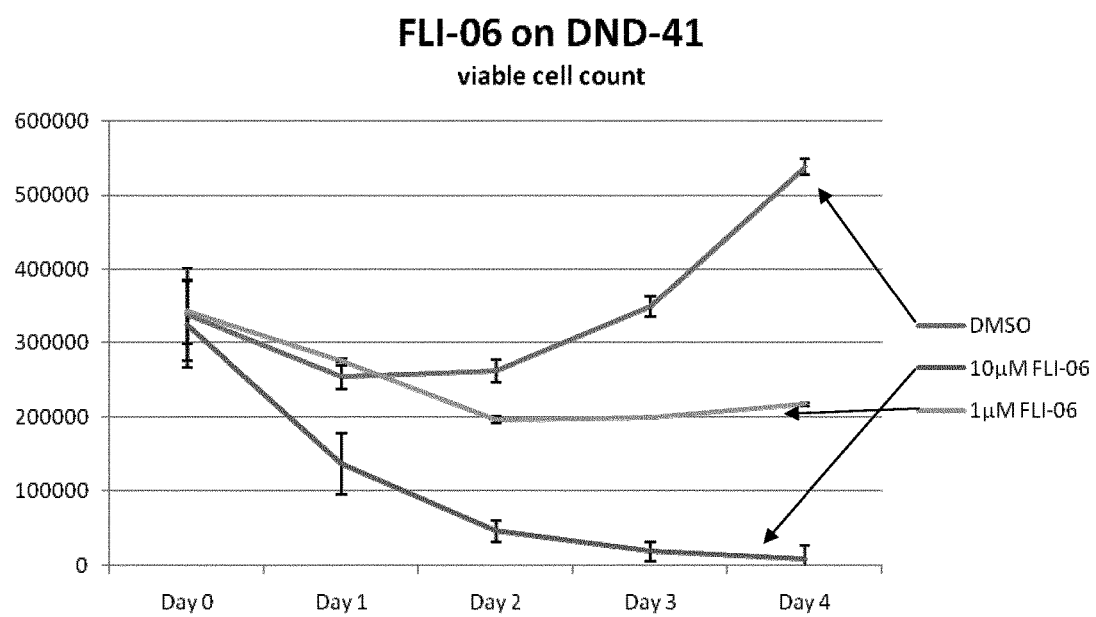

FIG. 18: FLI-06 inhibits secretion of secreted alkaline phosphates; FLI-06 kills cancerous, Notch dependent T-cells FIG. 19: Molecular structure of FLI-06. Thermal Ellipsoids are displayed at 40% probability level.

Figure 20:
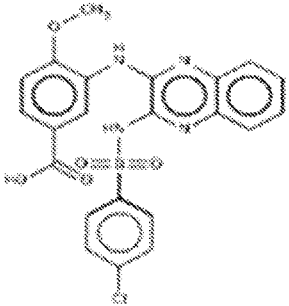

FIG. 20: Top 7 hit list of compounds.

Detailed description of the figures:

FIG. 1: Chemical interference of Notch trafficking/processing is amenable to automated microscopy. Scheme of the membrane bound reporter NotchΔE-EGFP (a) and its cellular trafficking (b). NotchΔE-EGFP is synthesized in the ER and transported through the Golgi to the plasma membrane (PM). At the PM γ-secretase cleavage releases NICD-EGFP, which is then translocated to the nucleus. c) Scheme of automated image acquisition and quantitation. Fixed HeLa-NotchΔE-EGFP cells were stained with DAPI and imaged by automated microscopy. A nuclear mask and a ring around the nucleus was created and used for determination of nuc, enuc and enuc/nuc ratio of fluorescence intensities. d) HeLa-NotchΔE-EGFP cells were incubated with or without DAPT, fixed and imaged by fluorescence microscopy. e) Quantitation of DAPT dose-dependent enuc accumulation of NotchΔE-EGFP and time-dependent reduction of nuclear NICD-EGFP after DAPT treatment. f, g) HeLa-NotchΔE-EGFP cells were incubated with increasing amounts of monensin, fixed after 6 h and analyzed by automated microscopy. f) Example image of cells treated with DMSO or monensin (5 µM). Accumulated fluorescence in the Golgi is marked by arrows. g) Quantitation of >100 cells±SE. Displayed is the nuc/enuc ratio. h, i) HeLa-NotchΔE-EGFP cells were incubated in the presence or absence of MG132 (1 µM) for 16 h, fixed and processed for fluorescence microscopy (h). i) Quantitation of nuclear fluorescence of >250 cells±SE. All y-axes display fluorescence intensity in arbitrary units. Scalebar 10 µm. j) Summary of the screen.

FIG. 2: Selected compounds from final hit list show distinct phenotypes. Hela NotchΔE-EGFP cells were incubated with compounds (10 µM) for 18 h, fixed and analyzed by fluorescence microscopy (a) or lysed, separated by SDS-PAGE, blotted and probed with antibodies against GFP and NICD (b). Tubulin served as loading control. c) Quantitation of NotchΔE-EGFP accumulation and NICD production from 3-4 experiments as shown in (b). Displayed is the SD with asterisks marking p<0.05. Arrows, plasma membrane; scalebar, 10 µm.

FIG. 3: Effect of compounds on NotchΔE-EGFP, APP and Klotho trafficking and processing. a) HEK293 stably expressing $APP_{swe}$ or Klotho (Kl) were incubated with DAPT or compounds (10 µM) for 16 h. Media were collected, cells lysed and both assayed by Western blotting using indicated antibodies. m, mature; im, immature; s, shedded ectodomain; CTF, C-terminal fragment. b) Membranes from HeLa-NotchΔE-EGFP and APPswe cells were isolated and subjected to a γ-secretase in vitro assay in the presence of DAPT or compounds as indicated. NICD and AICD were detected by Western Blotting using antibodies against the C-terminus of APP (top) or antibodies specific for NICD (bottom). c) Quantitation from 5 independent experiments. Displayed is the SD with asterisks marking p<0.01.

FIG. 4: Selected compounds inhibit endogenous Notch signaling. a) C2C12 cells were transfected with the Notch ligand Delta and a luciferase-based Notch-reporter. Cells were incubated with DAPT or 10 µM of the indicated compounds (50 µM in case of FLI-15 and -20) and after 16 h a luciferase assay was performed. Values from DMSO-treated cells were set to 0% inhibition, from DAFT-treated cells to 100% inhibition and the other compounds related to that. b) and c) Compounds (50 µM) were added to dechorionated stage 4 hpf zebrafish embryos and the effects analyzed after 24 h. b) qPCR with primers specific for ngn1. Changes in relative gene expression levels (fold change) relative to the expression levels in DMSO controls are represented as the mean+/−SD, asterisks indicate p<0.01. Each measurement was taken from two independent samples. Each reaction was measured in triplicate. Changes in the relative expression of ngn1 were standardized to the expression of the housekeeping gene ef1a at 20 hpf. c) ISH with riboprobes specific for ngn1 was performed on dechorionated stage 4 hpf zebrafish embryos. Anterior is to the left, dorsal to the top. Magnifications of the somite region (small box) are shown. Arrows indicate larger ngn1 clusters or stronger ngn1 staining. s, sensory neurons; i, intermediate neurons; m, motor neurons.

FIG. 5: The dihydropyridine FLI-06 disrupts the Golgi by mechanisms different from BFA or GCA. a) For structure-activity relationships FLI-06 (1) and derivatives (2 to 7) were incubated on HeLa-NotchΔE-EGFP cells and $EC_{50}$ values determined. b) Results from testing compounds using the HeLa-NotchΔE-EGFP cells. c) Structural information on the compounds tested according to the experiment shown in b). d) HeLa cells were incubated with DMSO or FLI-06 (10 µM) for 18 h, fixed, stained with antibodies as indicated and imaged by fluorescence microscopy. e) HeLa cells were transfected with GBF1-GFP, incubated the next day with DMSO or FLI-06 (10 µM) or BFA (10 µg/ml) or GCA (10 µM) for 10 h, fixed, and imaged by fluorescence microscopy. Scalebar: 10 µm.

FIG. 6: FLI-06 affects recruitment of cargo to ER exit sites. a, a', b) HeLa cells were transiently transfected with VSVG-EGFP and incubated overnight at 40° C. 30 min before the chase microtubuli were depolymerized by incubation on ice and treatment with nocodazole. Concurrently, cells were preincubated with DMSO (control) or FLI-06 (10 µM). Cells were then chased at 32° C. for indicated times in the presence of nocodazole and compounds, followed by fixation and processing for fluorescence microscopy using antibodies against Sec31. a) Overview of treated and untreated cells at selected time points. Scalebar 10 µm. a') Magnified selected areas from a); V, VSVG-EGFP; S, Sec31; M, merge. Double arrow, VSVG-EGFP in post-ERES compartment, next to an ERES; arrowhead, ERES costained with VSVG-EGFP and Sec31; scalebar 3 µm. b) Quantitation of variance of pixel fluorescence intensity (PFI-Var) in region of interests (ROI) from n=3 experiments as in a). For each condition at least 10 ROIs were measured. Error bars SEM. r.u., relative units. Mean PFI-Var at time 0 was set to 1 and the other values related to that. c) HeLa-NotchΔE-EGFP cells were pretreated for 4 h with FLI-25, an inactive derivative of FLI-06 (see FIG. 5), or with FLI-06 where indicated. Cells were permeabilized and the budding reaction performed with cytosol, ATP regenerating system and compounds as indicated. After the reaction COPII vesicles were isolated and probed for ribophorin I (ER marker), ERGIC-53 and Sec22b (both proteins are incorporated in COPII vesicles).

FIG. 7: FLI-06 induces ER sheet formation. A) COS cells transfected with prIss-KDEL-mRFP were incubated with 10 µM FLI-06 for indicated times and imaged by live-cell microscopy. The inserts are magnifications of the boxed areas. B) Images from cells treated as in A) were scored for the percentage of cells that lost most of their ER-tubules. For each time point 40-60 cells were counted. Data represent mean percentages, error bars SEM, n=3 independent experiments.

FIG. 8: DAPT-like phenotype of FLI-14, -15, -19 and -20 at 50 iM. HeLa cells stably expressing NotchΔE-EGFP were incubated with 1 iM DAPT or 50 iM compounds for 16 h, fixed and processed for immunofluorescence. In all conditions, cells displayed a strong PM accumulation of NotchΔE-EGFP and a strong reduction in nuclear NICD-EGFP.

FIG. 9: Compound effects are not cell-type specific. U2OS cells stably expressing NotchΔE-EGFP were incubated for 18 h with 10 iM compounds as indicated, fixed and imaged by fluorescence microscopy. FLI-14, -15, -19 and -20 cause PM accumulation similar to DAPT, FLI-06 caused ER accumulation of the reporter and in some cells aggregation, indicating that phenotypes of all compounds are not cell-type specific. Arrows, plasma membrane; arrowheads, ER. Asterisks indicate cells where the ER collapsed to large aggregates. Scalebar, 10 im.

FIG. 10: Phenotypes of Notch inhibitors are fully reversible. HeLa NotchΔE-EGFP cells plated in LabTek coverglass were incubated for 18 h with 10 iM of indicated compounds, washed and incubated for indicated times in cell culture medium. Cells were imaged by live-microscopy. ER accumulation (FLI-06) or PM accumulation (FLI-14, -15, -19, -20) of NotchΔE-EGFP reversed after 1-4 h of washout to the normal accumulation of NICD-EGFP in the nucleus, demonstrating full reversibility of compound effects. In addition these data show no gross toxicity of the compounds. Scalebar, 10 im.

FIG. 11: Selected compounds affect somite formation and neurogenesis in vivo in zebrafish embryos. a) Lateral view of typical representative phenotypes induced by DAPT treatment, which were used as a reference to score the effect of compounds. Embryos treated at 6 hpf with 50 iM DAPT resulted in either defective somitogenesis (mild), head and trunk malformation (strong) or developmental delay (delayed). Images were taken at 24 hpf. b) Pie chart showing the cumulative relative frequency of the phenotypes in a) at 24 hpf in embryos treated with 20, 50 and 100 iM of the indicated compounds. c) ISH with riboprobes specific for ngn1 was performed on dechorionated stage 4 hpf zebrafish embryos. Anterior is to the left, dorsal to the top. Magnifications of the developing head (box) are shown. Arrows indicate larger ngn1 clusters or stronger ngn1 staining. t, telencephalon; p, protectum; h, hindbrain; d, diencephalon; tg, tegmentum; vrc, ventral rostral cluster.

FIG. 12: FLI-06 disrupts the Golgi not via depolymerizing microtubuli or actin. HeLa cells were incubated for 4 h with 1.5 ig/ml nocodazole (a) or 2 iM cytochalasin D (b) or 10 iM FLI-06. Thereafter cells were fixed and processed for immunofluorescence microscopy using antibodies against tubulin. a) Nocodazole, but not FLI-06 disrupted the microtubular network in interphase cells and the mitotic spindle (arrowheads) in mitosis. b) Cytochalasin D, but not FLI-06 depolymerized f-actin. Scalebar, 10 im.

FIG. 13: FLI-06 causes dispersal of early Golgi and TGN, but no tubulation of endosomes. Hela cells were incubated with DMSO or 10 iM FLI-06 or 1 ig/ml BFA for 18 h, fixed, stained with antibodies as indicated and imaged by fluorescence microscopy. Endosomes were visualized by adding Alexa555-labelled transferrin on ice and chasing for 15 min at 37° C. in the presence of indicated compounds. Arrows indicated tubulating endosomes, scalebar 10 im.

FIG. 14: FLI-06 acts different from BFA. a) HeLa cells were incubated for indicated time points with 1 ig/ml BFA or 10 iM FLI-06, fixed and processed for immunofluorescence microscopy using antibodies against βCOP and giantin. While with BFA βCOP rapidly dissociates from the Golgi within 10 min, it takes much longer for FLI-06. b) HeLa cells were transfected with prlss-KDEL-mRFP (ER) and B4GALT-EGFP (Golgi), incubated for indicated time points with 1 ig/ml BFA or 10 iM FLI-06, fixed and processed for immunofluorescence microscopy. In contrast to BFA, FLI-06 does not lead to fusion of ER and Golgi. The ER-like staining of the Golgi-marker at 360 min is probably due to newly synthesized protein. c) HeLa cells were transfected with VSVG-EGFP and incubated at 40° C. throughout to keep VSVG-EGFP in the ER. Cells were treated for 4 h at 40° C. with 10 ig/ml cycloheximide and DMSO, BFA or FLI-06 as indicated, lysed and subjected to SDS PAGE. Incubation with BFA but not FLI-06 led to hyperglycosylation in the ER, indicated by the lower mobility in SDS-gels (hyperglyc.). This hyperglycosylation suggests that Golgi-resident enzymes redistributed to the ER in case of BFA, but not FLI-06.

FIG. 15: FLI-06 inhibits transport of GPI-anchored and soluble proteins and does not cause ER stress. a) HeLa cells were transiently transfected with YFP-GPI (kindly provided by Patrik Keller) and incubated for 18 h with DMSO or 1 ig/ml BFA or 10 iM FLI-06. Thereafter cells were fixed and analyzed by immunofluorescence microscopy. FLI-06 and BFA inhibit surface transport of YFP-GPI. b) HeLa cells were transiently transfected with a plasmid coding for the secreted ectodomain of Klotho, KlothoS, kindly provided by Makoto Kuro-o). After incubating with compounds for 18 h media were collected, cells lysed and both analyzed by Western Blotting using Klotho antibody. As loading control membranes were probed for actin. BFA and FLI-06 inhibit secretion of KlothoS. c) Hela cells were incubated with indicated compounds, lysed after 6 or 24 h, blotted and probed for BIP or actin as loading control. d) Hela cells transfected with the luciferase-based ER-stress indicator plasmid p5xATF6-GL3 (Addgene #11976) and Renilla control plasmid were incubated with indicated compounds, lysed after indicated time points and luciferase activity was determined. 21 g/ml Tunicamycin (Tun) and 5 mM DTT were used as positive controls. In both assays FLI-06 caused only very mild ER-stress after 24 h. Shown is the average of three independent experiments, error bars indicate standard deviation.

FIG. 16: Only ER exit inhibitors convert ER tubules to sheets. COS cells plated on LabTek chambered coverslips were transiently transfected with prlss-KDEL-mRFP, incubated the next day for 2 h with 10 iM of indicated compounds and imaged by live-cell microscopy. Only the ER exit inhibitors (see FIG. 5a) FLI-06, 3, 4 and 5 showed prominent ER sheet formation. FLI-06+CHX, cells were additionally incubated in 40 iM cycloheximide. Nife, nifedipine; nimo, nimodipine. Numbers refer to numbering in FIG. 5a.

FIG. 17: FLI-06 blocks ER-export instantaneously. HeLa cells were transiently transfected with VSVG-EGFP and incubated overnight at 40° C. 30 min before the chase microtubuli were depolymerized by incubation on ice and treatment with nocodazole. In addition, cells were preincubated for 30 min with DMSO (control) or FLI-06 (FLI-06+ 30 min pre), or for 10 min with FLI-06 (+10 min pre), or FLI-06 was added only to the chase medium (FLI-06 no pre). Cells were then chased at 32° C. for indicated times in the presence of nocodazole and FLI-06 (except control), followed by fixation. Quantitation of variance of pixel fluorescence intensity (PFI-Var) was performed in regions of interest (ROI) in at least 15 cells per condition per experiment. n=3 independent experiments, error bars SEM. a.u., arbitrary units. Even when added only to the chase medium without preincubation FLI-06 inhibits concentration and subsequent ER-export of VSVG-EGFP.

FIG. 18: FLI-06 inhibits secretion of secreted alkaline phosphates; FLI-06 kills cancerous, Notch dependent T-cells. a) The secreted alkaline phosphatase (SEAP) assay was carried out. Medium was collected and SEAP secretion was measured via photometry. Inhibition of secretion of SEAP upon FLI-06 incubation was confirmed. b) DND-41 cells have activating Notch mutations (Weng et al, 2004, Science 306, 269). The cells were grown in suspension with the indicated amounts of FLI-06 or DMSO control and growth was determined via FACS analysis. Medium concentrations (1 µM) of FLI-06 inhibited proliferation, while high concentrations (10 µM) of FLI-06 killed the cancer cell line.

Figure 19:
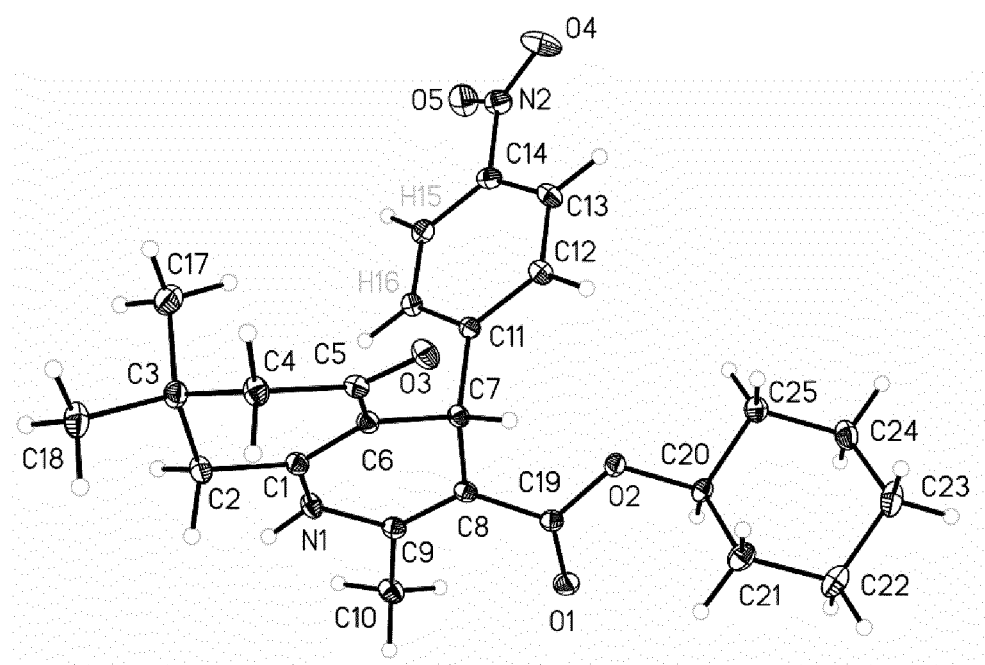

FIG. 19: Molecular structure of FLI-06. Thermal Ellipsoids are displayed at 40% probability level.

FIG. 20 shows a top 7 hit list from the compound screen. Images from the 352 initial hits were visually inspected and 7 compounds with prominent phenotypes and intact nuclei were selected. $EC_{50}$ values were determined as described in the methods section.

EXAMPLES

The examples provided herein represent practical support for particular embodiments of the invention and are not intended to limit the scope of the invention. The examples are to be considered as providing a further description of possible and potentially preferred embodiments that demonstrate the relevant technical working of one or more non-limiting embodiments.

Establishment of a Microscope-Based High-Content Screen

To identify novel regulatory factors involved in Notch trafficking/processing an image-based high content screen was set up. To this end a HeLa Kyoto cell line stably expressing an EGFP-tagged, transcriptionally inactive and ligand-independent Notch1-construct was employed (FIG. 1a, NotchΔE-EGFP[15]). NotchΔE-EGFP is a direct substrate for γ-secretase at the PM, and under physiological conditions is proteolytically processed to NICD-EGFP that translocates into the nucleus (for scheme see FIG. 1b), resulting in a strong nuclear EGFP-staining in steady state[15] (FIG. 1d). Upon inhibition of γ-secretase with the GSI DAPT, the reporter accumulated at the PM while nuclear fluorescence decreased (FIG. 1d). Importantly, changes in subcellular localization of the reporter are amenable to quantitation by automated microscopy[15]. Accordingly, reporter fluorescence was determined in the nucleus (nuc) and in a ring around the nucleus (enuc), and the ratio enuc/nuc was evaluated (schematized in FIG. 1c). Thereafter, the assay design was functionally validated. DAPT-induced accumulation of the reporter outside the nucleus was found concentration-dependent with an EC50 of 0.68±0.2 iM (18 h incubation, FIG. 1e). NICD-EGFP fluorescence in the nucleus decreased with a $t_{1/2}$ of 4.7±1.0 h and $t_{9/10}$ of 8.6±2.9 h at 1 µM DAPT (FIG. 1e). Visual inspection suggested that the cells were viable at all times. We showed before that with these cells defects in nuclear import of NICD could be quantified by automated microscopy[15]. The assay also reliably detected trafficking defects in the secretory pathway. For example, blocking the anterograde transport of NotchΔE-EGFP through the secretory pathway at the Golgi by the ionophore monensin[16] in a dose-dependent manner could be quantified by automated microscopy (FIG. 1f, g). Furthermore, accumulation of NICD in the nucleus upon inhibiting proteasomal degradation by MG132 was detected by automated microscopy (FIG. 1h, i). Taken together, the assay was validated for reliably detecting concentration and time dependent changes in trafficking and processing of the Notch reporter.

After assay conditions were optimized for 384 well plates and automated liquid handling, the NotchΔE-EGFP reporter cell line was screened against the ChemBioNet library comprising 16,671 compounds[17] (summarized in FIG. 1j). Enuc/nuc ratio was computed and the 352 top-scoring compounds were investigated in follow-up experiments. Images were visually inspected for phenotype, and cell viability and $EC_{50}$ values were determined, resulting in a primary hit list of 68 compounds. For detailed follow-up studies seven compounds were selected (table 1), none of which had been annotated with relevant bioactivity before.
Selected Compounds Block Notch Trafficking/Processing at Distinct Steps For a detailed analysis of subcellular distribution of NotchΔE/NICD the resolution of the HCS images was not sufficient. Therefore, the reporter cell line was plated on coverslips and incubated with 10 µM of individual compounds from the final hit list. After 24 h the localization of NotchΔE-EGFP/NICD-EGFP was determined by fluorescence microscopy. As shown above, in steady state the reporter fluorescence was localized to the nucleus and accumulated at the PM after DAPT treatment (FIG. 2a). Incubation with FLI-14, -15, -19 and -20 caused an accumulation of the reporter at the PM and in perinuclear Golgi-like structures similar to DAPT (FIG. 2a). Nuclear NICD-EGFP fluorescence did not decrease to the extent observed for DAPT, suggesting the compounds are less effective than DAPT. Indeed, strong reduction of nuclear NICD-EGFP fluorescence and concomitant accumulation at the PM was achieved after incubation with 50 µM of FLI-14, -15, -19 and -20. (FIG. 8). FLI-06 treatment resulted in reduced nuclear fluorescence and localization in intracellular membranes. Other compounds did not alter the reporter localization in this primary validation (FIG. 2a, FLI-13, FLI-16).

Next, lysates of HeLa NotchΔE-EGFP cells treated with compounds were analyzed for processing of NotchΔE-EGFP by Western blot using antibodies specific for EGFP and NICD (FIG. 2b, c). The GFP antibody detected both the uncleaved reporter NotchΔE-EGFP and the γ-secretase product NICD-EGFP, whereas the NICD-specific antibody specifically detected cleaved NICD-EGFP. Treatment of cells with FLI-06, -14, -15, -19 and -20 resulted in accumulation of NotchΔE-EGFP. Concomitantly, FLI-06, -14, -15 and -20 resulted in decreased NICD-EGFP production. FLI-13 and FLI-16 had no influence on NotchΔE-EGFP processing. The observed effects were not cell type specific, as they were also apparent in U2OS cells stably expressing NotchΔE-EGFP (FIG. 9). Live-cell microscopy after washout of the components indicated that phenotypes of FLI-06, -14, -15, -19 and -20 were fully reversible within 1-4 h, which also indicates that the compounds are not acutely toxic in cells (FIG. 10).
Four Compounds are γ-Secretase Inhibitors The accumulation of NotchΔE-EGFP at the PM and the reduction of NICD-EGFP in the nucleus suggested that FLI-14, -15, -19 and -20 affected γ-secretase processing. γ-secretase has many substrates besides Notch, most prominently the amyloid precursor protein APP, for review see[2]. To test if the compounds that affected NotchΔE-EGFP processing also affected APP processing, HEK293 cells were used that stably expressed $APP_{swe}$, a mutated APP that yields robust amounts of Aβ[18]. Aβ in the cell supernatant was weakly reduced after treatment with FLI-15 and -20 but essentially disappeared after treatment with FLI-06 and FLI-14, similar to the GSI DAPT (FIG. 3a). Likewise, $APP_{CTF}$, the direct substrate of γ-secretase, accumulated in FLI-14, -15 and -20 treated cells, consistent with the effects on Aβ, In FLI-06 treated cells no $APP_{CTF}$ accumulated despite strongly reduced Aβ secretion suggesting that APP is not cleaved by β-secretase. All other compounds had no effect on $APP_{CTF}$ or Aβ. When analyzing APP and APPs, the shedded ectodomain of APP processed by α- and β-secretase[19], we observed that FLI-06, but not the other compounds changed the glycosylation pattern of APP and abolished the shedding of APPs. FLI-16, -19 and -20 reduced APPs secretion (FIG. 3a).

To test whether FLI-06 affected other membrane proteins, Klotho, a type I protein processed like APP and Notch[20], was analyzed. Treatment of HEK293 cells stably expressing Klotho with FLI-06, but not with the other compounds, resulted in aberrant glycosylation different from the normal immature and mature forms of Klotho (FIG. 3a). The mature, complex-glycosylated post-Golgi form of Klotho was strongly reduced, suggesting that FLI-06 affected the trafficking of Klotho. Likewise, when shedded $Klotho_s$ derived from α- and β-secretase cleavage was assayed, FLI-06 but not the other compounds led to a strong reduction of $Klotho_s$ in the medium, suggesting that FLI-06 inhibited cell surface transport (FIG. 3a). These data suggested that FLI-14, -15, -19 and -20 acted on γ-secretase, whereas FLI-06 probably acted by interfering with transport in the secretory pathway. To analyze γ-secretase activity, in vitro assays using isolated membranes were performed (FIG. 3b, c). Production of NICD-EGFP and AICD (APP intracellular domain) were assayed. Both were produced in vitro at 37° C. but not at 4° C., and their production was inhibited by DAPT. Among the tested compounds, only FLI-15 and FLI-20 clearly reduced NICD-EGFP and AICD production, suggesting that they acted as direct, non-substrate selective γ-secretase inhibitors. In contrast, FLI-06, -14 and -19 did not affect γ-secretase in isolated membranes (FIG. 3b, c). FLI-13 and -16, shown not to be active in the cellular assays, also did not affect in vitro γ-secretase activity. Taken together, these data suggest that (i) FLI-15 and -20 inhibited γ-secretase in cells and in vitro, (ii) FLI-14 and -19 inhibited Notch and APP processing in cells, but not γ-secretase in vitro and (iii) FLI-06 affected general transport through the secretory pathway.
Effects of Compounds on Endogenous Notch Signaling We wanted to test whether the results obtained with the NotchΔE-EGFP construct are relevant for endogenous Notch signaling. Therefore we made use of C2C12 cells, a well established model for muscle development that expresses endogenous Notch[21,22]. After stimulating endogenous Notch signaling by transfecting the Notch ligand Delta, Notch activity was measured by a luciferase assay using a Notch reporter[15] in the presence or absence of compounds (FIG. 4a). FLI-06, -14 and -16 strongly, and FLI-19 considerably inhibited endogenous Notch signaling at 10 μM, similar to DAPT. FLI-15 and -20 hardly affected Notch signaling at 10 μM, but remarkably at 50 μM (FIG. 4a, only 50 μM values are shown). Next, we tested whether selected compounds would affect Notch signaling in vivo. To this end the zebrafish *Danio rerio* was used because of its versatility to study early developmental processes and because it shows a distinct Notch phenotype in somitogenesis and neurogenesis when treated with GSI[23,24]. Compounds were added to dechorionated stage 4 hpf zebrafish embryos and the effects were analyzed after 24 h by morphological inspection of somite formation. Phenotypes were ranked to four categories, normal somites, mild somite defects, strong somite defects and developmental delay. All compounds induced distinct Notch phenotypes similar to DAPT (FIG. 11a, b). As an additional parameter we decided to analyze Notch-dependent genes involved in neurogenesis. Primary neurogenesis in zebrafish involves the selection of neuroblasts (repressed by Notch) from proneural clusters (Notch expressing cells), a process regulated in a negative manner by Notch-dependent lateral inhibition[25]. Accordingly, neuroblast cells that express the neuronal specification factor neurogenin (ngn1[26]) became more abundant when Notch signaling was impaired, for instance upon DAPT treatment[23,27]. qPCR analyses on mRNA extracted from equivalent sets of embryos was performed for ngn1 expression (FIG. 4b). Upon treatment with DAPT, FLI-06, -14, -15 and -20 ngn1 mRNA levels were significantly increased, while treatment with FLI-16 and -19 did not induce significant changes in ngn1 mRNA levels. To confirm the data obtained by qPCR, whole-mount in-situ hybridizations (ISH) using an ngn1 specific riboprobe were performed (FIG. 4c, FIG. 11c). ISH indicated that most of the embryos (<75%, n=10-16 per condition) treated with DAPT or FLI-06, -14, -15 and -20 displayed expanded and denser clusters of ngn1 positive cells along the spinal cord, mostly in the motor neuron layer, compared to DMSO-treated control embryos (FIG. 4c). Likewise, ngn1 positive cell clusters in the developing brain of DAPT as well as FLI-06, -14, -15 and -20 treated embryos were found differentially expanded compared to DMSO controls (FIG. 11c). In contrast, the size of ngn1 positive clusters was reduced in FLI-16 and increased in FLI-19 treated embryos, although both did not induce changes in qPCR analyses. Taken together, FLI-06, -14, -15, -19 and -20 inhibited endogenous Notch signaling in vitro and in vivo, corroborating the NotchΔE-EGFP reporter data.

Small Molecule Hit Validation

From the above experiments, the dihydropyridine FLI-06 (1) emerged as a prominent hit compound with a novel mode of action. In order to confirm the small molecule's structure, it was independently re-synthesized de-novo, purified by re-crystallization, and stringently characterized by X-ray crystallography. This substance was found to be equally active as the initial screening hit. The clinically established $Ca^{2+}$-Channel blockers nifepidine (ortho-$NO_2$ group—not encompassed by the chemical formula of the present invention) and nimopidine (meta-$NO_2$ group—also not encompassed by the chemical formula of the present invention), two structurally related 1,4-dihydropyridines, were tested alongside and found completely inactive in our assay systems, showing that concomitant modulation of $Ca^{2+}$-signaling events is not causal for the observed phenotype (FIG. 5a).

Preliminary SAR studies were then executed using a combination of compound acquisition and dedicated synthesis in order to gain insight into the specificity of compound activity, and to ensure that potentially metabolically labile structural elements ($NO_2$ group, dihydropyridine ring) did not interfere with the phenotype observed. Activity was measured by determining enuc/nuc ratios in NotchΔE-EGFP cells (FIG. 5a). Longer or lipophilic substituents at position R2 according to formula I of the present invention were found to be preferred for activity (Pent (3; FLI-27), cHex (1, 5; FLI-06, FLI-25) and cHept (4; FLI-28)), whilst the iso-pr group also showed the desired effect. Compound 4 (FLI-28) was twice as active as compound 1 (FLI-06).

The 4-$NO_2$ group is a preferred substituent and may be important for the observed phenotype due to rendering its metabolic turnover unlikely. Conversion of the pendant keto group into an O-alkyl oxime again generated an entirely inactive substance (compound 6—not encompassed by the chemical formula of the present invention). Surprisingly, FLI-06 exerted a very unique effect in cells with a mode of action unrelated to known targets of dihydropyridine scaffolds.

Further comparisons were carried out using several compounds of the prior art in order to assess whether the known compounds exhibited the desired functional properties according to the present invention. As shown in FIG. 5b, the compounds HPI-1 from WO 2009/102864, compounds C3, C4 and C5 from WO 2008/103470 and compound ST216093 from WO 2008/070875 were tested in NotchΔE-EGFP cells. Compound E is provided as a positive control.

The specific structures of the compounds of the prior art are shown in FIG. 5c. The compounds HPI-1, C3, C4 and C5 show no activity using the assay of the present invention. The compound ST216093 does however show the desired activity. ST216093 has previously only been disclosed with respect to the treatment of Alzheimer's disease, and is disclosed in WO 2008/070875 as lacking any activity.

FLI-06 Leads to Disruption of the Golgi Apparatus Differently than BFA

At this stage, we intended to investigate the cellular activity of the dihydropyridine FLI-06 in more detail, namely the aberrant accumulation of NotchΔE-EGFP in intracellular membranes (FIG. 2a). The aberrant glycosylation pattern of APP and Klotho as well as their reduced ectodomain shedding (FIG. 3a) suggested that FLI-06 interfered negatively with the secretory pathway. Strikingly, immunofluorescence analysis of HeLa cells with markers for ER (calnexin) and the Golgi (giantin) revealed that FLI-06 caused a complete disruption of the Golgi while the ER, at least when imaged at this resolution, seemed largely unaffected (FIG. 5d). Disruption of the Golgi after FLI-06 treatment could be caused by disassembly of the microtubules[28] or by interfering with membrane trafficking in the early secretory pathway, similar to Brefeldin A (BFA[29]) or Golgicide A (GCA[30]).

In order to discriminate between these alternatives, cells were incubated with FLI-06 or the microtubule-depolymerizing agent nocodazole and analyzed by fluorescence microscopy (FIG. 12a). While after nocodazole treatment the microtubule network was almost completely disintegrated and mitotic spindles were absent in dividing cells, in both treated as well as non-treated cells a fully intact microtubular cytoskeleton and mitotic spindles were observed. Actin polymerization and distribution remained unaffected, which suggested that FLI-06 does not act on the cytoskeleton (FIG. 12b). Similar to BFA, FLI-06 caused dispersal of the cis-Golgi marker GM130 and of the trans-Golgi network (TGN) marker TGN46 throughout the cytosol (FIG. 13). Both FLI-06 and BFA did not affect endocytosis in a transferrin uptake assay. However, in contrast to BFA, FLI-06 did not cause tubulation of endosomes (FIG. 13). Another striking difference to BFA was observed when we assessed the dispersal of βCOP, a component of the COPI-derived coatomer complex[31]. While in BFA-treated cells the Golgi-like juxtanuclear βCOP staining was already lost after 10 min, it took 30-40 min in FLI-06-treated cells (FIG. 14a). In contrast to BFA, treatment with FLI-06 did not lead to fusion of ER and Golgi (FIG. 14b). Again in contrast to BFA, FLI-06 did not cause a hyperglycosylation of VSVG-EGFP (FIG. 14c), consistent with the observation that Golgi-resident enzymes did not redistribute into the ER. BFA acts by inhibiting several Arf-GEFs involved in various trafficking steps in the secretory pathway[32,33]. Golgicide A (GCA) inhibits only GBF1, the Arf-GEF acting on the early secretory pathway[30]. To test whether FLI-06 acts on GBF1, HeLa cells were transfected with GBF1-GFP[34] and treated with BFA, GCA and FLI-06, respectively (FIG. 5e). In untreated cells GBF1-GFP displayed a cytosolic distribution, while in BFA- and GCA-treated cells it is recruited to the fragmented Golgi. In contrast, in FLI-06 treated cells GBF1-GFP displayed the distribution of control cells, suggesting that FLI-06 does not act on GBF1 and therefore different from BFA or GCA. We also noted that BFA and GCA, but not FLI-06 caused ER-stress as indicated by up-regulation of the ER-resident chaperone BIP and ATF6 luciferase assay (FIG. 15c, d). Taken together, these data suggested that the dispersal of the Golgi caused by FLI-06 is not mediated by depolymerizing microtubuli and differs from a BFA-like mechanism.

FLI-06 Inhibits Cargo-Recruitment to ER Exit Sites

The differences between FLI-06 and BFA or GCA-treated cells prompted us to analyze the effect of FLI-06 on the first sorting/budding station in the early secretory pathway, the ER exit sites (ERES). FLI-06 globally affects secretory transport of transmembrane (FIG. 3a), secretory and GFP-anchored proteins (FIG. 15a, b). Therefore, we selected the temperature-sensitive VSVG-tsO45-mutant tagged with GFP (VSVG-EGFP[35]) as general reporter for secretory transport. VSVG-EGFP at 40° C. is misfolded and accumulates in the ER. Upon shifting to the permissive temperature (32° C.), a wave of VSVG-EGFP is exported from the ER and can be followed in real-time[35,36]. VSVG-EGFP was transfected in HeLa cells, incubated at 40° C. to accumulate it in the ER, and released to ERES by shifting to 32° C. in the presence and absence of FLI-06 (FIG. 6a). To slow down export from ERES, cells were additionally incubated with nocodazole[37], which induces depolymerization of microtubuli but does not inhibit ER export. As described before[37], shifting untreated cells to the permissive temperature resulted in the accumulation of VSVG-EGFP in ERES, visualized by colocalization with the ERES marker Sec31a (FIG. 6a, a', 30 min, arrowheads). After 85 min most of VSVG-EGFP had left the ER and ERES and accumulated in post-ERES compartments devoid of Sec31a (FIG. 6a', 85 min, double arrows). In sharp contrast, in cells incubated with FLI-06, VSVG-EGFP remained diffusively distributed in the ER and almost no colocalization with Sec31a was observed after 30 min. After 85 min some weak accumulation of VSVG-EGFP in ERES was apparent (FIG. 6a, a', 85 min, arrowheads). Quantitation of the variance of pixel fluorescence intensity according to Dukhovny et al.[37] supported the observation that in control cells VSVG-EGFP rapidly enters and leaves ERES, whereas in FLI-06 treated cells the recruitment to ERES is strongly reduced (FIG. 6b). Cells shown in FIG. 6 were pretreated with FLI-06 at 40° C. for 30 min, to ensure maximal inhibition. To get an initial idea on the velocity of FLI-06 action, cells transfected with VSVG-EGFP were pretreated for 30 or 10 min prior to the 32° C. chase, or FLI-06 was only added to the chase medium. In both cases ER export was inhibited to the same extend as with the 30 min preincubation, indicating that FLI-06 acts instantaneously on ER export (FIG. 16). Interestingly, although no VSVG-EGFP and presumably no other cargo was recruited, Sec31a puncta were still observed after FLI-06 treatment (FIG. 6a). The immunofluorescence data on VSVG-EGFP suggested that FLI-06 acted on a pre-ERES step, such as cargo recruitment. Therefore, it should not affect COPII budding from ERES. To test this hypothesis, a well-established in vitro budding assay using permeabilized cells, rat liver cytosol and an ATP regenerating system was employed. In this assay ERGIC-53 and Sec22b served as markers for proteins incorporated into COPII vesicles and ribophorin I as a marker for an ER-resident protein[38]. This assay demonstrated that FLI-06 did not inhibit the COPII budding reaction when added directly to the assay (FIG. 6c), whereas H89, a known inhibitor of Sar1-mediated ER-export[39], completely blocked formation of COPII vesicles. In contrast, when cells were pretreated with FLI-06 for 4 hours, the budding of COPII vesicles was slightly inhibited in the absence of FLI-06 and strongly in the presence of 100 µM FLI-06. As a control, all other cells were pretreated with FLI-25, an inactive derivative of FLI-06 (see FIG. 5a). When added to the budding reaction, neither 10 nor 100 µM of FLI-25 had an effect on the in vitro COPII budding reaction. In summary, these data suggest that FLI-06 inhibits ER-export at a pre-ERES step, potentially at the stage of cargo recruitment. They establish FLI-06 as the first small molecule probe decisively affecting this early step in the secretory pathway.

FLI-06 Converts Tubular ER to Sheets

We noted a morphological change of the ER upon FLI-06 incubation that was difficult to capture in fixed cells. Live-cell imaging was therefore performed in COS cells transfected with the ER marker prlss-KDEL-mRFP (supp. Ref 3) and FLI-06 was added for 120 min (FIG. 7a). After 120 min almost all cells had no detectable ER-tubules anymore and instead were filled with large sheet-like structures. Sheet-formation started after 5-10 min and had a $t_{1/2}$ of about 14 min (FIG. 7b). To test whether the morphological change is related to the inhibition of ER exit, next our set of FLI-06 derivatives was tested. Only FLI-06, 3, 4 and 5, those derivatives that were inhibiting ER exit, also elicited the tubule-to-sheets phenotype, strongly suggesting that both effects are related (FIG. 17). In addition, incubating cells with FLI-06 and cycloheximide demonstrated that the sheet formation is not the result of cargo accumulation in the ER (FIG. 17). Because ER exit inhibition precedes sheet formation, the data suggested that sheet formation is not causative for the ER exit block. Rather, the ER-sheets are indicative for structural changes, maybe initiated within ERES, that inhibit ER exit.

FLI-06 Inhibits Secretion of Secreted Alkaline Phosphates

In order to confirm the inhibitory effect of FLI-06 on secretion we transfected HeLa cells with a plasmid encoding a secreted alkaline phosphatase (SEAP). We collected the medium and measured SEAP secretion via photometry and could confirm inhibition of secretion of SEAP upon FLI-06 incubation (FIG. 18a).

FLI-06 Kills Cancerous T-Cells

To test whether FLI-06 would ultimately be useful to treat cancerous diseases we incubated DND-41 cells having a Notch heterodimerization domain that leads to hyperactive Notch signaling (Weng et al, Science, 2004) with FLI-06. 10 µM FLI-06 caused total cell death after 4 days while 1 µM FLI-06 inhibited proliferation of DND-41 cells (FIG. 18b).

Discussion of the Experimental Examples

The identification of small compounds specifically modulating a biological process constitutes a key step toward drug discovery. Here, we have developed and applied automated microscopy-based HCS to find novel compounds affecting the Notch pathway. Notch signaling is implicated in numerous developmental processes, differential decisions and—not surprising for such an important pathway—is implicated in a number of pathological conditions like neurodegeneration and T-ALL[9,40]. In the initial screen we intended to focus on trafficking/processing aspects of Notch signaling. We used an EGFP-tagged reporter construct that was transcriptionally inactive. The fluorescence of this Notch-based reporter was quantified in the nucleus and in a ring around the nucleus, to identify hit compounds. It should be emphasized that they were extracted from the primary screening library, and were not further optimized yet. Despite this, FLI-06, -14, -15, -20, and less pronounced -19, did not show acute toxicity on the time scale of our experiments, and clearly reduced endogenous Notch signaling, as shown by reduction of CSL-dependent luciferase-activity in C2C12 cells and by causing somite malformation and neurogenesis phenotypes in vivo in zebrafish.

We found that FLI-06 generally blocked secretion and that the GSIs FLI-14 and -19 as well as FLI-15 and -20 inhibited Notch and APP processing, indicating they are not specific for Notch. Nevertheless, the dominant phenotype of all five compounds observed in vivo was a Notch phenotype, suggesting that future structure-function analyses together with time and dose-optimizations should enable the development of probes interfering more specifically with Notch signaling.

The active probes identified acted on different steps in trafficking and processing of the reporter (schematized in FIG. 18). Four compounds caused accumulation of the Notch-reporter at the PM, suggesting that γ-secretase itself is inhibited or trafficking/interaction of γ-secretase with the Notch-reporter. Indeed, two of the four compounds (FLI-15 and FLI-20) turned out to be novel bona-fide GSIs, but whether they directly inhibit γ-secretase or act indirectly or allosterically remains to be addressed. While GSIs are probably not primary drug leads for Alzheimer disease[41], they show promising therapeutic potential for T-ALL[42]. In addition, GSIs proved to be instrumental for characterization of the different subunits of γ-secretase, for example allosteric interaction sites and substrate binding sites[13]. Interestingly, FLI-14 and -19 did not inhibit γ-secretase at the concentrations used in the in vitro assay, despite the fact that their application resulted in accumulation of the reporter at the PM and their clear effect on endogenous Notch signaling. Potentially, these substances could affect the recruitment of substrate to γ-secretase, its targeting to the PM and/or endosomes, or the targeting of substrate or enzyme to detergent-resistant membrane domains where active γ-secretase resides[43].

Because of its striking phenotype, namely the accumulation of NotchΔE-EGFP in intracellular membranes, the dihydropyridine FLI-06 was studied in more detail. Related 1,4-dihydropyridines such as nifedipine are widely applied as drugs in humans to treat hypertension and are generally recognized as $Ca^{2+}$-channel modulators with antagonistic or agonistic activity[44], but are inactive in our settings. Other physiological activities for dihydropyridines have been investigated, most notably anti-atherosclerotic, hepatoprotective, anti-mutagenic, and anti-diabetic properties[45]. Some of these activities could be related to the antagonistic activity some dihydropyridines show on the mineralocorticoid receptor[46,47]. While the extent of these effects is known to strongly vary with small changes in molecular structure of dihydropyridines[48], specific activity on intracellular trafficking of a dihydropyridine scaffold was completely unprecedented. Similar to BFA and GCA or probes like the PKA inhibitor H89, treatment of cells with FLI-06 resulted in disruption of the Golgi apparatus. However, our experimental data stringently suggested that FLI-06 acted via a different mechanism. FLI-06 did not affect the recruitment of GBF1 to the Golgi, the target of BFA and GCA. In contrast to BFA, the Golgi did not fuse with the ER in the presence of FLI-06, and the kinetics of β-COP dissociation and Golgi dispersal differed between FLI-06 and BFA. Unlike H89, FLI-06 did not directly inhibit COPII budding in vitro. Further studies with VSVG-EGFP suggested that FLI-06 acted on a very early step in recruitment of cargo to ERES.

Mechanistically, the formation of ERES and initiation of cargo recruitment starts with the recruitment of Sar1 by Sec12. Sar1 in turn recruits the cargo receptors Sec23/24. Finally, Sec13/31 are recruited and the fission of a COPII vesicle is initiated (for review see[49]). In the in vitro COPII budding assay pre-incubation of the cells was required to see a block in vesicle formation. This result suggested that FLI-06 does not affect the essential proteins provided by the added cytosol in the budding reaction. At the present stage we hence hypothesize that FLI-06 acts on the level of Sec12 or other currently unknown recruitment factors—or on the membrane structuring events necessary to initiate an ERES. Although no VSVG-EGFP, no NotchΔE-EGFP and presumably no other cargo accumulates at ERES, there are still Sec31 labeled ERES, suggesting that cargo recruitment is not essential for recruiting COPII components to ERES. Strikingly, inhibition of ER exit was followed by a complete tubule-to-sheet transition of the ER. Morphological changes in ER structure can be caused, among others, by disrupting ER-microtubule connections (Klopfenstein, 1998) or by interfering with structural proteins in the ER (Shibata, 2009; Voeltz, 2006). Depolymerizing microtubules did not affect secretion (Rogalski, 1984; Cole, 1996). Sheet formation alone, induced by microtubule depolymerization or interfering with ER-microtubule interacting proteins, does not inhibit ER exit (FIG. 7C) and clearly occurs after blocking secretion. It is not just an indicator of accumulating cargo, and occurs only with FLI-06 and its derivatives that block secretion, strongly suggesting that the two effects are related. ERES are highly curved membrane regions, and we speculate that FLI-06 causes some curvature changes in ERES that inhibit cargo recruitment. Curvature changes spread then all over the ER, leading to the observed sheet formation. Interestingly, while this study was in revision, the small molecule dispergo was discovered (Lu, 2013). Dispergo has the opposite effect since it induces ER tubulation, but like FLI-06 it seems to inhibit recruitment of cargo to ERES. This might indicate that the "correct" membrane curvature at ERES is essential, and shifts in either direction disrupt ER exit.

The activity of the small molecule probe FLI-06 (1) was further validated by resynthesis and focused structure variations (compounds 2-5). These initial experiments on structure-function relationships of FLI-06 showed that larger or bulky alkyl residues increased activity. At the present stage, a p-NO$_2$ group appears to be important but not essential for compound activity. Metabolic modification (oxidation or reduction) of the scaffold seems unlikely, given the rather narrow activity window and fast onset of activity. In addition, the respective derivatives were inactive. Further compounds according to the chemical formulae described herein have been synthesized (see below for information on chemical synthesis) and experimental analysis is ongoing.

Taken together, FLI-06 is a unique chemical for the treatment of secretion-dependent disease. To our knowledge, FLI-06 is the only compound that acts this early in the secretory pathway, at pre-ERES steps. In addition, and as an additional benefit, FLI-06 does not cause significant ER-stress, in contrast to BFA or GCA, thereby indicating reduced side effects after medical administration.

Methods and Materials Applied in the Examples of the Present Invention cDNAs and Antibodies Antibodies and cDNAs used in this work are listed in a table below.

Maintaining of Cell Lines and Generation of Stably Expressing Cell Lines

Cells were maintained in Dulbecco's modified Eagle Medium+GlutaMax (Invitrogen) supplemented with 10% FBS. For stable lines, HeLa Kyoto and U2OS cells were transfected with NotchΔE-EGFP with Lipofectamine 2000 (Invitrogen), sorted via FACS and selected with 100 µg/ml Hygromycin B. Single cell clones were picked and selected based on moderate and homogenous NICD-EGFP nuclear staining. One clone was then selected for further use.

ChemBioNet Compound Screen

The compound screen was performed at the Leibniz-Institut für Molekulare Pharmakologie (FMP) in Berlin as a single screen, measuring the enuc/nuc ratio of the GFP signal. The compounds were applied on 51 screening plates at 10 iM for 24 h and processed for image acquisition and analysis. The Z' for the individual plates ranged between 0.4 and 0.8 (=0.53±0.14), indicating excellent assay conditions with only two plates falling below that range. Activity was assessed by z-score normalization and samples with less than 150 cells were dismissed from further analysis. For hit validation compounds were ordered from ChemDiv or were obtained by chemical synthesis. For further details see methods below.

EC$_{50}$ Determinations

EC$_{50}$ values of the test compounds were calculated from serial dilution series ranging from 200-0.1 µM. Cells were seeded in 96-well plates at a density of 5000 cells/well in 100 µl medium. The next day, 100 µl medium containing the respective test compounds was added. Cells were incubated for 16 h, fixed and processed for automated microscopy. For the putative gamma-secretase inhibitors the enuc intensity was divided by the DAPT control and for the trafficking inhibitors normalized percentage inhibition against DAPT/DMSO controls of log 2 transformed nuc/enuc ratios were calculated. Relative activity values were read into "R" (http://www.r-project.org/) and EC$_{50}$ estimates were calculated using four-parameter log-logistic fit with the package "drc"[51].

Drug Treatments

If not stated otherwise, all drugs were purchased from Sigma Aldrich. Drugs were used at the following concentrations. BFA, 1 µg/ml; Golgicide A (Calbiochem), 10 µM; nocodazole, 1.5 µg/ml; H89, 25 µM; tunicamycin, 10 µg/ml; DAPT (Alexis Biochemicals), 1-2 µM In Vitro γ-Secretase Assay For assaying AICD formation, membranes of HEK293 cells stably expressing APP with the Swedish mutation were isolated and incubated for 4 h at 37° C. according to Sastre et al.[52]. For assaying NICD formation, membranes from HeLa NotchΔE-EGFP cells were mixed with membranes from HeLa NotchΔE-EGFP cells that were pre-treated with 10 µM DAPT overnight to enrich substrate. After incubation samples were loaded onto either 8% SDS-PA gels (NICD) or 10-20% Tris-Tricine gels (AICD), blotted and probed with cleaved-Notch antibody or antibody 6687 against APP C-terminus[53]. Chemoluminescence was quantified on a LAS-4000 (Fuji) with MultiGauge software.

Detection of APP, Klotho and their Cleavage Products

APP, APPs, APP$_{CTF}$ and Aβ detection was as described before[54] using antibodies 22C11 for APP and APPs, 6687 for APP$_{CTF}$ and 3552 and 2D8 for Aβ. Klotho was detected as described in Bloch et al.[20]. Chemoluminescence was quantified on a LAS-4000 (Fuji) with MultiGauge software.

Luciferase Assay

Endogenous Notch signaling in C2C12 was determined by a luciferase assay using a 12xCSL-luciferase reporter and transfected Delta as described before[15].

VSVG-Assay

HeLa cells plated on cover slips were transiently transfected with temperature sensitive VSVG-tsO45-mutant carrying an EGFP-tag (plasmid VSVG3-GFP[35]). After 24 h cells were transferred to 40° C. for 24 h to accumulate VSVG-EGFP in the ER. Before the chase, nocodazole (1 µg/ml) and DMSO or BFA (1 µg/ml) or FLI-06 (10 µM) were added and cells were incubated on ice for 30 minutes to depolymerize microtubules. For the chase, cells were transferred to a waterbath with 32° C., fixed after indicated time points and stained with an antibody against Sec31 to detect localization of ERES. During 0° and 32° C. incubations 10 mM HEPES was added.

Transferrin-Uptake

For the transferrin uptake assay cells were starved in serum free medium for 1 h at 37° C. Cells were then transferred on ice and medium was exchanged to serum free medium supplemented with 25 µg/ml AlexaFluor555-Transferrin conjugate (Molecular Probes) and test compounds. After 15 min on ice cells were incubated with pre-warmed serum-supplemented medium containing test compounds and incubated at 37° C.

Fluorescence Microscopy

Immunofluorescence stainings were made using standard procedures[55]. Imaging was performed on a Zeiss Axiovert200 or an Axio Imager, using 63× 1.4NA objectives and Zeiss Axiovision software. For live-imaging cells were plated on Lab-Tek chambered coverglass (Thermo-Fisher). Images were assembled and processed using Adobe Photoshop. For displaying weakly stained ER-tubules/sheets non-linear changes in gamma-settings were used.

Compound Identity

Identity and purity of purchased compounds was verified by thin layer chromatography and mass spectrometry. Chemically synthesized compounds were spectroscopically characterized.

In Vitro Budding Assay

COPII budding in vitro was essentially performed as described in Kim et al.[38].

Zebrafish

Details of zebrafish experiments can be found below.

Statistical Analysis

Means of numerical data were compared using Student's t-test. A difference in means was considered statistically significant (*) with p<0.05 or p<0.01 as indicated. Error bars depict the standard error (SEM) or standard deviation (SD) as indicated. The number of independent replicates is also indicated in the figure legends.

Antibodies

| Antibody (target/markerfor) | species, poly/monoclonal | supplier, order number or reference |
|---|---|---|
| Sec31a (ERES) | mouse, mono | BD, #612350 |
| Klotho | goat, poly | R&D Systems, AF1819 |
| Klotho | rat, mono | KM2119 (Supp. Ref 1) |
| actin | rabbit, poly | Abcam, ab8227 |
| NICD (V1744) | rabbit, poly | Cell Signaling, #2421 |
| 6687 (APP C-terminus) | rabbit, poly | gift from C. Haass, (Supp. Ref 2) |
| BIP/GRP-78 (ER) | goat, poly | Santa Cruz, sc-1051 |
| β-COP (Golgi) | rabbit, poly | ThermoFisher, PA1-061 |
| Giantin (Golgi) | mouse, mono | Enzo, ALX-804-600 |
| Calnexin (ER) | mouse, mono | Chemikon/MilliPore, MAB3126 |
| FLAG | mouse, mono | Sigma F3165 |
| ERGIC53 (ERGIC) | rabbit, poly | Schekman Lab 2925/2926 |
| LAMP1 (lysosom) | rabbit, poly | abcam, ab19294 |
| GM130 (cis-Golgi) | mouse, mono | BD, 610822 |
| GFP | rabbit, poly | Invitrogen A11122 |
| a-tubulin | mouse, mono | Sigma T9026, DM1a |
| TGN38 (TGN) | rabbit, poly | Santa Cruz, sc-33783 |
| 3552 (Aβ) | rabbit, poly | gift from C. Haass |
| 2D8 (Aβ) | rat, mono | gift from C. Haass |
| 22C11 (APP, APPs) | mouse, mono | Millipore |

| Plasmid (marker for) | provided by |
|---|---|
| prlss-KDEL-mRFP3 (ER) | Erik Snapp, Albert Einstein College of Medicine New York, NY 10461, USA [Snapp, 2006 #3402] |
| p5xATF6-GL34 (ER stress indicator) | Addgene #11976 |
| pGL4, 74 (*Renilla* expression control) | Promega |

ChemBioNet Compound Screen (See Also Table 2)

For the compound screen 3000 cells were pre-seeded in 384-well plates (Corning, Corning, N.Y.) in DMEM+10% FBS with a multi dispenser. The next day, compounds were added from a 1 mM stock library at 0.5 il to a final concentration of 10 iM per well. Controls were added with a multichannel pipette at 21M for DAPT and 1% final DMSO in 50 il. Pipetting was performed with a Caliper robot. The plate layout included 16 wells for each control. Plates were incubated for 24 h at 37° C., 95% relative humidity, 5% CO2. After incubation cell culture medium was aspirated and replaced with 25 il 4% formalin for 20 min. After fixation cells were washed once with PBS and nuclei were stained with 51M Hoechst for 20 min. After another washing step cells were covered with 25 il PBS. The screened library was described (ref 17).

HCS Image Acquisition and Data Analysis

Images were acquired on an ArrayScan VTi automated microscope (ThermoFisher) and numerical data were extracted with the Compartmental Analysis BioApplication of the bundled software suite. Compound screening raw data were collected at the FMP and data transformation was performed according to standard procedures (ref 17 and supp. Refs 6-7).

Identity and Purity of Commercially Acquired Samples

The purity of the compounds was tested by using thin layer chromatography (TLC) and mass spectroscopy (MS), which additionally allowed checking the identity. TCL analysis was performed with silica gel 60 F254 aluminum sheets (Merck). Chloroform/methanol mixtures were used as eluent. By UV illumination and iodine staining no impurities were detected. MS was performed on a TRIO 2000 (Fisons) spectrometer in EI ionization mode at 70 eV.

| No. | OrderID and Vendor | MW | Formula | m/Z found | Purity MS |
|---|---|---|---|---|---|
| FLI-06 | 1630-0135 ChemDiv | 438.53 | C25H30N2O5 | 438 | OK |
| FLI-14 | C329-0322 ChemDiv | 512.81 | C30H32N4O4 | 512 | OK |
| FLI-15 | C548-2756 ChemDiv* | 405.49 | C17H19N5O3S2 | 405 | OK |
| FLI-19 | 4464-0971 ChemDiv | 565.70 | C32H43N3O6 | 588 (M + Na+) | OK |
| FLI-20 | STK164160 Vitas-M | 383.51 | C21H25N3O2S | 438 | Impurity with M = 438.6 |
| FLI-24 (3) | BAS00087237 Asinex | 398.45 | C22H26N2O5 | 398 | OK |
| FLI-25 (11) | 1630-1646 ChemDiv | 393.52 | C25H31NO3 | 393 | OK |
| FLI-27 (4) | OSSL_264545 Princeton Biomol. Res. | 426.51 | C24H30N2O5 | 426 | OK |
| FLI-28 (5) | OSSK_158427 Princeton Biomol. Res. | 452.23 | C26H32N2O5 | 452 | OK |

*The ChemDiv entry contains C15H19ClN4O5S3, MW = 466.02; the correct structure was determined by NMR.

Compound Synthesis

Unless otherwise noted, all commercially available compounds were used as provided without further purifications. Reactions were monitored by TLC on 0.2 mm Merck silica plates (60, HF254). 1H and 13C NMR spectra were recorded on Bruker AVANCE 250 or 400 spectrometers, chemical shifts are given relative to residual solvent signals. Melting points were recorded in open capillaries and are uncorrected. Mass spectra were obtained on a TRIO 200 from Fison or on a FINNAGEN MAT DDQ 710. Anhydrous solvents were obtained following general laboratory procedures (supp. Ref 8). Beta-ketoesters were obtained from 2,2,6-trimethyl-4H-1,3-dioxin-4-one and the respective alcohol following published procedures (Supp. Ref 9) and distilled before use. Ammonium acetate was purified and dried by sublimation.

Supporting Scheme 1.
General Synthesis of dihydropyridines FLI-xx and side product structure.

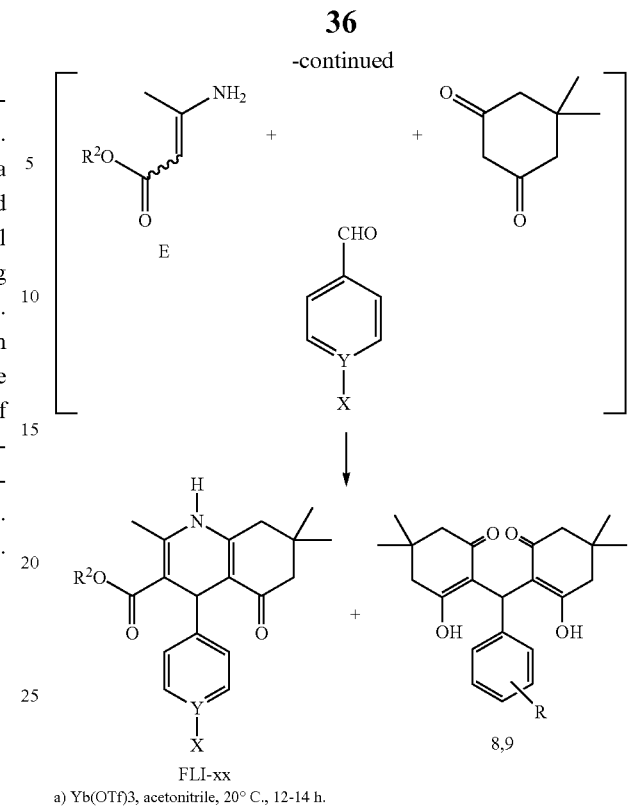

a) Yb(OTf)3, acetonitrile, 20° C., 12-14 h.

Supporting Scheme 2.
Functionalization chemistry of dihydropyridine FLI-06.

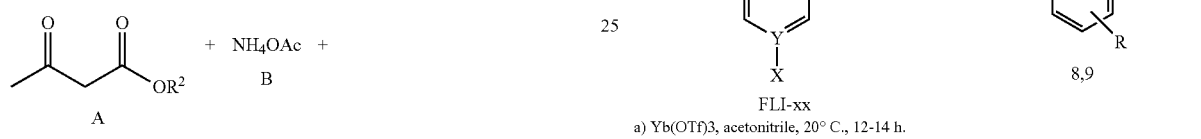

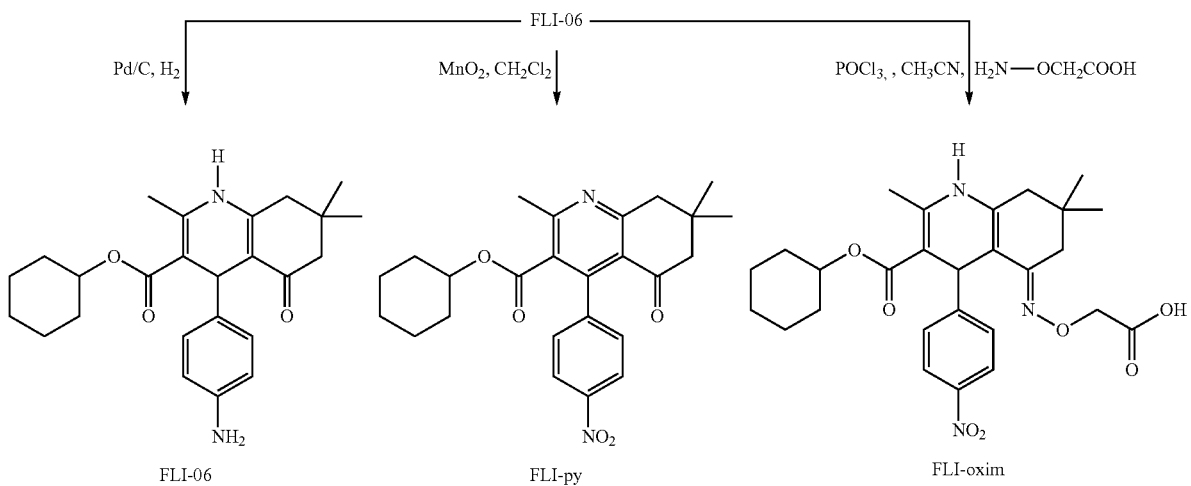

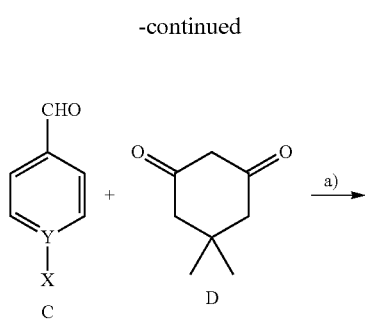

Representative Procedure for Dihydropyridine Synthesis.

Loosely following the precedent of Gestwicki (supp. Ref 10) dimedon D (7.1 mmol, 1.0 g), the respective β-ketoester A (4 mmol) and ytterbium triflate (0.32 mmol, 8 mol %, 0.2 g) were dissolved in anhydrous acetonitrile (25 mL) and stirred under nitrogen for 10 min. A cold (4° C.) solution of anhydrous NH4OAc B (5.6 mmol, 0.3 g) in methanol (10 mL) was introduced. After 10 min the corresponding aldehyde C (4 mmol, dissolved in 10 ml acetonitrile) was added dropwise. The yellowish mixture was stirred at room temperature overnight, then poured into water (100 mL) and stirred for one hour. The precipitate formed was either filtered of by suction or extracted with ethyl acetate.

The remaining material was dissolved in ethyl acetate/hexanes and filtered over a short column of silica. The solvent was removed, the residue recrystallized form acetonitrile and dried in vacuo. Transformations were generally cleaner when the enamineoester E was individually formed (Supp. Ref 11). As side products, symmetrical double adducts of dimedone and aldehyde were observed in varying amounts (see supporting scheme 1) and individually isolated for comparative testing (see below).

Ethyl 4-(4'-nitrophenyl)-2,7,7-trimethyl-5-oxo-1,4,5,6,7,8-hexahydroquinoline-3-carboxylate

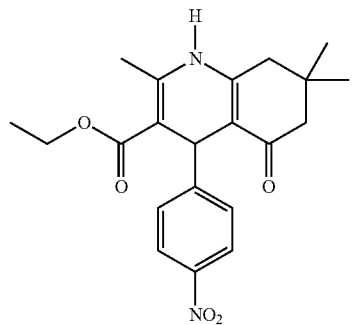 [SMILES: CCOC(=O)C1=C(C)NC2=C(C(=O)CC(C)(C)C2)C1c1ccc([N+](=O)[O-])cc1]

Light yellow crystals; yield: 61%; m.p. 188° C.; 1H NMR (250 MHz, CDCl3): ä 8.09 (d, J=8.7 Hz, 2H), 7.49 (d, J=8, 7 Hz, 2H), 6.93 (br s, 1H), 5.16 (s, 1H), 4.09 (q, J=7.0 Hz, 2H), 2.41 (s, 3H), 2.28-2.10 (m, 4H), 1.25 (t, J=7, 2 Hz, 3H), 1.09 (s, 3H), 0.91 (s, 3H); 13C NMR (62.5 MHz, CDCl3): ä 195.1, 166.7, 154.2, 146.2, 144.2, 128.9, 123.3, 111.3, 105.1, 60.1, 50.5, 41.2, 37.2, 32.7, 29.3, 27.1, 19.5, 14.2; MS (EI): m/z (%) 384 (M+) (66), 355 (21), 262 (100), 234 (81), 178 (29), 150 (17), 83 (9).

Cyclohexyl 4-(4'-nitrophenyl)-2,7,7-trimethyl-5-oxo-1,4,5,6,7,8-hexahydroquinoline-3-carboxylate (1, "FLI-06")

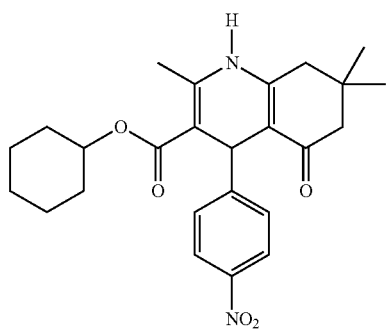 [SMILES: CC1=C(C(=O)OC2CCCCC2)C(c2ccc([N+](=O)[O-])cc2)C2=C(CC(C)(C)CC2=O)N1]

Light yellow crystals; yield: 51%; m.p. 196° C.; 1H NMR (250 MHz, DMSO-d6): ä 8.09 (d, J=8.8 Hz, 2H), 7.51 (d, J=8.8 Hz, 2H), 5.94 (s, 1H); 5.16 (s, 1H), 4.69-4.69 (m, 1H), 2.42 (s, 3H), 2.33-2.16 (m, 4H), 1.80-1.21 (m, 10H), 1.09 (s, 3H), 0.90 (s, 3H);
13C NMR (62.5 MHz, CDCl3): ä 195.2, 166.2, 154.3, 148.3, 146.2, 144.0, 129.9, 123.4, 111.2, 105.3, 72.5, 50.6, 41.2, 37.3, 32.7, 31.8, 31.5, 29.3, 27.1, 25.3, 23.8, 23.6, 19.5; MS (EI): m/z (%)=438 [M+] (67); IR (ATR, [cm-1]): 3198 (m), 3088 (w), 2937 (m), 1672 (s), 1600 (s), 1482 (s), 1468 (m), 1340 (vs), 1433 (vs), 1171 (m), 1107 (s); analysis calcd. for C25H30N2O5: C, 68.47; H, 6.90; N, 6.39. found 68.7, 7.3, 6.5.

Cyclohexyl 4-(4'-cyanophenyl)-2,7,7-trimethyl-5-oxo-1,4,5,6,7,8-hexahydroquinoline-3-carboxylate

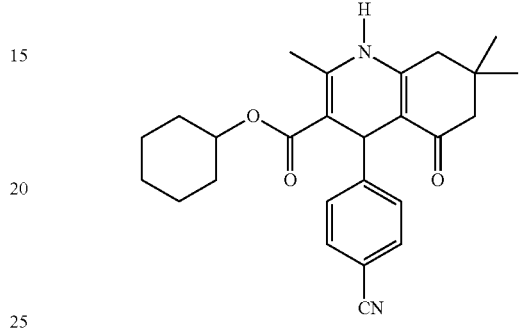

Colourless crystals; yield: 88%; m.p. 235° C.; 1H NMR (250 MHz, CDCl3): ä 7.52 (d, J=8.3 Hz, 2H), 7.45 (d, J=8.3 Hz, 2H), 5.75 (s, 1H), 5.10 (s, 1H), 4.99-5.12 (m, 1H), 2.42 (s, 3H), 2.32-2.27 (m, 4H), 1.81-1.25 (m, 10H), 1.09 (s, 3H), 0.90 (s, 3H); 13C NMR (101 MHz, CDCl3,): ä 195.2, 166.2, 152.2, 147.9, 143.9, 131.8, 128.9, 111.4, 109.6, 105.4, 72.4, 50.6, 41.2, 37.3, 32.7, 31.8, 31.4, 29.3, 27.1, 25.3, 23.7, 23.6, 19.6; MS (DEI): m/z (%)=416 (M+) (24), 334 (100), 317 (20), 278 (37), 260 (9); fluorescence (CH2Cl2): ⌊max.: 432 nm; fluorescence excitation (CH2Cl2): ⌊max.: 371 nm.

Cyclohexyl 2,7,7-trimethyl-5-oxo-4-(pyridin-4-yl)-1,4,5,6,7,8-hexahydroquinoline-3-carboxylate

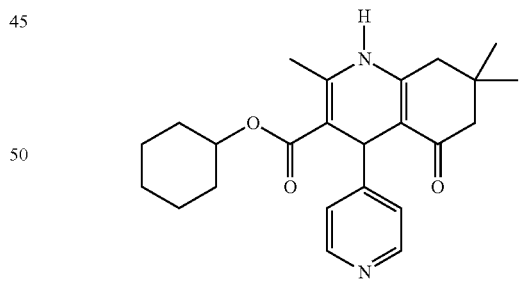

Light yellow crystals; Yield: 33%; m.p. 238° C.; 1H NMR (250 MHz, CDCl3): ä 8.44 (d, J=6.0 Hz, 2H), 7.28 (2H, J=6.1 Hz, 2H), 6.32 (s; 1H), 5.07 (s, 1H), 4.60-4.69 (m, 1H), 2.42 (s, 3H), 2.32-2.17 (m, 4H), 1.83-1.21 (m, 10H), 1.08 (s, 3H), 0.90 (m, 3H); 13C NMR (101 MHz, CDCl3,): ä 195.2, 166.2, 155.4, 149.2, 148.5, 144.4, 123.4, 110.9, 104.8, 72.4, 50.6, 41.1, 36.6, 32.7, 31.8, 31.4, 29.3, 27.0, 25.3, 23.7, 23.6, 19.4. MS (Micro-ESI): m/z (%)=417 (M+Na)+395 (M+H)+ (54); HRMS: calcd. for [M+H]+C24H31N2O3=395.2334. found: 395.2329.

Cyclohexyl 4-(4'-thioamidophenyl)-2,7,7-trimethyl-5-oxo-1,4,5,6,7,8-hexahydroquinoline-3-carboxylate

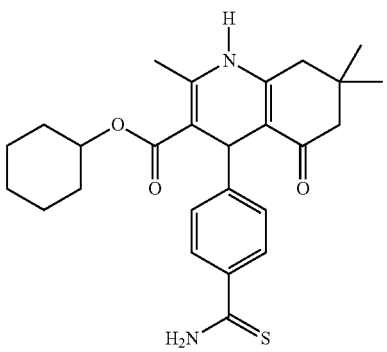 [SMILES: CC1=C(C(=O)OC2CCCCC2)C(c2ccc(C(N)=S)cc2)C2=C(CC(C)(C)CC2=O)N1]

Nitrile 7 (1.2 mmol, 0.5 g) was dissolved in 25 ml DMSO and ammonium sulphide solution (6 ml, 48%) was added with stirring. The pale green mixture was stirred for one hour. Ice cold water was added (100 mL), and stirring was continued for 30 min. The crude product was recovered by filtration and purified by recrystallization from ethanol/water (2:1). Bright yellow needles; yield: 92%; m.p. 231-235° C.; 1H NMR (250 MHz, DMSO-d6): ä 9.69 (s, 1H), 9.32 (s, 1H), 9.07 (s, 1H), 7.71 (d, J=8.3 Hz, 2H), 7.17 (d, J=8.3 Hz, 2H), 4.87 (s, 1H), 4.58 (br s; 1H), 2.44-2.12 (m, 7H), 1.92-1.24 (m, 10H), 0.99 (s, 3H), 0.82 (s, 3H); 13C NMR (101 MHz, DMSO-d6): ä 200.4, 194.7, 166.5, 151.2, 150.2, 145.8, 137.5, 127.4, 127.4, 109.9, 103.8, 71.4, 50.6; 36.5, 32.6, 31.7, 31.4, 29.5, 26.9, 25.4, 23.6; MS (EI): m/z (%)=453 (M+) (18), 369 (9), 316 (82), 234 (100), 190 (11), 83 (15).

Cyclohexyl 2,7,7-trimethyl-4-(4'-nitrophenyl)-5-oxo-5,6,7,8-tetrahydroquinoline-3-carboxylate (7)

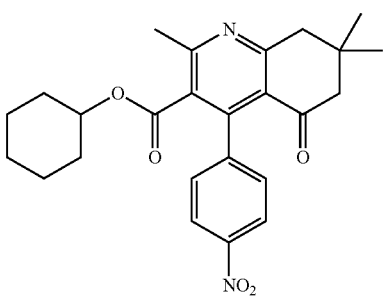 [SMILES: Cc1nc2c(c(-c3ccc([N+](=O)[O-])cc3)c1C(=O)OC1CCCCC1)C(=O)CC(C)(C)C2]

Dihydropyridine 1 (0.436 mg, 1 mmol) was dissolved in dichloromethane (50 mL) and MnO2 (excess, approx. 1 g) was added. The mixture was stirred until the starting material was completely consumed (TLC, hexanes/EtOAc 1:1). The inorganic material was filtered off, solvent was evaporated and the crude compound purified by column chromatography (SiO2, solvent hexanes/EtOAc 1:1). Off-white solid, yield 90%; 1H NMR (250 MHz, DMSO-d6): ä 8.26 (d, J=8.5 Hz, 2H), 7.32 (d, J=8.7 Hz, 2H), 4.66-4.69 (m, 1H), 3.11 (s, 2H), 2.63 (s, 3H), 2.47 (s, 2H), 1.58-1.20 (m, 10H), 1.12 (s, 6H); 13C NMR (101 MHz, DMSO-d6): ä 197.3, 166.1, 163.1, 158.1, 147.3, 145.5, 145.2, 129.7, 129.2, 123.1, 122.6, 74.1, 53.0, 46.9, 32.6, 20.9, 28.1, 26.8, 25.0; MS (EI): m/z (%)=436 (M+) (37), 353 (32), 316 (100), 309 (7), 234 (91).

Cyclohexyl-4-(4'-aminophenyl)-2,7,7-trimethyl-5-oxo-1,4,5,6,7,8-hexahydro-quinoline-3-carboxylate

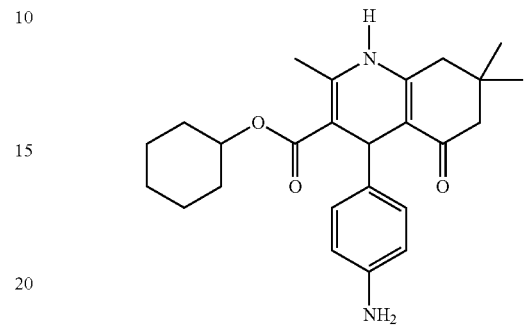

A schlenk-flask was purged with nitrogen and a solution of nitroarene 1 (0.408 mg, 1.00 mmol) in MeOH (30 ml, anhydrous, degassed) was introduced, followed by Pd/C (5% on charcoal (10 mg). Hydrogen gas was introduced (1 bar) and conversion followed by TLC (EtOAc/PE, 1:1). After turnover was complete (2 h) the mixture was filtered and the solvent was evaporated. The crude product was purified by radial chromatography (Chromatotron®) under N2-Atmosphere (CH2Cl2/MeOH 99:1), then dissolved in EtOH (1 mL), triturated with cyclohexane and dried in vacuo. Off-white powder sensitive to air, must be stored below ambient temperature; yield 95%; 1H NMR (250 MHz, DMSO-d6): ä 7.01 (d, J=8.3 Hz, 2H), 6.54 (d, J=8.3 Hz, 2H), 5.79 (br s, 1H), 4.93 (s, 1H), 4.69-4.66 (m, 1H), 2.36 (s, 3H), 2.27-2.17 (m, 4H), 1.62-1.24 (m, 10H), 1.07 (s, 3H), 0.94 (s, 3H); 13C NMR (101 MHz, CDCl3): ä=200.4, 194.7, 166.5, 151.2, 150.2, 145.8, 137.5, 127.4, 127.4, 109.9, 103.8, 71.4, 50.6, 36.5, 32.6, 31.7, 31.4, 29.5, 26.9, 25.4, 23.6; MS (EI): m/z (%)=408 (M+) (8), 406 (6), 390 (8), 392 (5), 318 (5), 316 (100), 234 (92), 216 (25), 177 (16), 93 (97).

E-2-(((3'-Cyclohexyloxycarbonyl-4"-nitrophenyl-2', 7',7'-trimethyl-1',4',5',6',7',8'-hexahydroquinoline-5'-ylidene)amino)oxy)acetic acid (6)

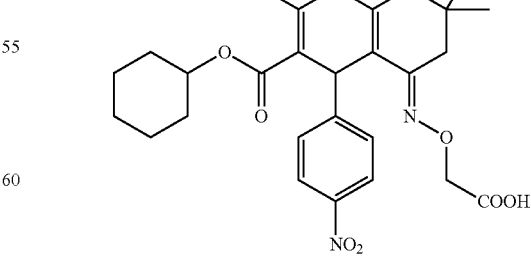

A solution of O-(Carboxymethyloxmethyl)hydroxylamine hemihydrochloride (2.06 mmol, 225 mg, Aldrich) in water (5 mL) was adjusted to pH 5 with solid sodium carbonate. This solution was evaporated to dryness in vacuo and the residue was suspended in methanol (6 mL).

To a solution of ketone 1 (0.5 mmol, 219 mg) in acetonitrile (8 mL), phosphorus oxychloride (5 mmol, 500 iL) was added under nitrogen at 30° C. and brought to reflux for 3 h. The orange reaction mixture was evaporated at 50° C. i. V. (6 mbar) and dried until odorless (POCl3). The dark residue was dissolved in acetonitrile (6 mL) and freshly prepared methanolic O-(carboxymethyloxmethyl)hydroxylamine solution (6 mL, see above) was added at once. The mixture was heated to reflux for 5 min before all the solvents were evaporated. The residue was taken up with 20 mL of ethyl acetate, washed with water (2×10 mL), brine (1×10 mL), dried with MgSO4, and evaporated to dryness. The residue was dissolved in 3 mL of methyl tert-butyl ether (MTBE) and stored at 5° C. for 4 days. The crystalline product was retrieved by filtration and dried in vacuo to yield 148 mg of oxime 10. On concentration a second crop of 10 could be obtained by recrystallization from MTBE/n-hexane.

Amber colored crystals; yield: 58%; m.p. 129-133° C.; 1H NMR (250 MHz, CDCl3): ä 8.02 (d, J=8.5 Hz, 2H), 7.43 (d, J=8.5 Hz, 2H), 5.72 (s, 1H); 5.06 (s, 1H), 4.70-4.60 (m, 1H), 2.23 (dd, J=4, 142.5 Hz, 2H), 2.28 (dd, J=5.2, 16.7 Hz, 2H), 2.36 (s, 3H), 2.33-2.16 (m, 4H), 1.80-1.21 (m, 10H), 1.06 (s, 3H), 0.85 (s, 3H); 13C NMR (CDCl3, 62.5 MHz): ä 173.8, 166.2, 155.9, 154.9, 146.0, 144.7, 137.2, 129.3, 122.8, 105.7, 102.6, 72.9, 70.1, 40.7, 38.4, 36.2, 31.9, 31.7, 30.45, 29.5, 27.1, 25.4, 23.9, 23.8, 20.1; ESI HRMS: calcd for (M++H+): C27H34N3O7: 512.2390. found: 512.2390; analysis calcd. for C27H33N3O7×MTBE: C, 64.0; H, 7.6; N, 7.0. found C, 63.5; H, 8.0; N, 6.9.

Typical side products of Hantzsch-type dihydropyridine syntheses.

2,2'-((4-Nitrophenyl)methylene)bis(3-hydroxy-5,5-dimethylcyclohex-2-enone)

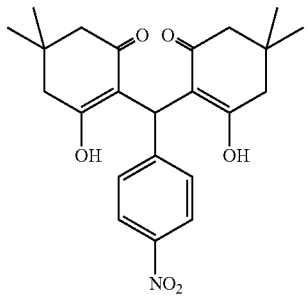

Obtained from the representative procedure for dihydropyridine synthesis. After completion the crude mixture was recrystallized from EtOH/H2O. The first crop was recrystallized again to afford the pure title compound. Off-white crystals; yield: 30%; 1H NMR (250 MHz, CDCl3): ä=11.80 (s, 1H), 11.22 (br s, 1H) 8.15 (d, J=8.8 Hz, 2H), 7.26 (d, J=8.8 Hz, 2H), 5.55 (s, 1H), 2.54-2.29 (m, 8H), 1.24 (s, 6H), 1.12 (s, 6H); 13C NMR (62.5 MHz, CDCl3): ä=190.9, 189.6, 146.5, 146.1, 127.6, 123.5, 114.9, 46.9, 46.4, 33.2, 31.5, 29.5, 27.4; MS (ESI): m/z (%)=436.2 (M+Na)+; analysis calcd. for C23H27NO6: C, 66.8; H, 6.6; N, 3.4. found C, 66.6; H, 6.4; N, 3.2.

2,2'-((3-Nitrophenyl)methylene)bis(3-hydroxy-5,5-dimethylcyclohex-2-enone)

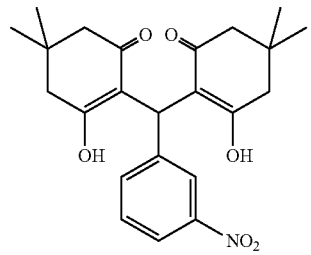

Obtained from the representative procedure for dihydropyridine synthesis. After completion the crude mixture was recrystallized from EtOH/H2O. The first crop was recrystallized again to provide the pure title compound. Light yellow crystals; yield: 61%; m.p. 202° C.; 1H NMR (250 MHz, CDCl3): ä 11.8 (s, 1H), 11.3 (br s, 1H), 8.06 (m, 2H), 7.45 (m, 2H), 5.54 (s, 1H), 2.54-2.29 (m, 8H), 1.28 (s, 6H), 1.12 (s, 6H); 13C NMR (61.5 MHz, CDCl3): ä 191.0, 189.6, 148.4, 140.7, 132.8, 129.1, 122.2, 121.0, 114.8, 46.0, 46.4, 32.9, 31.4, 29.7, 27.3.

Crystal Structure Analysis Data of FLI-06

Intensity data were collected on a Nonius Kappa CCD diffractometer using graphite-monochromated Mo—K<radiation. Data were corrected for Lorentz and polarization effects but not for absorption effects (COLLECT, Data Collection Software; Nonius B.V., The Netherlands (1998) (Supp. Ref 12). The structures were solved by direct methods (SHELXS) (supp. Ref 13) and refined by full-matrix least squares techniques against Fo (supp. Ref 13) (SHELXL-97). All hydrogen atoms were located by difference Fourier synthesis and refined isotropically. All non-hydrogen atoms were refined anisotropically. Crystallographic data as well as structure solution and refinement details are summarized in table 3. XP (SIEMENS Analytical X-ray Instruments, Inc.) was used for structure representations. See also FIG. 19.

Zebrafish:

Embryos were obtained from natural spawning of wild-type TüAB strain adults, raised and staged according to supp. Ref 14. DAPT and compounds were applied at 50 iM in E3 embryo medium to zebrafish embryos with chorions torn but not completely removed from sphere stage until the stage of analysis, according to ref 23. Control embryos were mock treated with the same concentration of DMSO dissolved in E3 embryo medium. All embryos were incubated in a 24-well plate (10-15 embryos/well; 2 ml final volume) at 28° C. until analysis and then fixed in ice-cold buffered 4% paraformaldehyde overnight. Whole-mount in situ hybridizations (ISH) were performed essentially as described (supp. Ref 16). Digoxigenin-labeled antisense riboprobes were generated from linearized vectors as described (ref 26). For qRT-PCR analysis total RNA was isolated from five zebrafish embryos showing similar phenotype using the RNeasy Mini Kit (Qiagen). In order to discard unwanted or toxic effects, for qPCR those compound-treated embryos were selected that displayed mild somite defects (see FIG. 11). Subsequent cDNA synthesis was performed using the SuperScript III RT kit (Invitrogen), random hexamer primers (Promega) and 500 ng total RNA as template. Quantitative real-time RT-PCR analysis of cDNA was carried out using the SYBR greenER qPCR super mix for iCycler (Invitrogen) in an iCycler device (96-well format; Biorad). All samples were measured as triplicates and normalized to the corresponding amounts of ef1a cDNA measured within the same plate. Relative expression levels where calculated using the 2-ÄÄCT method (supp. Ref 18). For imaging embryos were washed twice in E3 embryo medium and treated with a 0.016% tricaine (MS-222, Sigma) solution in E3 embryo medium. Then embryos were embedded in 3% methylcellulose for imaging. Live embryos (20 to 24 hpf) were scored for morphologic defects using an epifluorescence Stereo Discovery V8 microscope (Carl Zeiss). Images were generated using the AxioVision software (Zeiss). Images of ISH were taken in embryos mounted in 70% glycerol/PBST.

TABLE 2

Small molecule screening data.

| Category | Parameter | Description |
|---|---|---|
| Assay | Type of assay | Cell based, image based |
|  | Target | Notch-trafficking |
|  | Primary measurement | EGFP fluorescence |
|  | Key reagents | DMSO, DAPT |
|  | Assay protocol | Measurement of nuc/enuc fluorescence intensity ratio of a GFP-tagged Notch reporter |
|  | Additional comments |  |
| Library | Library size | ChemBioNet Library (Lisurek, 2010). 16,671 compounds. |
|  | Library composition | Chemical Diversity, Bioactivity enriched. |
|  | Source | ChemDiv (San Diego) through Leibniz-Institute for molecular pharmacology, Berlin, |
|  | Additional comments |  |
| Screen | Format | 384 well microtiter plates |
|  | Concentration(s) tested | 10 µM |
|  | Plate controls | 3000 cells were preseeded in 384 well plates. The next day compounds were added from a 1 mM Stock to yield 10 µM final concentration in 50 µl total volume. Plates were incubated for 24 h at 37° C., 95% RH, 5% CO2 and processed as follows. Medium was aspirated, cells were fixed in 4% formalin for 20 min, stained with Hoechst 33342, rinsed and covered with PBS. |
|  | Reagent/compound dispensing system | Caliper (PerkinElmer) |
|  | Detection instrument and software | ArrayScan VTi (Ceilomics/ThermoFisher), CellularCompartment BioApplication |
|  | Assay validation/QC | 352 top scorers, were rescreened with serial dilutions |
|  | Correction factors | — |
|  | Normalization | z-score |
|  | Additional comments |  |
| Post-HTS analysis | Hit criteria | Visual inspection |
|  | Hit rate | 68 (0.4%) |
|  | Additional assay(s) | — |
|  | Confirmation of hit purity and structure | Confirmation of purity and structure was performed for followed-up hit compounds. (See suppl. methods) |
|  | Additional comments |  |

TABLE 3

Crystal data and refinement details for the X-ray structure determinations of the compound FLI-06.

| Compound | FLI-06 |
|---|---|
| formula | $C_{25}H_{30}N_2O_5$ |
| fw (g · mol$^{-1}$) | 438.51 |
| T/° C. | −140(2) |
| crystal system | monoclinic |
| space group | $P2_1/c$ |
| a/Å | 18.0463(9) |
| b/Å | 10.4521(5) |
| c/Å | 12.3077(4) |
| α/° | 90.00 |
| β/° | 101.616(3) |
| γ/° | 90.00 |
| V/Å$^3$ | 2273.95(17) |
| Z | 4 |
| ρ (g · cm$^{-3}$) | 1.281 |
| µ (mm$^{-1}$) | .89 |
| measured data | 12592 |
| data with I > 2σ(I) | 4320 |
| unique data ($R_{int}$) | 5142/0.0359 |
| wR$_2$ (all data, on F$^2$)$^{a)}$ | 0.1261 |
| R$_1$ (I > 2σ(I))$^{a)}$ | 0.0516 |
| S$^{b)}$ | 1.147 |
| Res. dens./e · Å$^{-3}$ | 0.255/−0.241 |
| absorpt method | NONE |
| CCDC No. | 911241 |

$^{a)}$Definition of the R indices: $R_1 = (\Sigma||F_o| - |F_c||)/\Sigma|F_o|$; $wR_2 = \{\Sigma[w(F_o^2 - F_c^2)^2]/\Sigma[w(F_o^2)^2]\}^{1/2}$ with $w^{-1} = \sigma^2(F_o^2) + (aP)^2 + bP$; $P = [2F_c^2 + \text{Max}(F_o^2)]/3$;
$^{b)}S = \{\Sigma[w(F_o^2 - F_c^2)^2]/(N_o - N_p)\}^{1/2}$.

REFERENCES

1. Kopan, R. & Ilagan, M. X. The canonical Notch signaling pathway: unfolding the activation mechanism. Cell 137, 216-233, (2009).
2. McCarthy, J. V., Twomey, C. & Wujek, P. Presenilin-dependent regulated intramembrane proteolysis and gamma-secretase activity. Cell Mol Life Sci 66, 1534-1555, (2009).
3. Chen, F. et al. TMP21 is a presenilin complex component that modulates gamma-secretase but not epsilon-secretase activity. Nature 440, 1208-1212, (2006).
4. Thathiah, A. et al. The orphan G protein-coupled receptor 3 modulates amyloid-beta peptide generation in neurons. Science 323, 946-951, (2009).
5. He, G. et al. Gamma-secretase activating protein is a therapeutic target for Alzheimer's disease. Nature 467, 95-98, (2010).
6. Mitsuishi, Y. et al. Human CRB2 inhibits gamma-secretase cleavage of amyloid precursor protein by binding to the presenilin complex. The Journal of biological chemistry 285, 14920-14931, (2010).
7. Le Borgne, R. Regulation of Notch signalling by endocytosis and endosomal sorting. Current opinion in cell biology 18, 213-222, (2006).
8. Real, P. J. & Ferrando, A. A. NOTCH inhibition and glucocorticoid therapy in T-cell acute lymphoblastic leukemia. Leukemia 23, 1374-1377, (2009).
9. Koch, U. & Radtke, F. Notch in T-ALL: new players in a complex disease. Trends Immunol 32, 434-442, (2011).
10. von Kleist, L. & Haucke, V. At the Crossroads of Chemistry and Cell Biology: Inhibiting Membrane Traffic by Small Molecules. Traffic, (2011).
11. Dovey, H. F. et al. Functional g-secretase inhibitors reduce b-amyloid peptide levels in brain. J Neurochem 76, 173-181., (2001).
12. Shearman, M. S. et al. L-685,458, an aspartyl protease transition state mimic, is a potent inhibitor of amyloid b-protein precursor g-secretase activity. Biochemistry 39, 8698-8704, (2000).
13. Wolfe, M. S. gamma-Secretase inhibitors and modulators for Alzheimer's disease. Journal of neurochemistry, (2011).
14. Zanella, F., Lorens, J. B. & Link, W. High content screening: seeing is believing. Trends Biotechnol 28, 237-245, (2010).
15. Hünniger, K. et al. Notch1 signaling is mediated by importins alpha 3, 4, and 7. Cell Mol Life Sci 67, 3187-3196, (2010).
16. Mollenhauer, H. H., Morre, D. J. & Rowe, L. D. Alteration of intracellular traffic by monensin; mechanism, specificity and relationship to toxicity. Biochimica et biophysica acta 1031, 225-246, (1990).
17. Lisurek, M. et al. Design of chemical libraries with potentially bioactive molecules applying a maximum common substructure concept. Mol Divers 14, 401-408, (2010).
18. Citron, M. et al. Mutation of the b-amyloid precursor protein in familial Alzheimer's disease increases b-protein production. Nature 360, 672-674, (1992).
19. Haass, C. Take five-BACE and the gamma-secretase quartet conduct Alzheimer's amyloid beta-peptide generation. EMBO J. 23, 483-488, (2004).
20. Bloch, L. et al. Klotho is a substrate for alpha-, beta- and gamma-secretase. FEBS letters 583, 3221-3224, (2009).
21. Kopan, R., Nye, J. S. & Weintraub, H. The intracellular domain of mouse Notch: a constitutively activated repressor of myogenesis directed at the basic helix-loop-helix region of MyoD. Development 120, 2385-2396, (1994).
22. Dahlqvist, C. et al. Functional Notch signaling is required for BMP4-induced inhibition of myogenic differentiation. Development 130, 6089-6099, (2003).
23. Geling, A., Steiner, H., Willem, M., Bally-Cuif, L. & Haass, C. A {gamma}-secretase inhibitor blocks Notch signaling in vivo and causes a severe neurogenic phenotype in zebrafish. EMBO Rep 3, 688-694., (2002).
24. Kitzmann, M. et al. Inhibition of Notch signaling induces myotube hypertrophy by recruiting a subpopulation of reserve cells. Journal of cellular physiology 208, 538-548, (2006).
25. Blader, P. & Strahle, U. Zebrafish developmental genetics and central nervous system development. Human molecular genetics 9, 945-951, (2000).
26. Blader, P., Fischer, N., Gradwohl, G., Guillemot, F. & Strahle, U. The activity of neurogenin1 is controlled by local cues in the zebrafish embryo. Development 124, 4557-4569, (1997).
27. Chung, P. C. et al. Zebrafish Her8a is activated by Su(H)-dependent Notch signaling and is essential for the inhibition of neurogenesis. PloS one 6, e19394, (2011).
28. Pavelka, M. & Ellinger, A. Effect of colchicine on the Golgi complex of rat pancreatic acinar cells. The Journal of cell biology 97, 737-748, (1983).
29. Lippincott-Schwartz, J., Yuan, L. C., Bonifacino, J. S. & Klausner, R. D. Rapid redistribution of Golgi proteins into the ER in cells treated with Brefeldin A: Evidence for membrane cycling from Golgi to ER. Cell 56, 801-813, (1989).
30. Saenz, J. B. et al. Golgicide A reveals essential roles for GBF1 in Golgi assembly and function. Nat Chem Biol 5, 157-165, (2009).
31. Rothman, J. E. Mechanisms of intracellular protein transport. Nature 372, 55-63, (1994).
32. Donaldson, J. G., Cassel, D., Kahn, R. A. & Klausner, R. D. ADP-ribosylation factor, a small GTP-binding protein, is required for binding of the coatomer protein beta-COP to Golgi membranes. Proceedings of the National Academy of Sciences of the United States of America 89, 6408-6412, (1992).
33. Helms, J. B. & Rothman, J. E. Inhibition by brefeldin A of a Golgi membrane enzyme that catalyses exchange of guanine nucleotide bound to ARF. Nature 360, 352-354, (1992).
34. Szul, T. et al. Dissection of membrane dynamics of the ARF-guanine nucleotide exchange factor GBF1. Traffic 6, 374-385, (2005).
35. Toomre, D., Keller, P., White, J., Olivo, J. C. & Simons, K. Dual-color visualization of trans-Golgi network to plasma membrane traffic along microtubules in living cells. J Cell Sci, 21-33, (1999).
36. Presley, J. F. et al. ER-to-Golgi transport visualized in living cells. Nature 389, 81-85, (1997).
37. Dukhovny, A., Papadopulos, A. & Hirschberg, K. Quantitative live-cell analysis of microtubule-uncoupled cargo-protein sorting in the ER. Journal of cell science 121, 865-876, (2008).
38. Kim, J. et al. Biogenesis of gamma-secretase early in the secretory pathway. The Journal of cell biology 179, 951-963, (2007).
39. Lee, T. H. & Linstedt, A. D. Potential role for protein kinases in regulation of bidirectional endoplasmic reticulum-to-Golgi transport revealed by protein kinase inhibitor H89. Molecular biology of the cell 11, 2577-2590, (2000).

40 Lathia, J. D., Mattson, M. P. & Cheng, A. Notch: from neural development to neurological disorders. J Neurochem 107, 1471-1481, (2008).

41 Imbimbo, B. P. & Giardina, G. A. gamma-secretase inhibitors and modulators for the treatment of Alzheimer's disease: disappointments and hopes. Curr Top Med Chem 11, 1555-1570, (2011).

42 Groth, C. & Fortini, M. E. Therapeutic approaches to modulating Notch signaling: Current challenges and future prospects. Seminars in cell & developmental biology, (2012).

43 Vetrivel, K. S. et al. Spatial segregation of gamma-secretase and substrates in distinct membrane domains. The Journal of biological chemistry 280, 25892-25900, (2005).

44 Goldmann, S. & Stoltefuss, J. 1,4-Dihydropyridines: Effects of Chirality and Conformation on the Calcium Antagonist and Calcium Agonist Activities. Angew. Chem. Int Ed. Engl. 30, 1559-1578 30, 1559-1578, (1991).

45 Edraki, N., Mehdipour, A. R., Khoshneviszadeh, M. & Miri, R. Dihydropyridines: evaluation of their current and future pharmacological applications. Drug Discov Today 14, 1058-1066, (2009).

46 Dietz, J. D. et al. A number of marketed dihydropyridine calcium channel blockers have mineralocorticoid receptor antagonist activity. Hypertension 51, 742-748, (2008).

47 Fagart, J. et al. A new mode of mineralocorticoid receptor antagonism by a potent and selective nonsteroidal molecule. The Journal of biological chemistry 285, 29932-29940, (2010).

48 Meredith, P. A. & Elliott, H. L. Dihydropyridine calcium channel blockers: basic pharmacological similarities but fundamental therapeutic differences. J Hypertens 22, 1641-1648, (2004).

49 Zanetti, G., Pahuja, K. B., Studer, S., Shim, S. & Schekman, R. COPII and the regulation of protein sorting in mammals. Nature cell biology 14, 20-28, (2012).

50 Schroeter, E. H., Kisslinger, J. A. & Kopan, R. Notch-1 signalling requires ligand-induced proteolytic release of intracellular domain. Nature 393, 382-386, (1998).

51 Ritz, C. & Streibig, J. C. Bioassay Analysis using R. J Statist Software 12, (2005).

52 Sastre, M. et al. Presenilin-dependent gamma-secretase processing of beta-amyloid precursor protein at a site corresponding to the S3 cleavage of Notch. EMBO Rep 2, 835-841, (2001).

53 Steiner, H. et al. Glycine 384 is required for presenilin-1 function and is conserved in polytopic bacterial aspartyl proteases. Nature Cell Biol 2, 848-851, (2000).

54 Steiner, H. et al. PEN-2 is an integral component of the gamma-secretase complex required for coordinated expression of presenilin and nicastrin. J Biol Chem 277, 39062-39065., (2002).

55 Wacker, I. et al. Microtubule-dependent transport of secretory vesicles visualized in real time with a GFP-tagged secretory protein. J Cell Sci 110, 1453-1463., (1997).

SUPPLEMENTAL REFERENCES

1 Kato, Y. et al. Establishment of the anti-Klotho monoclonal antibodies and detection of Klotho protein in kidneys. Biochem Biophys Res Commun 267, 597-602 (2000).

2 Steiner, H. et al. PEN-2 is an integral component of the gamma-secretase complex required for coordinated expression of presenilin and nicastrin. J Biol Chem 277, 39062-39065. (2002).

3 Snapp, E. L., Sharma, A., Lippincott-Schwartz, J. & Hegde, R. S. Monitoring chaperone engagement of substrates in the endoplasmic reticulum of live cells. Proceedings of the National Academy of Sciences of the United States of America 103, 6536-6541 (2006).

4 Wang, Y. et al. Activation of ATF6 and an ATF6 DNA binding site by the endoplasmic reticulum stress response. The Journal of biological chemistry 275, 27013-27020 (2000).

6 Malo, N., Hanley, J. A., Cerquozzi, S., Pelletier, J. & Nadon, R. Statistical practice in high-throughput screening data analysis. Nat Biotechnol 24, 167-175 (2006).

7 Zhang, J. H., Chung, T. D. & Oldenburg, K. R. A Simple Statistical Parameter for Use in Evaluation and Validation of High Throughput Screening Assays. J Biomol Screen 4, 67-73 (1999).

8 Amarego, W. L. F. & Chai, C. L. L. Purification of laboratory chemicals. 6th Edition edn, (Butterworth-Heinemann, 2009).

9 Li, A. H., Moro, S., Melman, N., Ji, X. D. & Jacobson, K. A. Structure-activity relationships and molecular modeling of 3,5-diacyl-2,4-dialkylpyridine derivatives as selective A3 adenosine receptor antagonists. J Med Chem 41, 3186-3201 (1998).

10 Evans, C. G. & Gestwicki, J. E. Enantioselective organocatalytic Hantzsch synthesis of polyhydroquinolines. Org Lett 11, 2957-2959 (2009).

11 Davood, A., Nematollahi, A. R., Iman, M. & Shafiee, A. Synthesis and docking studies of new 1,4-dihydropyridines containing 4-(5)-Chloro-2-ethyl-5-(4)-imidazolyl substituent as novel calcium channel agonist. Arch Pharm Res 32, 481-487 (2009).

12 Otwinowski, Z. & Minor, W. Processing of X-Ray Diffraction Data Collected in Oscillation Mode. Methods in enzymology 276, 307-326 (1997).

13 Sheldrick, G. M. A short history of SHELX. Acta Crystallogr A 64, 112-122 (2008).

14 Kimmel, C. B., Ballard, W. W., Kimmel, S. R., Ullmann, B. & Schilling, T. F. Stages of embryonic development of the zebrafish. Dev Dyn 203, 253-310 (1995).

16 Thisse, C. & Thisse, B. High-resolution in situ hybridization to whole-mount zebrafish embryos. Nature protocols 3, 59-69 (2008).

18 Livak, K. J. & Schmittgen, T. D. Analysis of relative gene expression data using real-time quantitative PCR and the 2(-Delta Delta C(T)) Method. Methods 25, 402-408 (2001).

The invention claimed is:

1. A method for the treatment of a cancer in a subject, wherein said cancer is susceptible to inhibition of Notch signaling, the method comprising inhibiting a Notch signaling pathway by administering a compound according to general formula II to said subject:

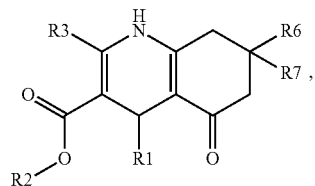

Formula II wherein

R1 is one of:

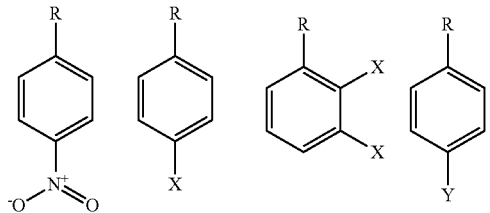

X is H or a halogen and Y is COOCH$_3$,

R2 is a straight chain or branched alkyl group of C$_1$-C$_8$, or a carbon ring structure of C$_5$-C$_8$, R3 is H or a straight chain or branched alkyl group of C$_1$-C$_6$, and R6 and R7 are CH$_3$.

2. The method according to the claim 1, wherein the cancer to be treated is characterized by a dependency on membrane traffic, secretion or a secretory pathway, related to and/or mediated by wnt secretion, microRNA secretion, CCL2-secretion, ER transport and/or the Golgi apparatus.

3. The method according to claim 1, wherein the cancer is chronic lymphocytic leukemia (CLL), esophageal cancer, glioma, colon cancer, haematological cancer, colorectal cancer, cervical cancer, pancreatic cancer, breast cancer or lung cancer.

4. The method according to claim 3, whereby the haematological cancer is a lymphoma or leukemia.

5. The method according to claim 4, whereby the lymphoma is a T-cell lymphoma, B-cell lymphoma or Hodgkin lymphoma.

6. The method of claim 1, wherein the compound according to general formula II is a compound of general formula III:

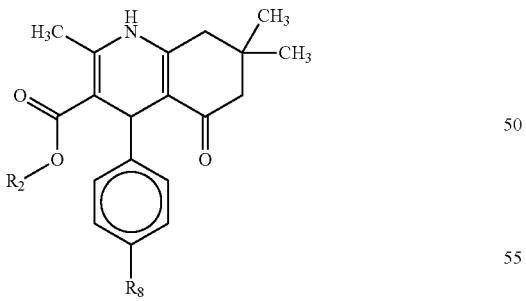

wherein R2 is a straight chain or branched alkyl group of C$_1$-C$_8$, or a carbon ring structure of C$_5$-C$_8$, and wherein R$_8$ is selected from the group consisting of H, COOCH$_3$ and NO$_2$.

7. The method of claim 1, wherein the compound according to general formula II is a compound selected from the group consisting of FLI-06, FLI-24, FLI-25, FLI-26, FLI-27 and FLI-28:

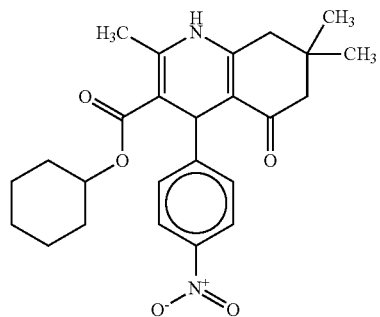
FLI-06

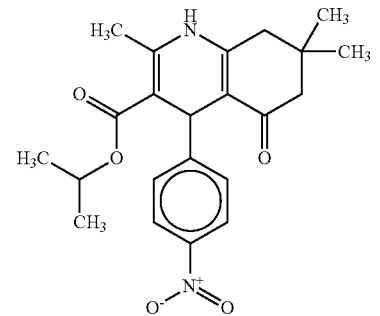
FLI-24

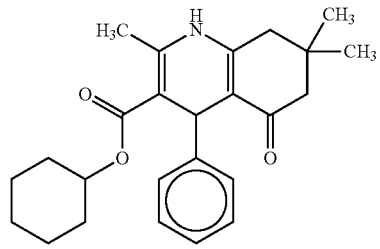
FLI-25

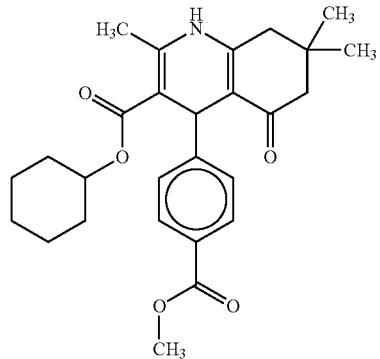
FLI-26

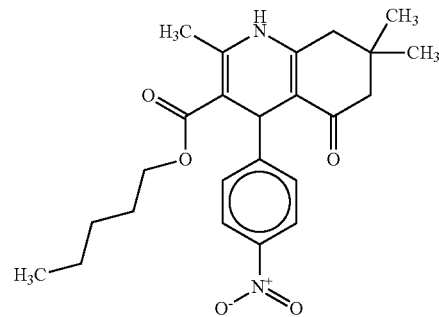
FLI-27

-continued
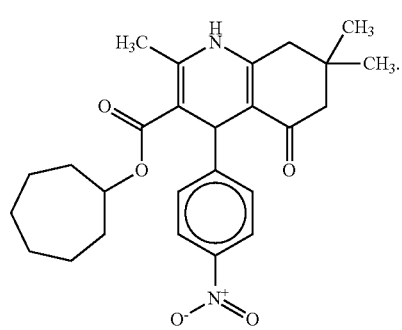
FLI-28
8. The method according to claim 1, wherein X is F, Cl, Br or I.
9. The method according to claim 1, wherein R2 is one of:
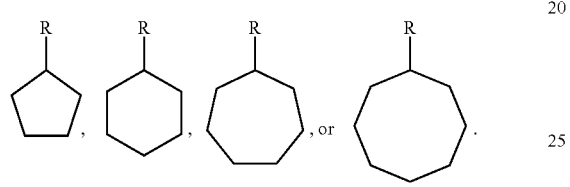
* * * * *